United States Patent [19]

Wareing

[11] Patent Number: 4,613,610
[45] Date of Patent: Sep. 23, 1986

[54] CHOLESTEROL BIOSYNTHESIS INHIBITING PYRAZOLE ANALOGS OF MEVALONOLACTONE AND ITS DERIVATIVES

[75] Inventor: James R. Wareing, Randolph, N.J.

[73] Assignee: Sandoz Pharmaceuticals Corp., E. Hanover, N.J.

[21] Appl. No.: 741,903

[22] Filed: Jun. 6, 1985

Related U.S. Application Data

[63] Continuation-in-part of Ser. No. 623,393, Jun. 22, 1984, abandoned.

[51] Int. Cl.[4] .................. A61K 31/415; C07D 231/12; C07D 405/06
[52] U.S. Cl. .................................. 514/406; 548/374; 548/378
[58] Field of Search ................. 548/374, 378; 514/406

[56] References Cited

U.S. PATENT DOCUMENTS

| | | | |
|---|---|---|---|
| 3,983,140 | 9/1976 | Endo et al. | 549/292 |
| 4,198,425 | 4/1980 | Mitsui et al. | 549/292 |
| 4,248,889 | 2/1981 | Oka et al. | 560/56 |
| 4,255,444 | 3/1981 | Oka et al. | 549/292 |
| 4,308,378 | 12/1981 | Stokker | 549/292 |
| 4,351,844 | 9/1982 | Patchett et al. | 549/292 |
| 4,361,515 | 11/1982 | Terahara et al. | 549/292 |
| 4,375,475 | 3/1983 | Willard et al. | 549/292 |
| 4,376,863 | 3/1983 | Lam | 549/292 |
| 4,387,242 | 6/1983 | Lam | 560/119 |
| 4,440,927 | 4/1984 | Prugh | 549/292 |
| 4,474,971 | 10/1984 | Wareing | 549/214 |
| 4,503,072 | 3/1985 | Hoffman et al. | 514/529 |

FOREIGN PATENT DOCUMENTS

| | | | |
|---|---|---|---|
| 895445 | 4/1983 | Belgium | 549/292 |
| 38061 | 10/1981 | European Pat. Off. | 549/292 |
| 68038 | 1/1983 | European Pat. Off. | 549/292 |
| 56-7775 | 1/1981 | Japan | 549/292 |
| WO84/02131 | 6/1984 | PCT Int'l Appl. | 548/467 |
| WO84/02903 | 8/1984 | PCT Int'l Appl. | 549/292 |

OTHER PUBLICATIONS

Hulcher, Arch. Biochem. Biophys. 146, 422–427 (1971).
Sato et al., Chem. Pharm. Bull. 28, 1509–1525 (1980).
Singer et al., Proc. Soc. Exp. Biol. Med. 102, 370–373 (1959).

*Primary Examiner*—Richard A. Schwartz
*Assistant Examiner*—Kurt G. Briscoe
*Attorney, Agent, or Firm*—Gerald D. Sharkin; Richard E. Vila; Melvyn M. Kassenoff

[57] ABSTRACT

Compounds of the formula

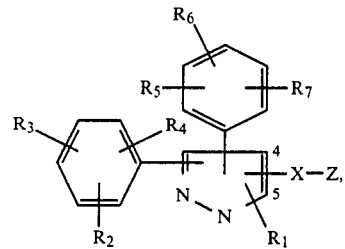

wherein
$R_1$ is $C_{1-6}$alkyl not containing an asymmetric carbon atom,
each of $R_2$ and $R_5$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy,
each of $R_3$ and $R_6$ is independently hydrogen, $C_{1-3}$alkyl, $C_{1-3}$alkoxy, trifluoromethyl, fluoro, chloro, phenoxy or benzyloxy,
each of $R_4$ and $R_7$ is independently hydrogen, $C_{1-2}$alkyl, $C_{1-2}$alkoxy, fluoro or chloro, with the provisos that not more than one of $R_2$ and $R_3$ is trifluoromethyl, not more than one of $R_2$ and $R_3$ is phenoxy, not more than one of $R_2$ and $R_3$ is benzyloxy, not more than one of $R_5$ and $R_6$ is trifluoromethyl, not more than one of $R_5$ and $R_6$ is phenoxy, and not more than one of $R_5$ and $R_6$ is benzyloxy,
X is $-(CH_2)_m-$, $-CH=CH-$, $-CH=CH-CH_2-$ or $-CH_2-CH=CH-$, wherein m is 0, 1, 2 or 3, and
Z is

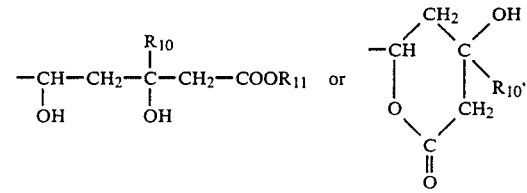

wherein $R_{10}$ is hydrogen or $C_{1-3}$alkyl, wherein $R_{12}$ is a physiologically acceptable and hydrolyzable ester group, and
M is a pharmaceutically acceptable cation, with the provisos that (i) the —X—Z group is in the 4- or 5-position of the pyrazole ring, and (ii) the $R_1$ group and the —X—Z group are ortho to each other, the use thereof for inhibiting cholesterol biosynthesis and lowering the blood cholesterol level and, therefore, in the treatment of hyperlipoproteinemia and atherosclerosis, pharmaceutical compositions comprising such compounds and processes for and intermediates in the synthesis of such compounds.

27 Claims, No Drawings

CHOLESTEROL BIOSYNTHESIS INHIBITING PYRAZOLE ANALOGS OF MEVALONOLACTONE AND ITS DERIVATIVES

This application is a continuation-in-part of application Ser. No. 623,393, filed June 22, 1984 and now abandoned.

This invention relates to compounds of the formula

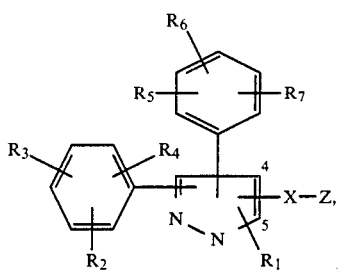

wherein
$R_1$ is $C_{1-6}$alkyl not containing an asymmetric carbon atom,
each of $R_2$ and $R_5$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy,
each of $R_3$ and $R_6$ is independently hydrogen, $C_{1-3}$alkyl, $C_{1-3}$alkoxy, trifluoromethyl, fluoro, chloro, phenoxy or benzyloxy,
each of $R_4$ and $R_7$ is independently hydrogen, $C_{1-2}$alkyl, $C_{1-2}$alkoxy, fluoro or chloro, with the provisos that not more than one of $R_2$ and $R_3$ is trifluoromethyl, not more than one of $R_2$ and $R_3$ is phenoxy, not more than one of $R_2$ and $R_3$ is benzyloxy, not more than one of $R_5$ and $R_6$ is trifluoromethyl, not more than one of $R_5$ and $R_6$ is phenoxy, and not more than one of $R_5$ and $R_6$ is benzyloxy,
X is $-(CH_2)_m-$, $-CH=CH-$, $-CH=CH-CH_2-$ or $-CH_2-CH=CH-$, wherein m is 0, 1, 2 or 3, and

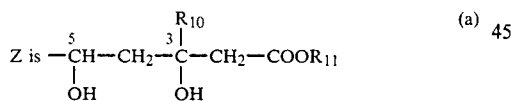

or

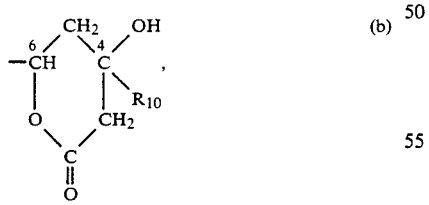

wherein $R_{10}$ is hydrogen or $C_{1-3}$alkyl, and $R_{11}$ is hydrogen, $R_{12}$ or M, wherein
$R_{12}$ is a physiologically acceptable and hydrolyzable ester group, and
M is a pharmaceutically acceptable cation,
with the provisos that (i) the $-X-Z$ group is in the 4- or 5-position of the pyrazole ring, and (ii) the $R_1$ group and the $-X-Z$ group are ortho to each other,
processes for and intermediates in the synthesis thereof, pharmaceutical compositions comprising a compound of Formula I and the use of the compounds of Formula I for inhibiting cholesterol biosynthesis and lowering the blood cholesterol level and, therefore, in the treatment of hyperlipoproteinemia and atherosclerosis.

By the term "physiologically acceptable and hydrolyzable ester group" is meant a group which, together with the $-COO-$ radical to which it is attached, forms an ester group which is physiologically acceptable and hydrolyzable under physiological conditions to yield a compound of Formula I wherein $R_{11}$ is hydrogen and an alcohol which itself is physiologically acceptable, i.e., non-toxic at the desired dosage level, and which, preferably, is free of centers of asymmetry. Examples of such groups are $C_{1-3}$alkyl, n-butyl, i-butyl, t-butyl and benzyl, collectively referred to as $R_{12}'$.

For the avoidance of doubt, throughout this application it is the right-hand side of the X radical that is attached to the Z group.

The compounds of Formula I may be divided into four groups, viz., those of Formulae IA, IB, IC and ID:

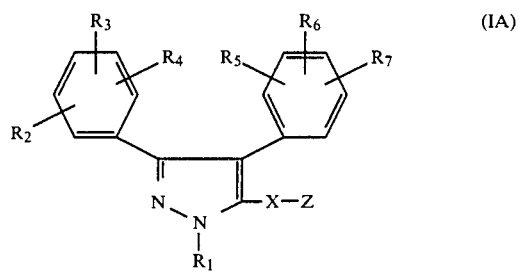

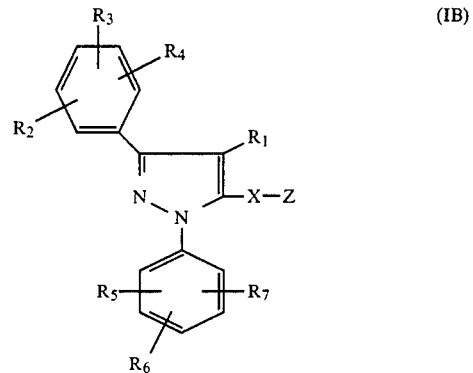

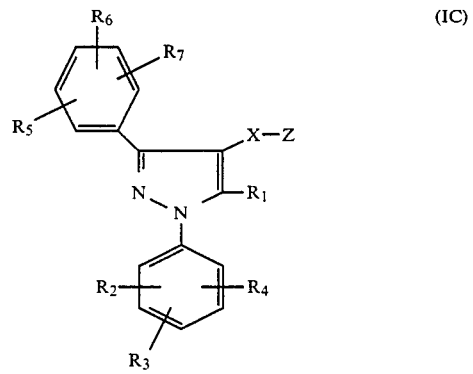

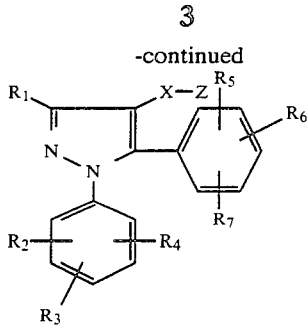

The compounds of each of Groups IA-ID may be divided into two subgroups based upon the significance of Z, viz., Group IAa (the compounds of Group IA wherein Z is a group of Formula a), Group IAb (the compounds of Group IA wherein Z is a group of Formula b), Group IBa (the compounds of Group IB wherein Z is a group of Formula a), Group IBb (the compounds of Group IB wherein Z is a group of Formula b), Group ICa (the compounds of Group IC wherein Z is a group of Formula a), Group ICb (the compounds of Group IC wherein Z is a group of Formula b), Group IDa (the compounds of Group ID wherein Z is a group of Formula a) and Group IDb (the compounds of Group ID wherein Z is a group of Formula b).

As is self-evident to those in the art, each compound of Formula I (and every subscope and species thereof) has two centers of asymmetry (the two carbon atoms bearing the hydroxy groups in the group of Formula a and the carbon atom bearing the hydroxy group and the carbon atom having the free valence in the group of Formula b) and, therefore, there are four stereoisomeric forms (enantiomers) of each compound (two racemates or pairs of diastereoisomers), provided that $R_{11}$ does not contain any center of asymmetry. The four stereoisomers may be designated as the R,R, R,S, S,R and S,S enantiomers, all four stereoisomers being within the scope of this invention. When $R_{11}$ contains one or more centers of asymmetry, there are eight or more stereoisomers. Since it is preferred that $R_{11}$ not contain a center of asymmetry and for reasons of simplicity any additional stereoisomers resulting from the presence of one or more centers of asymmetry in $R_{11}$ usually will be ignored, it being assumed that $R_{11}$ is free of centers of asymmetry.

$R_1$ is preferably $R_1'$, where $R_1'$ is $C_{1-3}$alkyl, n-butyl or i-butyl, more preferably $R_1''$, where $R_1''$ is $C_{1-3}$alkyl, and most preferably isopropyl.

$R_2$ is preferably $R_2'$, where $R_2'$ is hydrogen, $C_{1-3}$alkyl, $C_{1-3}$alkoxy, trifluoromethyl, fluoro or chloro, more preferably $R_2''$, where $R_2''$ is hydrogen or fluoro, and most preferably hydrogen.

$R_3$ is preferably $R_3'$, where $R_3'$ is hydrogen, $C_{1-2}$alkyl, $C_{1-2}$alkoxy, fluoro or chloro, and most preferably hydrogen.

$R_4$ is preferably $R_4'$, where $R_4'$ Is hydrogen or methyl, and most preferably hydrogen.

The $R_2$-bearing phenyl group is preferably unsubstituted.

$R_5$ is preferably $R_5'$, where $R_5'$ is hydrogen, $C_{1-3}$alkyl, $C_{1-3}$alkoxy, trifluoromethyl, fluoro or chloro, more preferably $R_5''$, where $R_5''$ is hydrogen or fluoro, and most preferably fluoro.

$R_6$ is preferably $R_6'$, where $R_6'$ is hydrogen, $C_{1-2}$alkyl, $C_{1-2}$alkoxy, fluoro or chloro, more preferably $R_6''$, where $R_6''$ is hydrogen or methyl, and most preferably hydrogen.

$R_7$ is preferably $R_7'$, where $R_7'$ is hydrogen or methyl, and most preferably hydrogen.

Preferably, when two of $R_5$ ($R_5'$, etc.), $R_6$ ($R_6'$, etc.) and $R_7$ ($R_7'$, etc.) are other than hydrogen and one is hydrogen, at least one of the two that are other than hydrogen is in a meta or para position and not more than one of them is a member of the group consisting of t-butyl, trifluoromethyl, phenyl, phenoxy and benzyloxy; more preferably, the two that are other than hydrogen are not ortho to each other when neither of them is a member of the group consisting of methyl, methoxy, fluoro and chloro.

Preferably, when each of $R_5$ ($R_5'$, etc.), $R_6$ ($R_6'$, etc.) and $R_7$ ($R_7'$, etc.) is other than hydrogen, at least two of them are in meta or para positions, and not more than one of them is a member of the group consisting of t-butyl, trifluoromethyl, phenyl, phenoxy and benzyloxy; more preferably, no two of them are ortho to each other unless at least one member of each pair of substituents that are ortho to each other is a member of the group consisting of methyl, methoxy, fluoro and chloro.

The $R_5$-bearing phenyl group is preferably 4-fluorophenyl or 3,5-dimethylphenyl, preferably the former.

$R_{10}$ is preferably $R_{10}'$, where $R_{10}'$ is hydrogen or methyl, and most preferably hydrogen.

$R_{11}$ is preferably $R_{11}'$, where $R_{11}'$ is hydrogen, $R_{12}'$ or M, more preferably $R_{11}''$, where $R_{11}''$ is hydrogen, $C_{1-3}$alkyl or M, even more preferably $R_{11}'''$, where $R_{11}'''$ is hydrogen, $C_{1-2}$alkyl or M, and most preferably M, especially sodium.

$R_{12}$ is preferably $R_{12}'$, where $R_{12}'$ is $C_{1-3}$alkyl, n-butyl, i-butyl, t-butyl or benzyl, more preferably $C_{1-3}$alkyl, and most preferably $C_{1-2}$alkyl, especially ethyl.

Any —CH=CH—, —CH=CH—CH$_2$— or —CH$_2$—CH=CH— as X is preferably trans, i.e., (E).

X is preferably X', where X' is —CH$_2$CH$_2$— or —CH=CH—, more preferably —CH=CH—, and most preferably $$\begin{array}{c} H \\ \diagdown \\ C=C \\ \diagup \quad \diagdown \\ H \end{array}$$

(i.e., (E)—CH=CH—).

Z is preferably a group of Formula a wherein $R_{10}$ is $R_{10}'$ (especially hydrogen), and $R_{11}$ is $R_{11}'$ or a group of Formula b, more preferably a group of Formula a wherein $R_{10}$ is hydrogen, and $R_{11}$ is $R_{11}''$ or a group of Formula b, even more preferably a group of Formula a wherein $R_{10}$ is hydrogen, and $R_{11}$ is $R_{11}'''$ or a group of Formula b, and most preferably a group of Formula a wherein $R_{10}$ is hydrogen, and $R_{11}$ is M (especially sodium).

m is preferably m', where m' is 2 or 3, most preferably 2.

M is preferably free from centers of asymmetry and is more preferably M', i.e., sodium, potassium or ammonium, and most preferably sodium. For simplicity, each formula in which M appears has been written as if M were monovalent and, preferably, it is. However, it may also be divalent or trivalent and, when it is, balances the charge of two or three carboxy groups, respectively.

Thus, Formula I and every other formula containing an M embraces compounds wherein M is divalent or trivalent, i.e., compounds containing two or three carboxylate-containing anions per cation M.

As between otherwise identical compounds of Formula I, those wherein Z is a group of Formula a are generally preferred over those wherein Z is a group of Formula b.

Insofar as the compounds of Groups IAa, IBa, ICa and IDa and each of the subgroups thereof are concerned, the erythro isomers are preferred over the threo isomers, erythro and threo referring to the relative positions of the hydroxy groups in the 3- and 5-positions of the group of Formula a.

Insofar as the compounds of Groups IAb, IBb, ICb and IDb and each of the subgroups thereof are concerned, the trans lactones are generally preferred over the cis lactones, cis and trans referring to the relative positions of $R_{10}$ and the hydrogen atom in the 6-position of the group of Formula b.

The preferred stereoisomers of the compounds of Formula I having only two centers of asymmetry wherein X is a direct bond, —CH=CH— or —CH$_2$—CH=CH—, and Z is a group of Formula a are the 3R,5S isomer and the racemate of which it is a constituent, i.e., the 3R,5S-3S,5R (erythro) racemate.

The preferred stereoisomers of the compounds of Formula I having only two centers of asymmetry wherein X is —CH$_2$—, —CH$_2$CH$_2$—, —CH$_2$CH$_2$CH$_2$— or —CH=CH—CH$_2$—, and Z is a group of Formula a are the 3R,5R isomer and the racemate of which it is a constituent, i.e., the 3R,5R-3S,5S (erythro) racemate.

The preferences set forth in the preceding two paragraphs also apply to the compounds of Formula I having more than two centers of asymmetry and represent the preferred configurations of the indicated positions.

The preferred stereoisomers of the compounds of Formula I wherein X is a direct bond, —CH=CH— or —CH$_2$—CH=CH—, and Z is a group of Formula b are the 4R,6S and 4R,6R isomers and the racemate of which each is a constituent, i.e., the 4R,6S-4S,6R (trans lactone) and 4R,6R-4S,6S (cis lactone) racemates, with the 4R,6S isomer and the racemate of which it is a constituent being more preferred and the 4R,6S isomer being most preferred.

The preferred stereoisomers of the compounds of Formula I wherein X is —CH$_2$—, —CH$_2$CH$_2$—, —CH$_2$CH$_2$CH$_2$— or —CH=CH—CH$_2$—, and Z is a group of Formula b are the 4R,6R and 4R,6S isomers and the racemate of which each is a constituent, i.e., the 4R,6R-4S,6S (trans lactone) and 4R,6S-4S,6R (cis lactone) racemates, with the 4R,6R isomer and the racemate of which it is a constituent being more preferred and the 4R,6R isomer being most preferred.

Each of the preferences set forth above applies, not only to the compounds of Formula I, but also to the compounds of Formulae IA, IB, IC and ID and those of Groups IAa, IAb, IBa, IBb, ICa, ICb, IDa and IDb as well as to every other subgroup thereof set forth in the specification, e.g., Groups (i) et seq., unless otherwise indicated. When any preference or group contains a variable, the preferred significances of that variable apply to the preference in question, unless otherwise indicated.

Preferred groups of compounds of Formulae IAa and IAb include the compounds (i) of Group IAa wherein $R_1$ is $R_1'$, $R_2$ is $R_2'$, $R_3$ is $R_3'$, $R_4$ is $R_4'$, $R_5$ is $R_5'$, $R_6$ is $R_6'$, $R_7$ is $R_7'$, $R_{10}$ is $R_{10}'$, $R_{11}$ is $R_{11}'$, and X is X', (ii) of (i) wherein $R_2$ is $R_2''$, $R_3$ is hydrogen, $R_4$ is hydrogen, $R_5$ is $R_5''$, $R_6$ is $R_6''$, $R_{10}$ is hydrogen, $R_{11}$ is $R_{11}''$, and X is (E)—CH=CH—, (iii) of (ii) wherein $R_1$ is $R_1''$, (iv)-(vi) of (i)-(iii) wherein $R_{11}$ is M, especially sodium, (vii)-(xii) of (i)-(vi) wherein the hydrogen groups in the 3- and 5-positions of the group of Formula a have the erythro configuration.

(xiii)-(xviii) the 3R,5S enantiomers of the compounds of (vii)-(xii) wherein X is —CH=CH— and the 3R,5R enantiomers of those wherein X is —CH$_2$CH$_2$—, (xix) of Group IAb wherein $R_1$ is $R_1'$, $R_2$ is $R_2'$, $R_3$ is $R_3'$, $R_4$ is $R_4'$, $R_5$ is $R_5'$, $R_6$ is $R_6'$, $R_7$ is $R_7'$, $R_{10}$ is $R_{10}'$, and X is X', (xx) of (xix) wherein $R_2$ is $R_2''$, $R_3$ is hydrogen, $R_4$ is hydrogen, $R_5$ is $R_5''$, $R_6$ is $R_6''$, $R_{10}$ is hydrogen, and X is (E)—CH=CH—, (xxi) of (xx) wherein $R_1$ is $R_1''$, (xxii)-(xxiv) of (xix)-(xxi) wherein $R_{10}$ and the hydrogen atom in the 6-position of the group of Formula b are trans to each other (i.e., the trans lactones), and (xxv)-(xxvii) the 4R,6S enantiomers of the compounds of (xxii)-(xxiv) wherein X is —CH=CH— and the 4R,6R enantiomers of those wherein X is —CH$_2$CH$_2$—.

Groups (viii)-(xii) embrace the 3R,5S-3S,5R racemate and the 3R,5S and 3S,5R enantiomers, the 3S,5R enantiomer being least preferred.

Groups (xxiii) and (xxiv) embrace the 4R,6S-4S,6R racemate and the 4R,6S and 4S,6R enantiomers, the 4S,6R enantiomer being least preferred.

Insofar as Groups IBa, IBb, ICa, ICb, IDa and IDb are concerned, the preferred subgroups are those that correspond to Groups (i)-(xxvii). As should be self-evident, the preferred groups of compounds of Groups IBa, ICa and IDa are those that correspond to Groups (i)-(xviii), i.e., Groups (xxviii)-(xlv), (lv)-(lxxii) and (lxxxii)-(xcix), respectively, and the preferred groups of compounds of Groups IBb, ICb and IDb are those that correspond to Groups (xix)-(xxvii), i.e., Groups (xlvi)-(liv), (lxxiii)-(lxxxi) and (c)-(cviii), respectively.

The compounds of Formula I may be synthesized as follows:

Reaction Scheme I

The compounds of Formula I wherein X is —CH=CH— and Z is a group of Formula b having the 4R,6S configuration or X is —CH$_2$CH$_2$— and Z is a group of Formula b having the 4R,6R configuration may be synthesized by the following series of reactions:

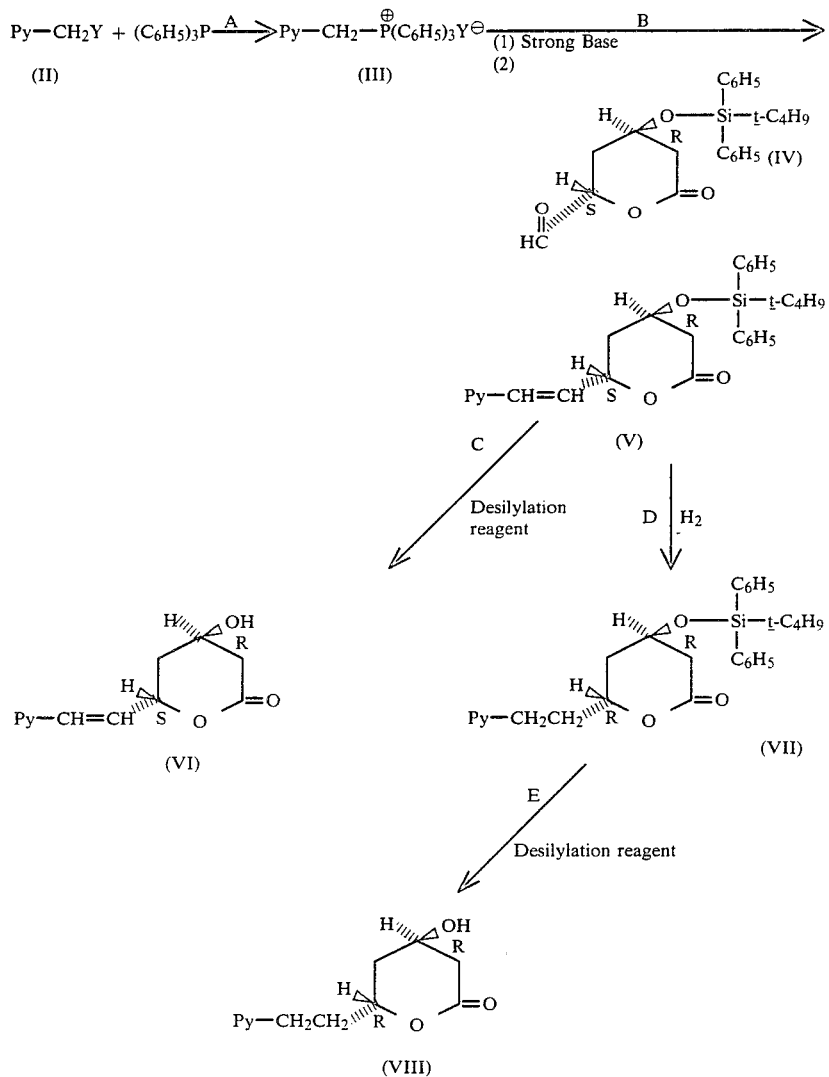
Reaction Scheme II
The compounds of Formula I wherein X is —CH$_2$CH$_2$—, —CH$_2$CH$_2$CH$_2$—, —CH=CH—, —CH=CH—CH$_2$— or —CH$_2$—CH=CH—, and Z is a group of Formula a wherein R$_{11}$ is R$_{12}'$ may be synthesized by the following series of reactions:
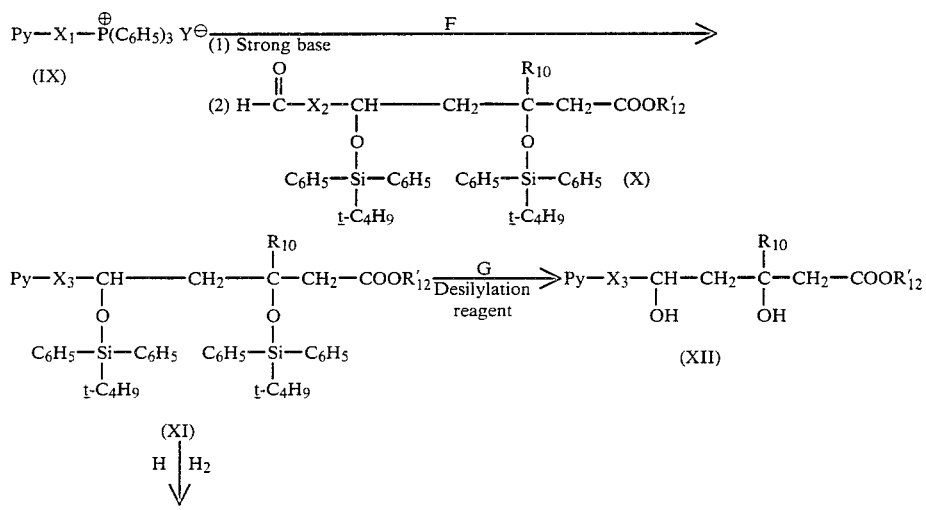

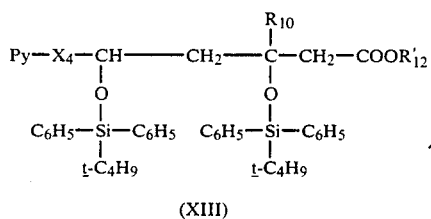
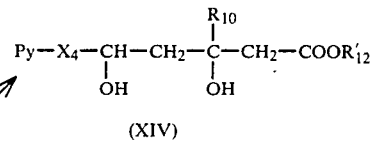

Reaction Scheme III

The compounds of Formula I wherein X is —($CH_2$)$_m$— or (E)—CH=CH—, and Z is a group of Formula a wherein $R_{10}$ is hydrogen, and $R_{11}$ is $R_{12}'$ or $R_{10}$ is $R_{10a}$ and $R_{11}$ is $M_2^{\oplus}$ may be synthesized by the following series of reactions:

Reaction Scheme IV

The compounds of Formula I wherein Z is a group of Formula a wherein $R_{11}$ is $R_{12}'$ or a group of Formula b may be converted into the corresponding compounds of Formula I wherein Z has a different significance by the following series of reactions:

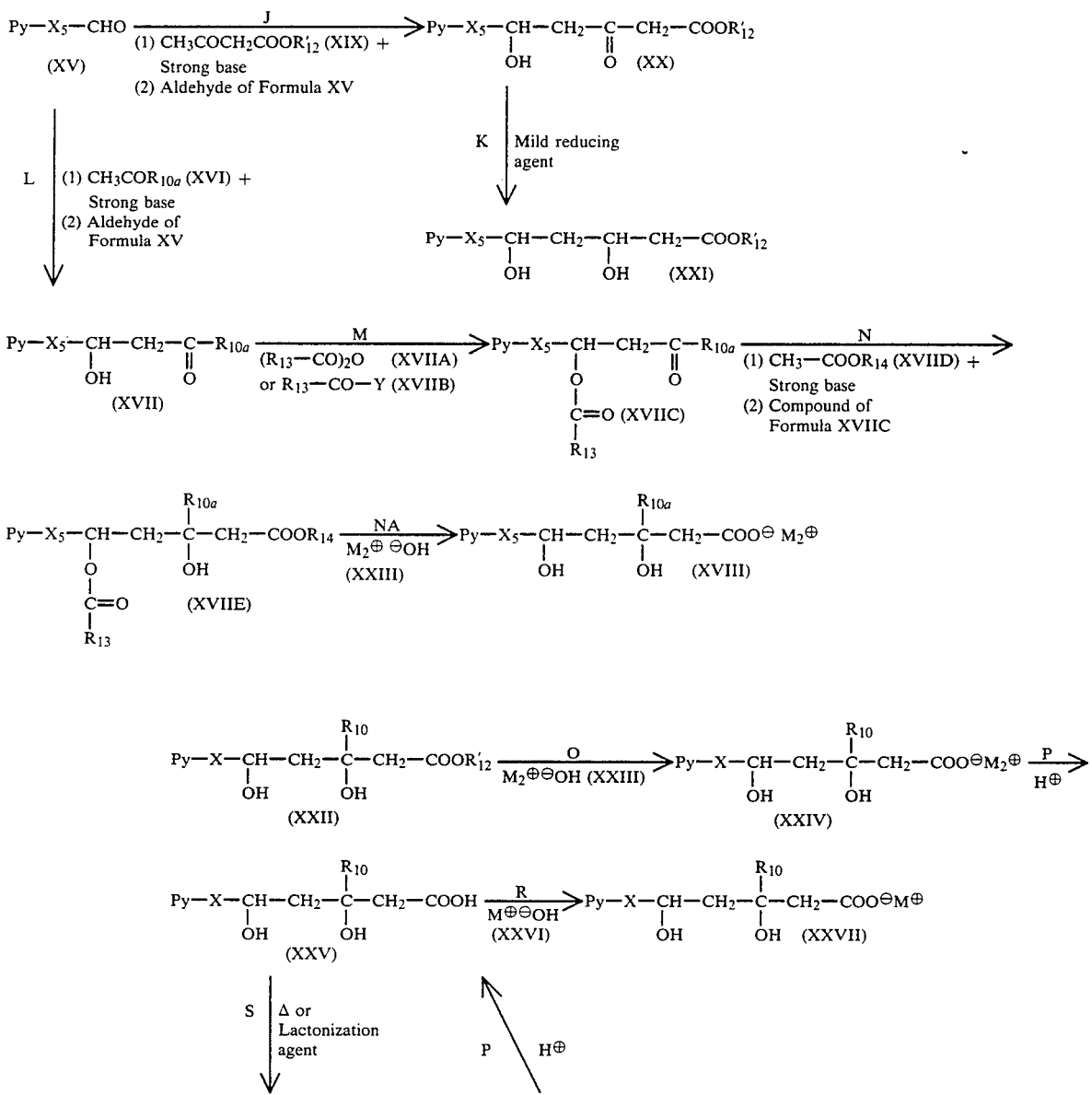

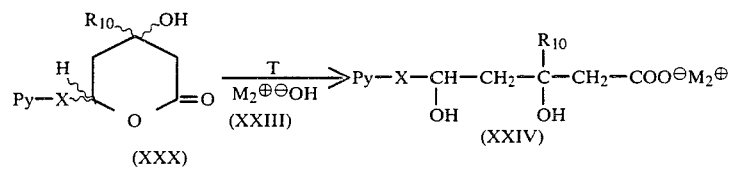
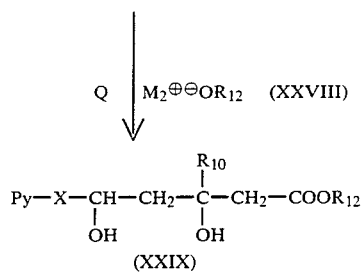
Reaction Scheme V
The compounds of Formulae II and CCI wherein Py is PyA may be synthesized by the following series of reactions:
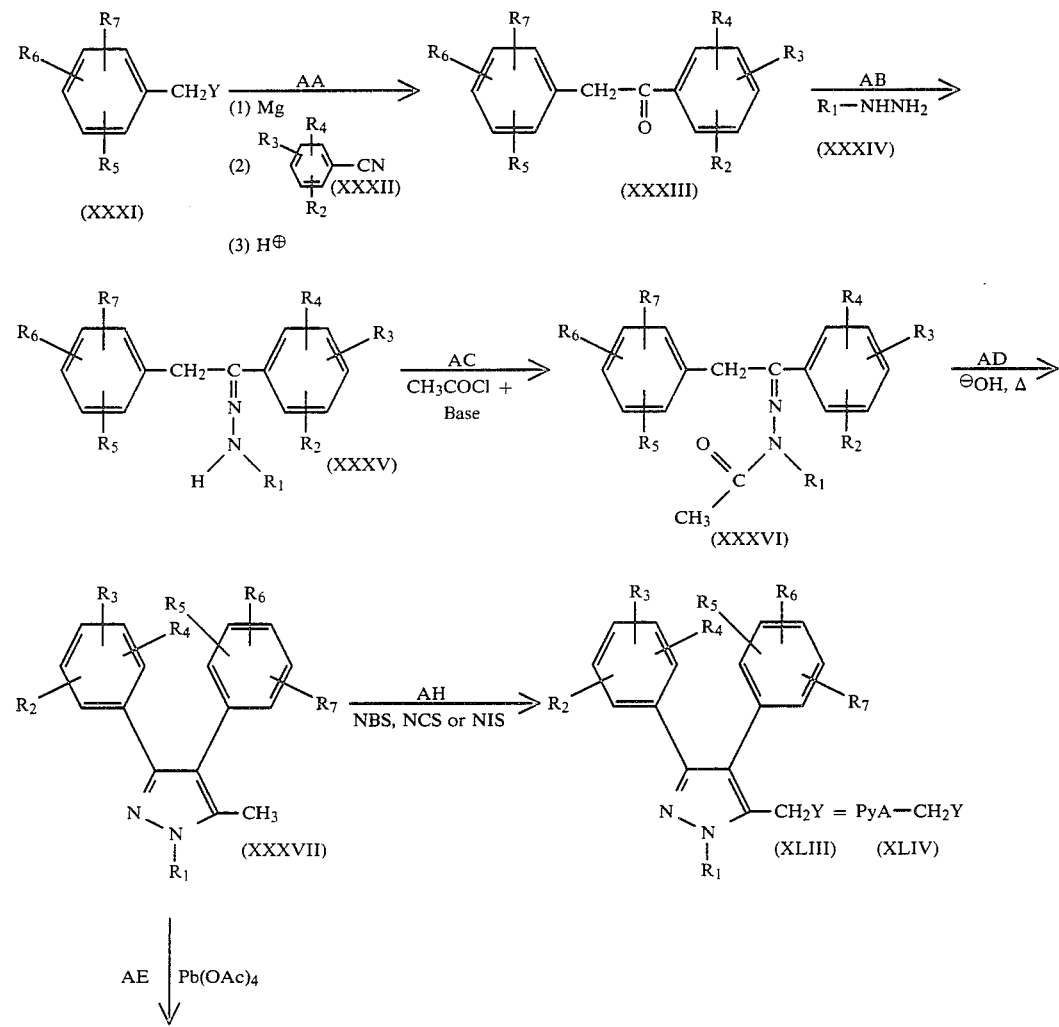

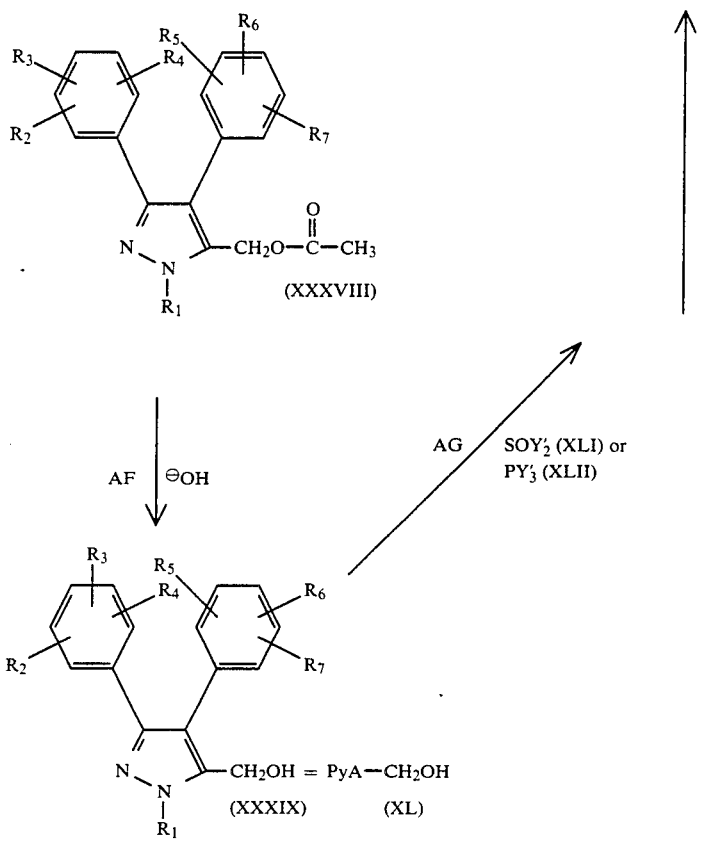
Reaction Scheme VI
The compounds of Formulae II and CCI wherein Py is PyB may be synthesized by the following series of reactions:
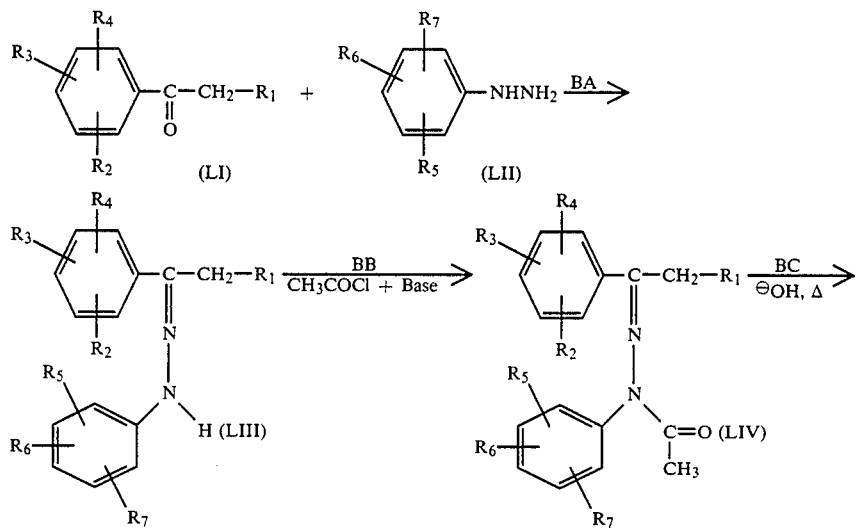

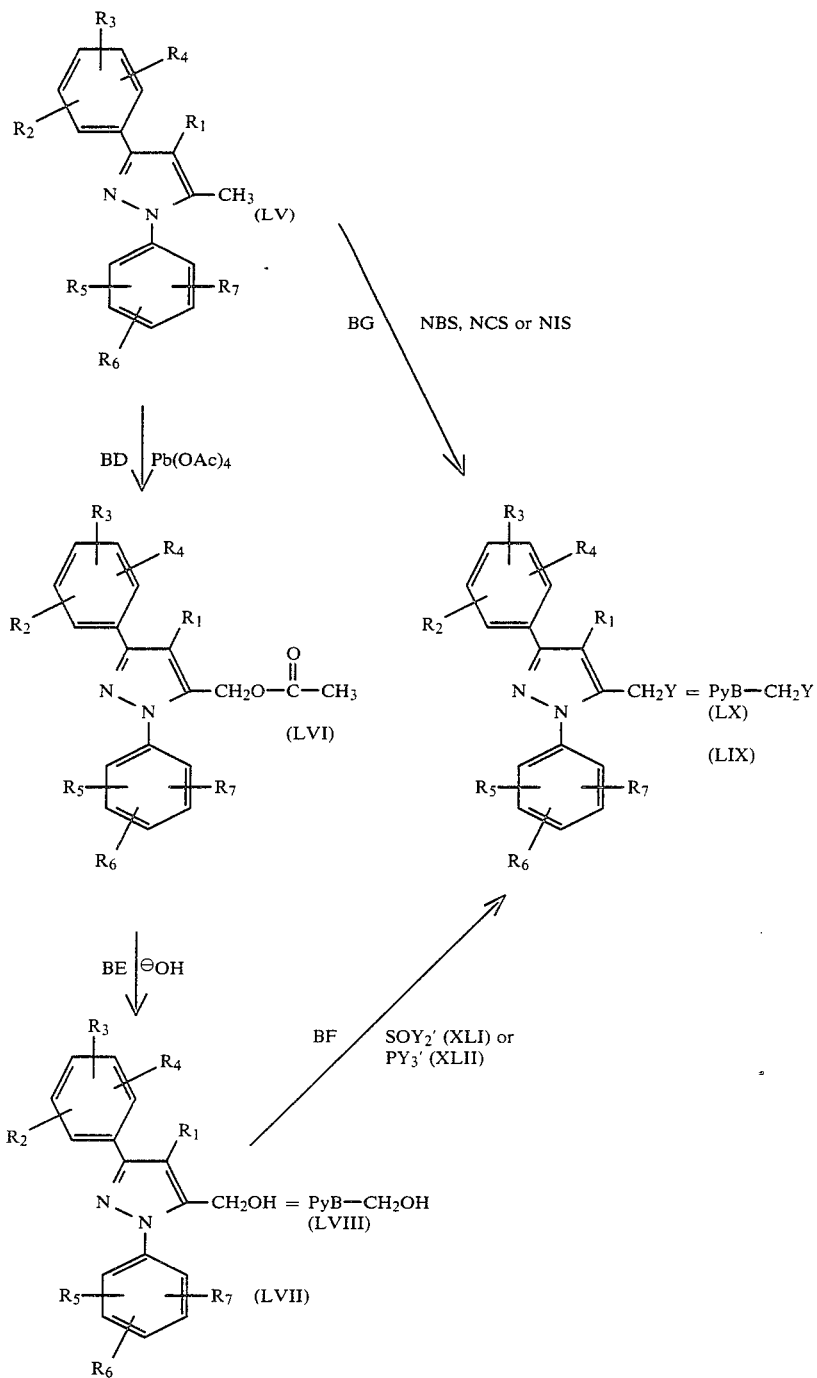
Reaction Scheme VII
The compounds of Formulae II and CCI wherein Py is PyC may be synthesized by the following series of reactions:
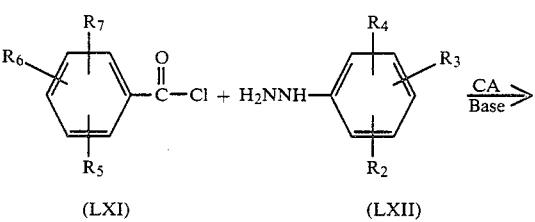

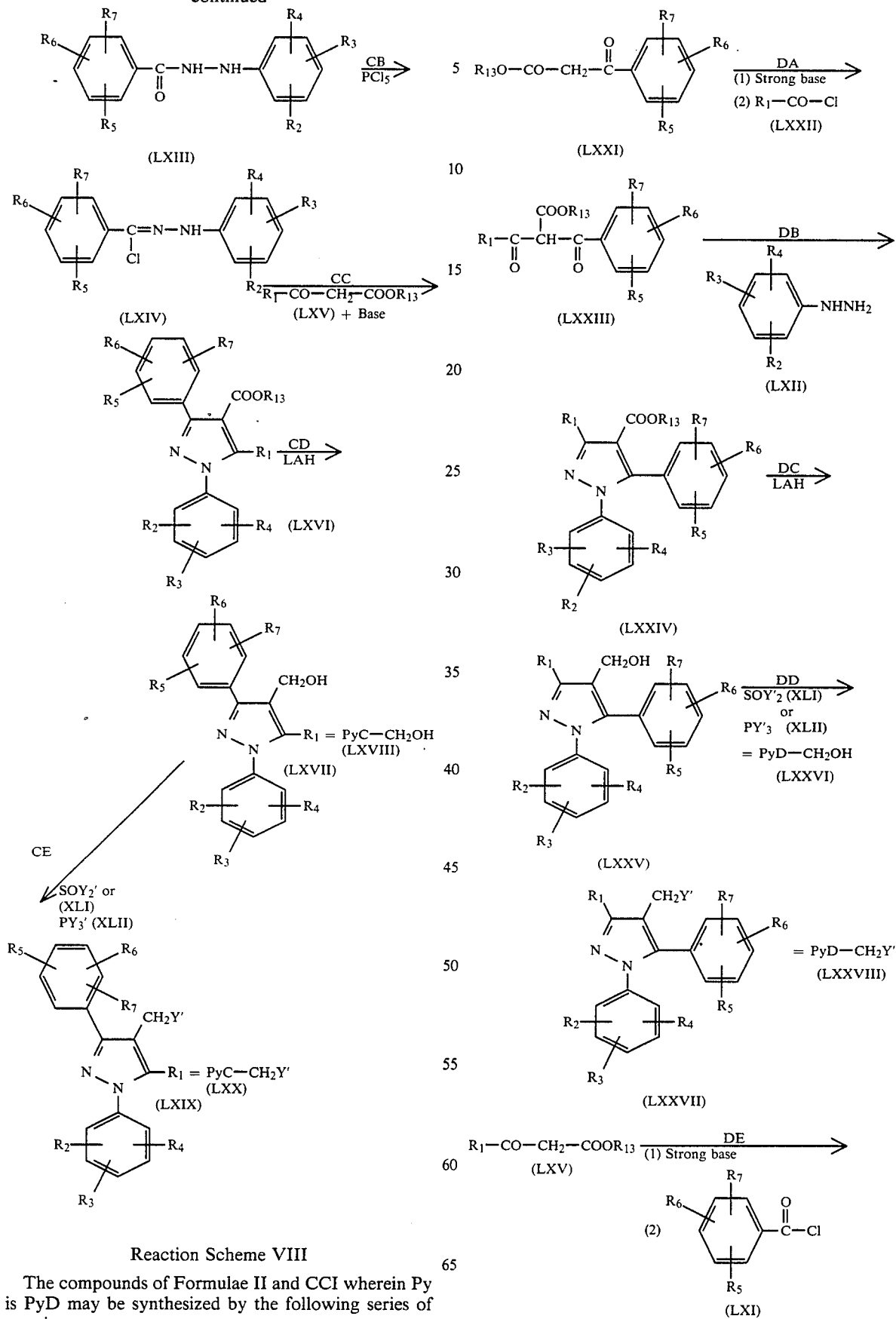
Reaction Scheme VIII
The compounds of Formulae II and CCI wherein Py is PyD may be synthesized by the following series of reactions:

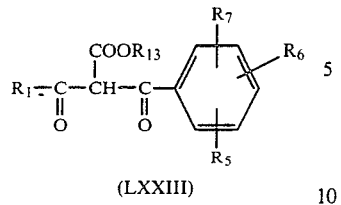
(LXXIII)
Reaction Scheme IX
The compound of Formula IV may be synthesized by the following series of reactions:
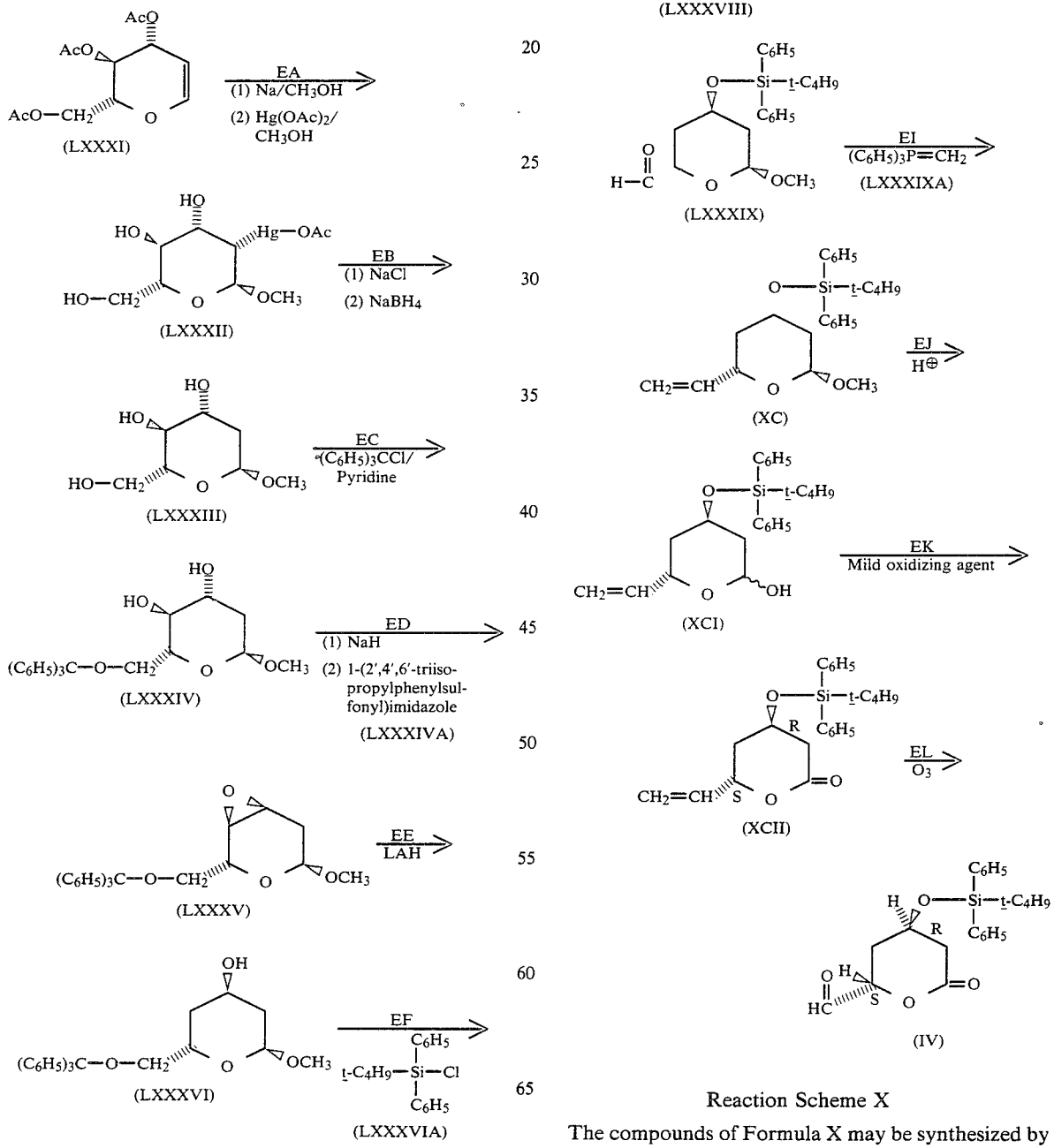
Reaction Scheme X
The compounds of Formula X may be synthesized by the following series of reactions:

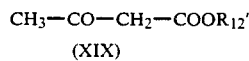
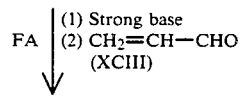
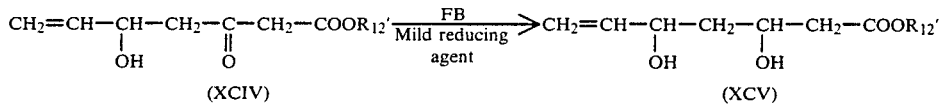
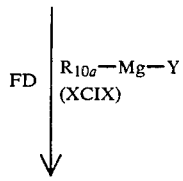
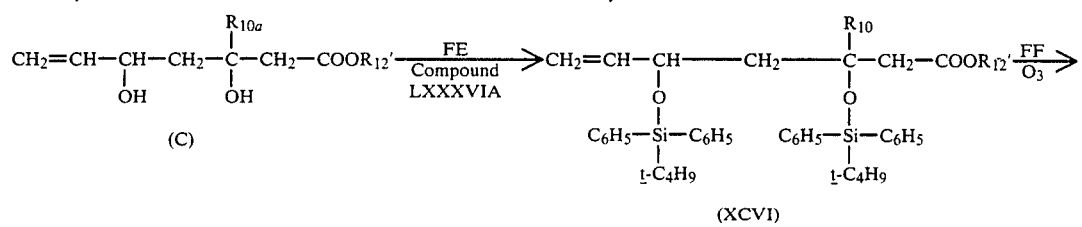
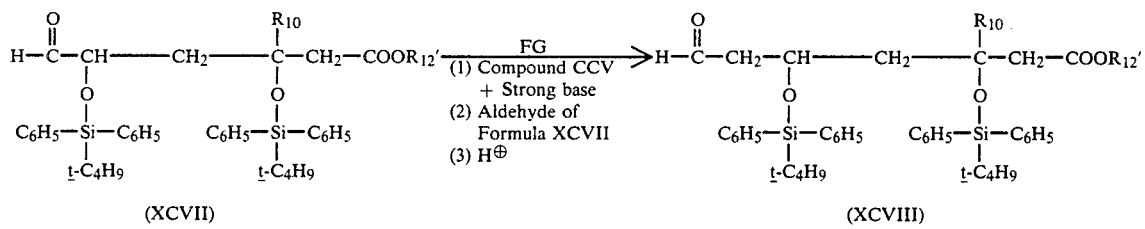
Reaction Scheme XI
The compounds of Formula XV wherein $X_5$ is —$(CH_2)_m$— or (E)—CH=CH and those of Formula IX wherein $X_1$ is —$CH_2CH_2$— may be synthesized by the following series of reactions:
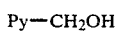
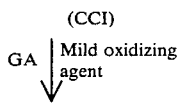
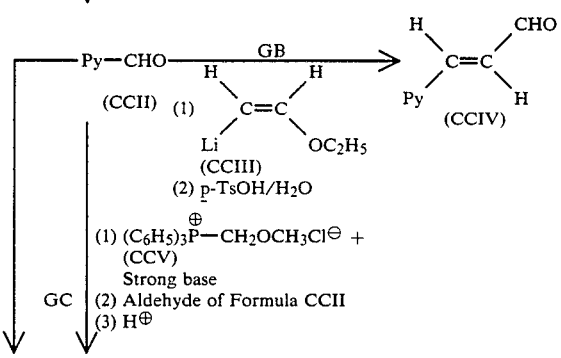

-continued

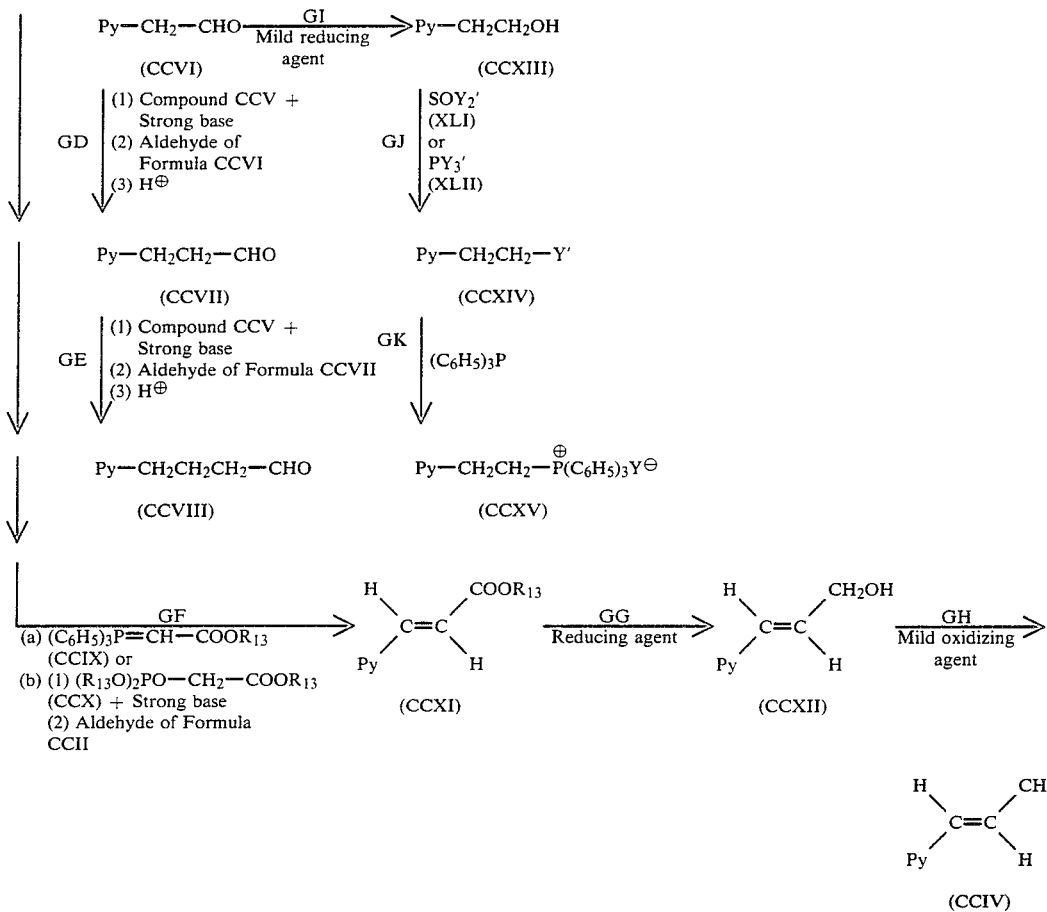

In the foregoing reaction schemes,
$R_{10a}$ is $C_{1-3}$alkyl, preferably methyl,
each $R_{13}$ is independently $C_{1-3}$alkyl, preferably n-$C_{1-3}$alkyl and most preferably $C_{1-2}$alkyl,
$R_{14}$ is $C_{1-2}$alkyl,
Py is

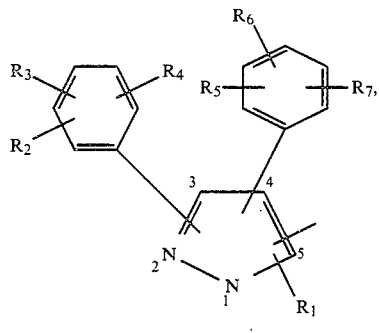

wherein $R_1$–$R_7$ are as defined above, with the provisos that (i) the free valence is in the 4- or 5-position of the pyrazole ring, and (ii) the $R_1$ group is ortho to the free valence,
PyA-PyD are as defined in Reaction Schemes V—VIII, respectively,
$X_1$ is —$CH_2$— or —$CH_2CH_2$—,
$X_2$ is a direct bond or —$CH_2$—,
$X_3$ is —CH=CH—, —CH=CH—$CH_2$— or —$CH_2$—CH=CH—, preferably (E)—CH=CH—, (E)—CH=CH—$CH_2$— or (E)—$CH_2$—CH=CH— and especially (E)—CH=CH—,
$X_4$ is —$CH_2CH_2$— or —$CH_2CH_2CH_2$—, especially —$CH_2CH_2$—,
$X_5$ is —$(CH_2)_m$— or (E)—CH=CH—, especially (E)—CH=CH—, wherein m is 0, 1, 2 or 3,
Y is chloro, bromo or iodo,
$Y^\ominus$ is chloride, bromide or iodide,
Y' is chloro or bromo,
$M_2^\oplus$ is sodium or potassium, and each of the other variables is as defined above.

| Reaction/Type | Reagents, Molar Ratios and Comments | Temperature | Time | Solvent | Inert Atmosphere |
|---|---|---|---|---|---|
| A | 1-1.3 moles triphenylphosphine per mole II | 60° C.-reflux, pref. ≦150° C., esp. 75°-90° C. | 0.5-24 hrs., pref. 0.75-2 hrs. | AIO, pref. HC such as benzene, toluene or xylene, or a mixture thereof | Yes |
| B (Wittig) | (1) 1-2 moles strong base, e.g., sodium hydride or pref. n-butyllithium (pref. as 1.3-1.7 M. solution in hexane), per mole III. Pref., slowly add n-butyllithium solution to solution of III. | −40°-5°C, pref. −35°-−20° C. | 5-60 min. | AIO, e.g., HC such as toluene or, pref., ES such as THF | Yes |
| | (2) 0.65-1.5 moles IV per mole III. The product (V) is a mixture of the (Z) and (E) (cis and trans, respectively) isomers which may be separated by chromatography. See, for example, Part d of Step 7 of Example 1. | −55°-25° C., pref. −35°-−5° C. | 0.75-18 hrs., pref. 1-4 hrs. | Same as Step 1 | Yes |
| C (Deprotection) | 1-4 moles, pref. 2-4 moles, fluoride reagent, esp. tetra-n-butylammonium fluoride, per mole V and 1-2 moles, pref. 1.2-1.5 moles, glacial acetic acid per mole fluoride reagent. First add glacial acetic acid to solution of V, then add fluoride reagent. | 20°-60° C., pref. 20°-25° C. | 2-30 hrs. | AIO, e.g., ES, pref. THF | — |
| D (Hydrogenation) | Excess hydrogen (more than 1 mole per mole V) and catalytic amount of platinum dioxide (e.g., 1-5 g. per mole V). Initial hydrogen pressure is conveniently 30-60 p.s.i. | 20°-25° C. | Until 1 mole hydrogen per mole V is taken up | Lower alkanol, e.g., ethanol | — |
| E (Deprotection) | Same as Reaction C (Molar quantities are per mole VII). | Same as C | Same as C | Same as C | — |
| F (Wittig) | Same as Reaction B. (Reactant in Step 2 is X.) The product (XI) is a mixture of the (Z) and (E) (cis and trans, respectively) isomers which may be separated by chromatography. See, for example, Part d of Step 7 of Example 1. | Same as B | Same as B | Same as B | Yes |
| G (Deprotection) | Same as Reaction C except utilize 2-8 moles, pref. 4-8 moles, fluoride reagent per mole XI. | Same as C | Same as C | Same as C | — |
| H (Hydrogenation) | Same as Reaction D (Molar quantities are per mole XI). | Same as D | Same as D | Same as D | — |
| I (Deprotection) | Same as Reaction C except utilize 2-8 moles, pref. 4-8 moles, fluoride reagent per mole XIII. | Same as C | Same as C | Same as C | — |
| J | (1) Generation of dianion of XIX: 1 mole XIX and 2-2.2 equivalents strong base, pref. 1-1.1 moles sodium hydride then 1-1.1 moles n-butyllithium or 2-2.2 moles lithium | −50°-10° C., pref. −20°-5° C. | 0.3-1.5 hrs., | AIO, e.g., ES, pref. THF | Yes |

| Reaction/Type | Reagents, Molar Ratios and Comments | Temperature | Time | Solvent | Inert Atmosphere |
|---|---|---|---|---|---|
| | diisopropylamide. n-butyllithium is preferably employed as a 1.3–1.7 M solution in hexane and lithium diisopropylamide is prepared in situ from n-butyllithium and diisopropylamine. | | | | |
| | (2) 1–2.5 moles, pref. 1.2–2.2 moles, more pref. 1.3–2.1 moles, of dianion of XIX (assuming 100% conversion of XIX to its dianion) per mole XV. Product (XX) is racemic. | −80°–0° C., pref. −50°–0° C., more pref. −30°–−10° C. | 0.3–4 hrs. pref. 0.3–1.5 hrs. | Same as Step 1 | Yes |
| K (Reduction) | (a) Non-stereoselective: 1–4, pref. 2–4, equivalents of transferable hydride per mole XX, pref. sodium borohydride or complex of t-butylamine and borane. When a racemic XX is utilized, product (XXI) is a mixture of all four possible stereoisomers (the erythro and threo racemates), the ratio of the threo racemate to the erythro racemate generally being 3:2 to 2:3. | −10°–30° C. | 1–8 hrs. | IO, e.g., lower alkanol, exp. ethanol | Yes |
| | (b) Stereoselective: (1) 1–2.2 moles, pref. 1.02–2 moles, tri-(primary or secondary C$_2$–$_4$alkyl)borane, pref. triethylborane or tri-n-butylborane, and, optionally, 0.5–8 liters, e.g., 0.75–6.5 liters, air (at 25° C. and 760 mm. Hg.) per mole XX. | 0°–50° C., pref. 0°–25° C. | 0.5–6 hrs., pref. 1–3.5 hrs. | AIO, pref. ES, esp. THF | — |
| | (2) 0.4–7.5 moles, pref. 2–5 moles, sodium borohydride per mole XX. After the reaction quench the reaction mixture with, for example, 10% hydrochloric acid and isolate the crude product by extracting with a suitable inert organic solvent (e.g., diethyl ether) and evaporating the solvent at reduced pressure. | −100°–−40° C., pref. −90°–−70° C. | 2–48 hrs., pref. 10–40 hrs. | Same as Step 1 | — |
| | (3) Large excess of anhydrous methanol, e.g., 50–100 moles per mole XX, or use mixture of methanol, hydrogen peroxide and aqueous phosphate buffer having a pH of 7–7.2. See Step 3 of Alternative b of Reaction FB. (c) Alternative stereoselective: | 20°–60° C., pref. 20°–30° C. | 0.2–5 hrs., pref. 0.5–4 hrs. | Neat | — |

| Reaction/Type | Reagents, Molar Ratios and Comments | Temperature | Time | Solvent | Inert Atmosphere |
|---|---|---|---|---|---|
| | (p) Preparation of zinc borohydride/diethyl ether: Add 1 mole zinc chloride to 5 l. anhydrous diethyl ether followed by 2 moles sodium borohydride. Stir for 16-18 hrs. and decant off the solution (a 0.15-0.2 M solution of zinc borohydride in diethyl ether). N.B. The solid should be decomposed very carefully. | 20°-25° C. | 16-18 hrs. | Anhydrous diethyl ether | Yes |
| | (1) 1 mole zinc borohydride (in form of solution produced in Step p) per mole XX | −80°- −50° C., pref. −80°- −75° C. | 0.5-5 hrs., pref. 1-2 hrs. | AIO, pref. ES, esp. diethyl ether or mixture of diethyl ether with another ES | Yes |
| | (2) Add excess methanol (e.g., 10-100 moles per mole XX) and allow to slowly warm to 20°-25° C. | −80°- −50° C., pref. −80°- −75° C., → 20°-25° C. | 1-2 hrs. | Same as Step 1 | — |
| | (3) Add excess dilute aqueous acetic acid to quench the reaction mixture | 20°-25° C. | — | Same as Step 1 | — |
| | When a racemic XX is utilized in Alternative b or c, product (XXI) is a mixture of the four possible stereoisomers wherein the ratio of the erythro isomers (racemate) to the threo isomers (racemate) is about 4-20:1, usually 5-15:1. Repeated recrystallization of the cyclic boron ester produced in Step 2 of Alternative b, if a solid, may raise the ratio or even yield pure erythro racemate and mother liquors enriched with the threo racemate from which pure threo racemate may be obtained. | | | | |
| L | (1) Generation of monoanion of XVI: 1-1.1 equivalents strong base, pref. lithium diisopropylamide, per mole XVI. | −80°- −40° C., pref. −80°- −75° C. | 0.25-1.5 hrs. | AIO, e.g., ES, pref. THF | Yes |
| | (2) 1-4 moles, pref. 3 moles, of monoanion of XVI (assuming 100% conversion of VI to its monoanion) per mole XV. Product (XVII) is a racemate. | −80°- −40° C., pref. −80°- −75° C. | 0.25-1.5 hrs. | Same as Step 1 | Yes |
| M (Acylation) | 1-3 moles, pref. 2 moles, XVIIA or XVIIB per mole XVII. When an ES is used as the solvent, also use 1-4 moles, pref. 2.5-3 moles, of a tertiary amine, e.g., pyridine or, pref., 4-dimethylaminopyridine, per mole XVII. | −10°- −50° C., pref. 20-30° C. | 2-18 hrs., pref. 4-12 hrs. | Pyridine or anhydrous ES, pref. THF | Yes |
| N | (1) Generation of monoanion of XVIID: 1-1.1 equivalents strong base, pref. lithium diisopropylamide, per mole XVIID. | −80°-0° C. | 0.25-1 hr. | AIO, e.g., ES, pref. THF | Yes |
| | (2) 1-4 moles, pref. 3 moles, of monoanion of XVIID (assuming 100% conversion of XVIID to its monoanion) per mole XVIIC. | −80°- −40° C., pref. −80°- −70° C. | 0.25-1.5 hrs. | Same as Step 1 | Yes |

| Reaction/Type | Reagents, Molar Ratios and Comments | Temperature | Time | Solvent | Inert Atmosphere |
|---|---|---|---|---|---|
| NA (Hydrolysis) | 2-2.3 moles, pref. 2-2.2 moles, XXIII per mole XVIIE. | 0° C.-reflux, pref. 0°-75° C., esp. | 1-4 hrs. | Inert aqueous organic, e.g., water and lower alkanol, pref. mixture of water and methanol or, esp., ethanol | — mixture of |
| O (Hydrolysis) | 1-1.3 equivalents XXIII per mole XXII or, if it is desired to isolate XXIV, 0.95-0.99 equivalents XXIII per mole XXII. | 0° C.-reflux, pref. 0°-75° C., esp. 20°-70° C. | 1-4 hrs. | Inert aqueous organic, e.g., mixture of water and lower alkanol, pref. mixture of water and methanol or, esp., ethanol | — |
| P (Acidification) | At least 1 equivalent, e.g., 1-1.25 equivalents, acid, e.g., 2N. hydrochloric acid, per mole XXIV. | 0°-25° C. | 1-5 min. | Water or mixture of water and water-miscible inert organic solvent, e.g., methanol, ethanol, diethyl ether or THF | — |
| Q (Esterification) | At least 2 moles, e.g., 2-10 moles, pref. 2.05-2.5 moles, XXVIII per mole XXX. | 0°-70° C., pref. 20°-25° C. | 2-12 hrs. | IO, e.g., ES such as THF or alcohol of the formula $R_{12}$—OH ($R_{12}$ same as in XXXVIII), if a liquid | — |
| R (Neutralization) | 0.95-0.99 equivalents, pref. 0.96-0.98 equivalents, XXVI per mole XXV. | 0°-25° C., pref. 20°-25° C. | 2-10 min. | Same as O | — |
| S (Lactonization) | (a) Use of catalytic amount of strong acid such as p-toluenesulfonic acid is pref. but usually omit. Use of Dean-Stark apparatus is pref. if solvent forms azeotrope with water. (b) 1-1.5 moles of a lactonization agent, e.g., a carbodiimide, pref. a water-soluble carbodiimide such as N—cyclohexyl-N'—[2'-(N''—methylmorpholinium)-ethyl]carbodiimide p-toluenesulfonate per mole XXV. Alternative b often results in higher yields of XXX than Alternative a. Racemic erythro XXV yields racemic trans (lactone) XXX, racemic threo XXV yields racemic cis (lactone) XXX, mixture of racemic erythro and threo XXV yields mixture of racemic trans and cis (lactones) XXX and single enantiomer of XXV yields single enantiomer of XXX, e.g., 3R,5S | 75° C.-reflux, pref. 75°-150° C., esp. 80°-120° C. 10-35° C., pref. 20°-25° C. | 3-18 hrs., pref. 4-7 hrs. 2-8 hrs., pref. 3-4 hrs. | AIO, pref. HC, e.g., benzene, toluene or xylene or mixture thereof AIO, pref. HLA, esp. methylene chloride | — |

-continued

| Reaction/Type | Reagents, Molar Ratios and Comments | Temperature | Time | Solvent | Inert Atmosphere |
|---|---|---|---|---|---|
| T (Hydrolysis) | erythro XXV yields 4R,6S trans XXX. 1–1.3 equivalents XXIII per mole XXX or, if it is desired to isolate XXIV, 0.95–1 equivalent, preferably 0.97–0.99 equivalent, XXIII per mole XXX. Racemic trans (lactone) XXX yields racemic erythro XXIV, racemic cis (lactone) XXX yields racemic threo XXIV, mixture of racemic trans and cis (lactones) XXX yields mixture of racemic erythro and threo XXIV and single enantiomer of XXX yields single enantiomer of XXIV, e.g., 4R,6S trans XXX yields 3R,5S erythro XXIV. | 0° C.-reflux, pref. 0°–75° C., more pref. 20°–75° C., esp. 40°–60° C. | 1–6 hrs., pref. 1–4 hrs. | Same as O | — |
| AA (Grignard) | (1) 0.9–1 mole magnesium turnings per mole XXXI. Pref., slowly add magnesium turnings to solution of XXXI at rate such that the reaction mixture refluxes gently. | 10° C.-reflux, pref. 30°–38° C. | Until magnesium completely dissolves, e.g., 0.5–2 hrs. | Anhydrous inert ES, esp. diethyl ether or THF | Yes |
| | (2) 1–2 moles, pref. 1.2–1.5 moles, Grignard reagent (produced in Step (1) per mole XXXII. | 10° C.-reflux, pref. 20°–40° C., esp. 20°–25° C. | 2–20 hrs., pref. 3–5 hrs. | Same as Step 1 | Yes |
| (Hydrolysis) | (3) Excess aqueous inorganic acid, e.g., 10% hydrochloric acid. Pref., pour ice cold aqueous inorganic acid into solution resulting from Step 2 stirred at 0°–25° C. | 0°–25° C. | 1–30 min., e.g., 1–5 min. | Inert aqueous organic, pref. mixture of water and solvent utilized in Steps 1 and 2 | — |
| AB | 1–3 moles, pref. 1.5–2.5 moles, XXXIV and a catalytic amount (e.g., 0.05–0.5 moles) acetic acid per mole XXXIII. | 60°–100° C., pref. 70°–90° C. | 1–4 hrs, pref. 1.25–3 hrs. | IO optionally containing a small amount (≦10%) of water, pref. a lower alkanol such as methanol or ethanol, e.g., 95% ethanol | — |
| AC (Acylation) | 1–1.8 moles, pref. 1.1–1.5 moles, acetyl chloride and 1–3 moles, pref. 1.5–2 moles, of a tertiary amine, e.g., a tri(C$_1$–$_3$alkyl)amine, pref. triethylamine, per mole XXXV, (at least one mole tertiary amine per mole acetyl chloride). Commence reaction at 0°–5° C. and allow temperature to gradually rise to 20°–25° C. as reaction proceeds. | 0°–25° C. | 1–3 hrs. | AIO, e.g., HC such as benzene or toluene or ES, pref. THF | — |
| AD (Cyclization) | 2–6 moles sodium hydroxide or, | 50°–90° C., pref. | 3–10 hrs. | AIO, e.g., | Yes |

-continued

| Reaction/Type | Reagents, Molar Ratios and Comments | Temperature | Time | Solvent | Inert Atmosphere |
|---|---|---|---|---|---|
| | preferably, potassium hydroxide per mole XXXVI. Can commence reaction at 70°-80° C. and, after 2-3 hrs, allow reaction mixture to cool to 20°-25° C. and stir at this temperature for 8-24 hrs. | 70°-80° C. | | higher boiling ES, pref. bis-(2-methoxyethyl)-ether or bis-(2-ethoxyethyl)-ether | |
| AE | 1-1.1 moles lead tetraacetate per mole XXXVII. | 20°-80° C. | 8-15 hrs. | Glacial acetic acid or benzene | Yes |
| AF (Hydrolysis) | 1-1.5 equivalents, pref. 1.1-1.3 equivalents, sodium hydroxide or potassium hydroxide per mole XXXVIII. | 20°-50° C. | 3-5 hrs. | Same as O | — |
| AG (Halogenation) | 1-2 moles, pref. 1.5-1.8 moles, XLI or XLII per mole XXXIX. Y in product is Y'. | −10°-80° C. | 2-18 hrs. | AIO, pref. ES, e.g., diethyl ether or THF, HLA, e.g., methylene chloride, or HC, e.g., benzene | — |
| AH (Halogenation) | 1-1.5 moles, pref. 1.1-1.3 moles, N—bromo-, N—chloro- or N—iodo-succinimide and catalytic amount of an organic peroxide, e.g., di-benzoyl peroxide. | 50°-100° C., pref. 70°-90° C. | 0.5-1.5 hrs., pref. 0.6-1 hr. | AIO, pref. HLA, esp. carbon tetrachloride | Yes |
| BA | 1-3 moles, pref. 1.1-1.5 moles, LII and a catalytic amount of acetic acid (e.g., 0.05-0.5 mole) per mole LI. | Same as AB | Same as AB | Same as AB | Yes |
| BB (Acylation) | Same as Reaction AC. (Molar quantities are per mole LIII). | Same as AC | Same as AC | Same as AC | — |
| BC (Cyclization) | Same as Reaction AD. (Molar quantities are per mole LIV). | Same as AD | Same as AD | Same as AD | Yes |
| BD | Same as Reaction AE. (Molar quantities are per mole LV). | Same as AE | Same as AE | Same as AE | Yes |
| BE (Hydrolysis) | Same as Reaction AF. (Molar quantities are per mole LVI). | Same as AF | Same as AF | Same as AF | — |
| BF (Halogenation) | Same as Reaction AG. (Molar quantities are per mole LVII). | Same as AG | Same as AG | Same as AG | — |
| BG (Halogenation) | Same as Reaction AH. (Molar quantities are per mole LV). | Same as AH | Same as AH | Same as AH | Yes |
| CA (Acylation) | 1-1.01 moles LXI and 1-2 moles of a tertiary amine, e.g., a tri($C_1$-alkyl)-amine, pref. triethylamine, per mole LXII (at least one mole tertiary amine per mole LXI). Commence reaction at −10°-0° C. and allow temperature to gradually rise to 20°-25° C. as reaction proceeds. | −10°-0° C. → 20°-25° C. | 2-4 hrs. | AIO, e.g., ES, pref. diethyl ether or THF | — |
| CB | 1-1.5 moles, pref. 1.2 moles, phosphorus pentachloride per mole LXIII. | 30°-40° C., pref. 35° C. | 8-16 hrs., pref. 10-14 hrs. | AIO, e.g., ES, pref. diethyl ether | Yes |
| CC | 1-1.05 moles LXV and 1-1.05 | 20°-25° C. | 3-6 hrs. | Anhydrous lower | Yes |

-continued

| Reaction/Type | Reagents, Molar Ratios and Comments | Temperature | Time | Solvent | Inert Atmosphere |
|---|---|---|---|---|---|
| CD (Reduction) | moles base, pref. sodium ethoxide, per mole LXIV. 0.5–3.2 moles, pref. 0.75–3 moles, lithium aluminum hydride per mole LXVI. Pref. commence at −5°–5° C. and allow reaction mixture to warm to 20°–25° C. as reaction proceeds. | −5°–25° C., pref. −5°–5° C. → 20°–25° C. | pref. 4 hrs. 2–6 hrs., pref. 2–4 hrs. | alkanol, pref. absolute ethanol AIO, e.g., ES, pref. diethyl ether | Yes |
| CE (Halogenation) | Same as Reaction AG. (Molar quantities are per mole LXVII). | Same as AG | Same as AG | Same as AG | — |
| DA | (1) 2–2.2 moles strong base, pref. sodium hydride, per mole LXXI. (2) 1–2 moles, pref. 1.5–1.7 moles, LXXII per mole LXXI. Add LXXII dropwise (if a liquid) or as a solution in the reaction solvent to the solution of the anion produced in Step 1 at −5°–5° C., stir for 5–30 min., allow temperature to slowly rise to 20°–25° C. and stir at this temperature for the balance of the reaction time. | −5°–5° C. −5°–5° C. → 2.5–4 hrs. 20°–25° C. | 0.5–1 hr. Same as Step 1 | AIO, pref. ES, esp. THF Yes | Yes |
| DB (Cyclization) | 1–2.2 moles, pref. 1.5 moles, LXII per mole LXXIII. Product may be a mixture of LXXIV and LXVI, with the former usually being the major product. The relative amounts of the two compounds depends upon, among other things, the significance of R₁ and the significances and positions of R₂–R₇. The mixture may be separated by conventional means. | 20°–40° C., pref. 20°–25° C. | 12–24 hrs. | Glacial acetic acid or dimethyl sulfoxide | Yes |
| DC (Reduction) | Same as Reaction CD. (Molar quantities are per mole LXXIV). | Same as CD | Same as CD | Same as CD | Yes |
| DD (Halogenation) | Same as Reaction AG. (Molar quantities are per mole LXXV). | Same as AG | Same as AG | Same as AG | — |
| DE | Same as Reaction DA. (Molar quantities are per mole LXV). | Same as DA | Same as DA | Same as DA | Yes |
| EA | (1) Catalytic amount of sodium, e.g., 0.026 mole per mole LXXXI. Add sodium to methanol, stir for 15 min., add LXXXI portionwise over 15 min. period and stir for 1 hr. (2) 1–1.01 moles mercuric acetate per mole LXXXI. | 20°–25° C. | 1.5 hrs. | Methanol | Yes |
| EB | (1) 1.55–1.6 moles sodium chloride per mole LXXXII. | 20°–25° C. | 5 hrs. | Methanol | Yes |
| | | 20°–25° C. | 30 min. | Methanol | Yes |
| | (2) 1–1.1 moles, esp. 1.08 moles, sodium borohydride per mole LXXXII. Add sodium borohydride portionwise over 1.5 hr. period at 0°–5° C. adding isopropanol after | −5°–0° C. → 20°–25° C. | 5 hrs. | 3:2 mixture of methanol and isopropanol | Yes |

| Reaction/Type | Reagents, Molar Ratios and Comments | Temperature | Time | Solvent | Inert Atmosphere |
|---|---|---|---|---|---|
| EC (Etherification) | each portion (in amounts such that final solvent is 3:2 mixture of methanol and isopropanol) and stir at 20°-25° C. for 3.5 hours. 0.8-1 mole, pref. 0.84 mole, triphenylmethyl chloride per mole LXXXIII. Add triphenylmethyl chloride portionwise over 15 min. period at 20°-25° C. and stir at 20°-25° C. for 1 hr. and at 35°-40° C. for 30-31 hrs. | 35°-40° C. | 30-32 hrs. | 10-15:1, pref. 12-14:1, mixture of pyridine and methylene chloride | Yes |
| ED | (1) 4-5 moles, pref. 4.75 moles, sodium hydride per mole LXXXIV. Over 30 min. period add solution of LXXXIV in THF to sodium hydride stirred in THF (some cooling is necessary to maintain temperature at 25°-30° C.) and stir at 20°-25° C. for 3 hrs. | 20°-30° C. | 3.5 hrs. | Hexamethylphosphoramide or, pref., dry THF | Yes |
|  | (2) 1 mole of LXXXIVA per mole LXXXIV. Over 30 min. period add solution of LXXXIVA to reaction mixture stirred at −30° C. and allow reaction mixture to slowly warm to 20°-25° C. over 2 hr. period. | −30° C. → 20°-25° C. | 2.5 hrs. | Same as Step 1 | — |
| EE (Reduction) | 1.8-1.9 moles, pref. 1.85 moles, lithium aluminum hydride per mole LXXXV. Over 1.5 hr. period add lithium aluminum hydride to solution of LXXXV stirred at −10°-0° C. and stir at −10°-10° C. for 15-17 hrs. | −10°-10° C. | 16.5-18.5 hrs. | Dry methyl t-butyl ether or diethyl ether | Yes |
| EF (Silylation) | 1-2 moles, pref. 1.1 moles, LXXXVIA per mole LXXXVI and 2 moles imidazole per mole LXXXVIA. Add LXXXVIA to solution of LXXXVI and imidazole over 30 min. period (maintain maximum temperature of 32° C.) and stir for 15.5-18.5 hrs. at 20°-25° C. | 20°-32° C. | 16-19 hrs. | Dry dimethylformamide | Yes |
| EG (Hydrolysis) | 125-130 ml. 70% (v/v) aqueous trifluoroacetic acid per mole LXXXVII. Over 1 hr. period add aqueous trifluoroacetic acid dropwise to solution of LXXXVII stirred at −55°-−50° C., allow to warm to −10° C. over 1 hr. period and stir at −10°-0° C. for 3 hrs. | −55°-−50° C. → −10°-0° C. | 5 hrs. | Methylene chloride | Yes |
| EH (Oxidation) | 2 moles pyridinium chlorochromate or 6-10 moles, pref. 8 moles, chromium trioxide (pref. complexed with pyridine, more pref. 2 moles pyridine per mole chromium trioxide) and 700-1000 g. crushed molecular sieves (pref. 4Å. size) per mole LXXXVIII. When pyridinium chlorochromate is used, add it portionwise over 15-30 min. period to balance of reaction mixture, and when chromium trioxide is used, add solution of LXXXVIII to balance of reaction mixture over 15-30 min. period and, in each | 20°-25° C. | 2.25-3.5 hrs. | Dry methylene chloride | Yes |

| Reaction/Type | Reagents, Molar Ratios and Comments | Temperature | Time | Solvent | Inert Atmosphere |
|---|---|---|---|---|---|
| EI (Wittig) | case, stir for 2-3 hrs.<br>(p) Synthesis of LXXXIXA: 1 mole methyl-triphenylphosphonium bromide or, pref., iodide and 1-1.03 moles n-butyllithium. Add solution of n-butyllithium, pref. 1.3-1.7 M. in hexane, dropwise over 10-20 min. period to slurry of phosphonium compound and stir for 1 hr.<br>(1) 1-1.5 moles, pref. 1.1-1.45 moles, LXXXIXA per mole LXXXIX. Add solution of LXXXIX in dry THF dropwise over 30 min. period to product of Step p stirred at $-10°$-$-10°$ C., allow reaction mixture to warm to $20°$-$25°$ C. and stir for balance of reaction time. | $-30°$-$-25°$ C., pref. $-5°$-$-5°$ C. | 1.16-1.33 hrs. | Dry THF | Yes |
| EJ (Hydrolysis) | Heat XC in large excess of the solvent. Pref., quantity of solvent is such that reaction mixture contains 40-60 moles acetic acid per mole XC. | $-10°$-$10°$ C., pref. $-5°$-$-5°$ C. $\to$ $20°$-$25°$ C.<br><br>$60°$-$70°$ C. | 16-19 hrs.<br><br>2-3 hrs. | Dry THF<br><br>Mixture of glacial acetic acid, THF and water, pref. a 3:2:2 mixture | Yes<br><br>— |
| EK (Oxidation) | 2-4 moles pyridinium chlorochromate per mole XCI. | $20°$-$25°$ C. | 16-24 hrs., pref. 17-19 hrs. | Dry methylene chloride | — |
| EL (Ozonolysis) | Excess ozone. Bubble ozone through solution of XCII until a bluish coloration persists and then quench reaction mixture with dimethyl sulfide or triphenylphosphine. | $-80°$-$-70°$ C., perf. $-78°$ C. | 2-30 min. | $C_{1-3}$alkanol, esp. methanol, or HLA, esp. methylene chloride, or ethyl acetate | — |
| FA | (1) Generation of dianion of XIX: 1 mole XIX and 2-2.2 equivalents strong base, e.g., 2-2.2 moles lithium diisopropylamide or, pref., 1-1.1 moles sodium hydride followed by 1-1.1 moles n-butyllithium (pref. as 1.3-1.7 M. solution in hexane).<br>(2) 1-1.2 moles dianion of XIX (assuming 100% conversion of XIX to its dianion) per mole XCIII. Slowly add solution of XCIII in, pref., dry THF to solution of dianion stirred at $-80°$-$0°$ C., pref. $-40°$-$-20°$ C., esp. $-35°$-$-30°$ C., stir at same temperature for 30 min. and allow to warm to $20°$-$25°$ C. over a 2 hr. period. Product (XCIV) is a racemate. | $-50°$-$-10°$ C., pref. $-10°$-$10°$ C. | 0.3-1.5 hrs., pref. 0.5-1 hr.<br><br>2.5 hrs. | AIO, e.g., ES, pref. THF<br><br>Same as Step 1 | Yes<br><br>Yes |
| FB (Reduction) | (a) Non-stereoselective: Same as Reaction K, Altenative a (Molar quantities are per mole of XCIV). Product (XCV) is a mixture of all four possible stereoisomers (the erythro and threo racemates), the erythro to threo ratio being approximately 3:2 | Same as K, a | Same as K, a | Same as K, a | Yes |

| Reaction/Type | Reagents, Molar Ratios and Comments | Temperature | Time | Solvent | Inert Atmosphere |
|---|---|---|---|---|---|
| | to 2.3.<br>(b) Stereoselective:<br>(1) 1–1.25 moles, pref. 1.05–1.25 moles, esp. 1.2–1.25 moles, tri-(primary or secondary C$_2$–4alkyl)borane, pref. triethylborane or tri-n-butylborane, esp. the latter, per mole XCIV. Use of air as in Step 1 of Alternative b of Reaction K is optional. | 0°–50° C., pref. 20°–25° C. | 1–6 hrs., pref. 1.5–3 hrs. | AIO, pref. ES, esp. THF | — |
| | (2) 0.4–1.5 moles, pref. 1–1.25 moles, sodium borohydride per mole XCIV. After the reaction, reaction mixture is quenched with, for example, 10% hydrochloric acid and crude product is isolated by extraction with, for example, diethyl ether and evaporation of the solvent. | −100°–−40° C., pref. −90°–−70° C., esp. −90°–−78° C. | 2–60 hrs., pref. 24–48 hrs. | Same as Step 1 | — |
| | (3) Large excess of methanol (e.g., 50–100 moles per mole XCIV) or mixture of methanol (e.g., 10–20 l. per mole XCIV), hydrogen peroxide (e.g., 4–8 l. of 30% aqueous hydrogen peroxide per mole XCIV) and a pH 7–7.2 aqueous phosphate buffer (pref. 6–10 l. of a pH 7 aqueous phosphate buffer (e.g., 0.054 M. sodium, 0.024 M. potassium and 0.047 M. phosphate) per mole XCIV). The amount of buffer must be sufficient to maintain a pH of 7–7.2. Dissolve product of Step 2 in methanol and add buffer and aqueous hydrogen peroxide. Use of methanol alone is preferred. | 0°–25° C., pref. 0°–10° C., when using a mixture of methanol, hydrogen peroxide and buffer and 20°–60° C. when using methanol alone | 0.7–5 hrs., pref. 2–4 hrs. | As indicated | — |
| | (c) Alternative stereoselective: Same as Reaction K, Alternative c | Same as K, c | Same as K, c | Same as K, c | Same as K, c |
| FC (Silylation) | 2–8 moles, pref. 4 moles, LXXXVIA per mole XCV and 2 moles imidazole per mole LXXXVIA. Slowly add LXXXVIA to solution of XCV and imidazole (at rate such that temperature does not exceed 30° C.) and stir at, pref., 20°–25° C. for balance of reaction time. | 20°–30° C., pref. 20°–25° C. | 16–19 hrs. | Dry dimethyl-formamide | Yes |
| FD (Gridnard) | (1) 1.8–2.1 moles, pref. 2 moles, XCIX per mole XCIV. | −70°–25° C., pref. −50°–0° C. | 1–15 hrs., pref. 2–8 hrs. | AIO, pref. ES, esp. THF | Yes |
| | (2) Quench with, for example, saturated ammonium chloride solution. | −20°–25° C. | 5–15 min. | — | — |
| FE (Silylation) | Same as Reaction FC (Molar quantities of LXXXVIA are per mole C). | Same as FC | Same as FC | Same as FC | Yes |
| FF (Ozonolysis) | Same as Reaction EL. | Same as EL | Same as EL | Same as EL | — |
| FG (Wittig) | Same as Reaction GC (Molar quantities are per mole XCVII). | Same as GC | Same as GC | Same as GC | — |

-continued

| Reaction/Type | Reagents, Molar Ratios and Comments | Temperature | Time | Solvent | Inert Atmosphere |
|---|---|---|---|---|---|
| GA (Oxidation) | 1-3.5 moles, pref. 1.2-3 moles, pyridinium chlorochromate or pyridinium dichromate, 5-10 moles, pref. 6-8 moles, chromium trioxide (pref. complexed with pyridine, more pref. 2 moles pyridine per mole chromium trioxide) or 5-50 moles, pref. 10-20 moles, manganese dioxide, pref. activated manganese dioxide, per mole CCI. | 20°-30° C., pref. 20°-25° C. | 2-18 hrs., pref. 3-12 hrs., with pyridinium chlorochromate or chromium trioxide, 8-24 hrs., pref. 15-18 hrs., with pyridinium dichromate and 4-48 hrs., pref. 10-24 hrs., with manganese dioxide | AIO, pref. HLA, exp. methylene chloride, for pyridinium chlorochromate, chromium trioxide or pyridinium dichromate and pref. HLA or ES, esp. diethyl ether, for manganese dioxide | Yes |
| GB | (p1) Preparation of cis-1-ethoxy-2-tri-n-butylstannylethylene: 1 mole ethoxyacetylene and 1 mole tri-n-butyltin hydride. Add ethoxyacetylene to tri-n-butyltin hydride at 50° C. over 1 hr. period and stir at 50°-55° C. for 3 hrs. and at 60°-70° C. for 1 hr. (p2) Preparation of CCIII: 1-1.08 moles n-butyllithium and 1 mole cis-1-ethoxy-2-tri-n-butylstannylethylene. Add n-butyllithium (pref. as 1.3-1.7 M. solution in hexane) dropwise to solution of stannyl compound at −78° C. | 50°-55° C. for 4 hrs. and 60°-70° C. for 1 hr.<br><br>−80°-−75° C. | 5 hrs.<br><br><br><br><br><br><br>1-3 hrs., pref. 2 hrs. | Neat<br><br><br><br><br><br><br>AIO, e.g., ES, pref. THF | Yes<br><br><br><br><br><br><br>Yes |
| (Addition) | (1) 1-1.15 moles CCIII (assuming 100% yield from Step p2) per mole CCII. Crude enol ether product of this step may be used in next step without isolation and/or purification but isolation and purification of enol ether intermediate may improve yield of CCIV from next step. | −80°-−40° C., pref. −80°-−60° C. | 1-8 hrs., pref. 1.5-5 hrs. | Same as Step (p2) | Yes |
| (Hydrolysis) | (2) Catalytic amount of p-toluenesulfonic acid or monohydrate thereof (e.g., 0.5-2 g., pref. 1.2-1.8 g., per mole CCII used in Step 1) and water. | 20°-40° C., pref. 20°-25° C. | 1-5 hrs., pref. 1.5-4 hrs. | Mixture of ES and water, pref. mixture of THF and water | — |
| GC (Wittig) | (1) Synthesis of ylide: 1-1.05 moles strong base, e.g., sodium hydride, phenyllithium or, pref., n-butyllithium (esp. as 1.3-1.7 M. solution in hexane) per mole CCV. Pref. slowly add solution of strong base to solution of CCV. | −40°-0° C., pref. −35°-−20° C. | 1-4 hrs. | AIO, pref. ES, e.g., THF | Yes |

-continued

| Reaction/Type | Reagents, Molar Ratios and Comments | Temperature | Time | Solvent | Inert Atmosphere |
|---|---|---|---|---|---|
| | (2) Synthesis of enol ether: Ylide from 1–1.05 moles CCV per mole CCII. | −30°–0° C., pref. −20°–0° C. | 1–4 hrs. | Same as Step 1 | Yes |
| | (3) Hydrolysis of enol ether: Large molar excess, e.g., 2–20 moles, strong acid, e.g., 70% perchloric acid, per mole CCII used in Step 2. | 0°–30° C. | 8–24 hrs. | Mixture of aqueous acid an ES, e.g., mixture of 70% perchloric acid and THF | — |
| GD (Wittig) | Same as Reaction GC (Molar quantities in Steps 2 and 3 are per mole CCVI). | Same as GC | Same as GC | Same as GC | Same as GC |
| GE (Wittig) | Same as Reaction GC (Molar quantities in Steps 2 and 3 are per mole CCVII). | Same as GC | Same as GC | Same as GC | Same as GC |
| GF (Wittig) | Alternative a: 1–2 moles, pref. 1–1.7 moles, CCIX per mole CCII. | 80° C.–reflux, esp. refluxing toluene | 6–18 hrs. | AIO, pref. HC, esp. toluene | Yes |
| | Alternative b: (1) Synthesis of ylide: 1–1.07 moles strong base, pref. sodium hydride, per mole CCX. Pref., add small amount of CCX to suspension of sodium hydride in THF stirred at 20°–25° C., cool to −20°–−15° C. once reaction commences and complete reaction at −20°–−15° C. | −20°–25° C., pref. −20°–0° C. | 0.75–2 hrs. | AIO, pref. ES, esp. THF | Yes |
| | (2) 1–1.25 moles ylide from CCX (assuming 100% conversion of CCX to ylide) per mole CCII. Add solution of CCII to ylide solution at −20°–−15° C. and stir at −20°–25° C. for balance of reaction. | | 0.75–18 hrs. | Same as Step 1 | Yes |
| GG (Reduction) | (1) At least 2 equivalents of transferable hydride from a metal hydride reducing agent, e.g., lithium aluminum hydride or diisobutylaluminum hydride, per mole CCXI, pref. 3.8–6 moles diisobutylaluminum hydride per mole CCXI. | 0°–25° C., pref. 0°–10° C. | 0.7–3 hrs. | AIO, pref. ES, e.g., THF | Yes |
| | (2) Quench with, for example, saturated aqueous ammonium chloride or sodium sulfate solution. | 0°–25° C. | 5–15 min. | — | — |
| GH (Oxidation) | 5–50 moles, pref. 10–30 moles, manganese dioxide, pref. activated manganese dioxide, per mole CCXII. | 20° C.–reflux, pref. 20°–40° C. | 3–24 hrs., pref. 10–18 hrs. | AIO, pref. HC or ES, pref. diethyl ether | — |
| GI (Reduction) | (a) Same as Reaction K, Alternative a (Molar quantities are per mole CCVI). | Same as K, a | Same as K, a | Same as K, a | — |
| | (b) Same as Reaction CD or GG utilizing half the indicated molar quantities (Molar quantities are per mole CCVI). | Same as CD or GG | Same as CD or GG | Same as CD or GG | Yes |
| GJ (Halogenation) | Same as Reaction AG (Molar quantities are per mole CCXIII). | Same as AG | Same as AG | Same as AG | — |
| GK | Same as Reaction A (Molar quantities are per mole CCXIV). | Same as A | Same as A | Same as A | Yes |

In the preceding table,

AIO = anhydrous inert organic solvent

ES = ether solvent, for example, diethyl ether, 1,2-diethoxyethane, 1,2-dimethoxyethane, tetrahydrofuran and mixtures thereof esp. = especially HC = hydrocarbon solvent, for example, benzene, toluene, xylene and mixtures thereof HLA = halogenated lower alkane solvent, for example, carbon tetrachloride, chloroform, 1,1-dichloroethane, 1,2-dichloroethane, methylene chloride and 1,1,2-trichloroethane, usually preferably methylene chloride hr. (hrs.) = hours(s)

IO = inert organic solvent min. = minutes pref. = preferably, preferred

THF = tetrahydrofuran

Most of the molar amounts (ratios) given in the preceding table are merely exemplary and may be varied, as is evident to one of ordinary skill in the art. For example, in a reaction of two compounds one of which is readily available and one of which isn't, an excess of the readily available compound may be used to drive the reaction further towards completion (unless the use of an excess would increase the synthesis of an undesired compound).

Likewise, most of the temperature ranges given in the preceding table are merely exemplary, and it is within the ability of one of ordinary skill in the art to vary those that are not critical.

The reaction times set forth in the preceding table are also merely exemplary and may be varied. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the preceding table.

As utilized in the preceding table, the term "solvent" embraces mixtures of solvents and implies that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized.

The term "inert atmosphere", as utilized in the preceding table, means an atmosphere that does not react with any of the reactants, intermediates or end products or otherwise interfere with the reaction. While a carbon dioxide atmosphere is suitable for certain reactions, the inert atmosphere is usually nitrogen, helium, neon, argon or krypton, or a mixture thereof, and most often dry nitrogen to maintain anhydrous conditions. Most reactions, including those where the use of an inert atmosphere is not specified, are carried out under an inert atmosphere, usually dry nitrogen, for convenience.

Reactions analogous to Reactions A-C, E-G, I-T, AG, BF, CD, CE, DC, DD, GA-GE and GG-GK are described in detail in copending application Ser. No. 06/722,288, filed by Faizulla G. Kathawala on Apr. 11, 1985 and titled Indole Analogs Of Mevalonolactone And Derivatives Thereof. These reactions may be carried out analogously to the corresponding reactions of said application. Also disclosed in said application are Reactions EA-EH of this application. Said application, particularly pages 14–21, 24–26, 28–52, 65–76, 82–96, 98–102, 106, 107 and 116–122 thereof, is hereby incorporated by reference. Generally, where the reaction conditions set forth in said application differ from those set forth in this application, the reaction conditions set forth in said application may also be utilized for the compounds of this application.

Reactions EA-EF and EI-EL are described in further detail in copending application Ser. No. 06/563,945, filed by me and Charles F. Jewell, Jr. on Dec. 21, 1983 and titled Derivatives Of Tetrahydropyran-2-One. Also described in said application is an alternate procedure for carrying out Reactions EG and EH. Said application, particularly pages 15–28 thereof, is hereby incorporated by reference.

Reactions FA-FC and FF are described in further detail in copending application Ser. No. 06/596,411, filed by me and Charles F. Jewell, Jr. on Apr. 3, 1984 and titled Preparation Of Olefinic Compounds. Pages 16–19 of said application are hereby incorporated by reference.

The product of each reaction may, if desired, be purified by conventional techniques such as recrystallization (if a solid), column chromatography, preparative thin layer chromatography, gas chromatography (if sufficiently volatile), fractional distillation under high vacuum (if sufficiently volatile) or high pressure (performance) liquid chromatography (HPLC). Often, however, the crude product of one reaction may be employed in the following reaction without purification.

Some of the reactions described above yield mixtures of two or more products only one of which leads to the desired compound of Formula I. For example, Reactions AE and AH may yield mixtures when, for example, at least one of $R_2$-$R_7$ is primary or secondary alkyl, Reactions BD and BG may yield mixtures when, for example, at least one of $R_1$-$R_7$ is methyl and, as set forth above, Reaction DB usually results in a mixture. Any obtained mixture may be separated by conventional techniques such as those set forth in the preceding paragraph.

As is evident to those in the art, each of the compounds of Formulae XVII, XVIIC, XX, LXXIII and XCIV has a single center of asymmetry and, therefore, may be resolved into two optically active isomers. When a compound of Formula XVIIC, XX or XCIV is converted into a compound of Formula XVIIE, XXI or XCV or C, respectively, an additional center of asymmetry is generated. Consequently, when a racemic compound of Formula XVIIC, XX or XCIV is utilized, four stereoisomers (two pairs of diastereoisomers) of the resulting compound of Formula XVIIE, XXI or XCV or C are formed, whereas when an optically pure compound of Formula XVIIC, XX or XCIV is utilized, two diastereoisomers of the compound of Formula XVIIE, XXI or XCV or C are formed. The center of asymmetry of each compound of Formula LXXIII may be ignored since it is destroyed in the following reaction (Reaction DB).

The compounds of Formulae I (including those of Formulae IA-ID, XII, XIV, XXI, etc.), X, XI, XIII, XVIIE, XCV, XCVI and C have two centers of asymmetry and, therefore, may exist in four stereoisomeric forms. Except where the compound is formed from an optically pure precursor already having both chiral carbon atoms or where the reaction involves the use of a stereospecific reagent that gives an optically pure product, the compound is obtained as a mixture of two (if formed from an optically pure compound having one cneter of asymmetry) or four (if formed from a racemic compound having one center of asymmetry) stereoisomers.

The obtained mixtures of stereoisomers may be separated by conventional means. For example, diastereoisomers may be separated by fractional crystallization, column chromatography, preparative thin layer chromatography and HPLC. Each mixture of four stereoisomers of a compound of Formula XXX may, for example, be separated by HPLC into its cis and trans (lactone) components, each of which is a racemate that may be resolved into two optically active enantiomers.

Techniques for separating a racemate into its two optically active enantiomers are known. For example, a racemic compound having a carboxylic acid group may be reacted with an optically pure organic base having at least one center of asymmetry to form a mixture of diastereoisomeric salts that may be separated by fractional crystallization, column chromatography, etc. or it may be reacted with an optically pure alcohol having at least one center of asymmetry to form a mixture of diastereoisomeric esters which may be separated by conventional techniques such as those set forth above or below. Likewise, a racemic compound having a carboxylic acid, acyl halide, ester or lactone group may be reacted with an optically pure organic base, i.e., an amine, to form a mixture of diastereoisomeric amides that may be separated by conventional means, e.g., fractional crystallization, column chromatography and/or HPLC. For example, a racemic lactone of Formula XXX may be reacted with an excess of R-(+)-α-methylbenzylamine (or the corresponding S-(−) compound) to form a mixture of two diastereoisomeric α-methylbenzylamides which may be separated by, for example, column chromatography on a silica gel column and/or by HPLC using a Partisil column. Often it is desirable to utilize both techniques, i.e., to partially separate the diastereoisomers by column chromatography and to purify each fraction by HPLC. Typically, the α-methylbenzylamides are synthesized by reacting the racemic lactone with a large molar excess of the amine at 20°–25° C. for 16–24 hours. The reaction is run neat, with the excess amine serving as the solvent. After the reaction, the excess amine is removed by vacuum distillation at 25°–35° C. After separation, each chiral amide may be hydrolyzed to the corresponding, for example, sodium, salt by, for example, refluxing with 1.5–3, preferably 2–2.2, equivalents of a base such as sodium hydroxide for 5–25 hours in a mixture of water and ethanol. The resulting salts may be converted to the corresponding free acids, esters, lactones and other salts by conventional means such as the reactions set forth in Reaction Scheme IV. On the other hand, a racemic compound having a hydroxy group may be esterified with an optically pure carboxylic acid having at least one center of asymmetry to form a mixture of diastereoisomeric esters or it may be reacted with an optically pure trisubstituted silyl halide, e.g., (−)-α-naphthylphenylmethylchlorosilane (Sommer et al., J. Am. Chem. Soc. 80, 3271 (1958).), to form a mixture of two diastereoisomeric silyloxy compounds, which mixture may be separated by conventional techniques. For example, diastereoisomeric (−)-α-naphthylphenylmethylsilyl derivatives of a lactone of Formula XXX may be separated on a silica column having covalently bound L-phenylglycine. After separation, the optically pure salts, amides, esters or silyloxy compounds are reconverted to the corresponding carboxy group- or hydroxy group-containing compounds with retention of optical purity. For example, the process conditions disclosed for Reactions C, E, G and I may be utilized to cleave (−)-α-naphthylphenylmethylsilyl and other silyl groups.

The compounds of Formulae XVI, XVIIA, XVIIB, XVIID, XIX, XXIII, XXVI, XXVIII, XXXI, XXXII, XXXIV, XLI, XLII, LI, LII, LXI, LXII, LXV, LXXI, LXXII, LXXXI–LXXXVIII, XCIII, XCIX, CCV, CCIX and CCX and the reagents not designated by a Roman numeral are known or, if unknown, may be synthesized by processes analogous to those described in the literature for similar known compounds. For example, Compound LXXXI is commercially available tri-O-acetyl-D-glucal and Compounds LXXXV–LXXXVIII are disclosed in Yang et al., Tetrahedron Letters 23, 4305–4308 (1982).

A preferred process for the synthesis of the erythro racemate of the compound of Formula XCVII wherein $R_{10}$ is hydrogen, and $R_{12}'$ is methyl is disclosed in Kapa, Tetrahedron Letters 25, 2435–2438 (1984). The other compounds of Formula XCVII wherein $R_{10}$ is hydrogen in racemic erythro form may be synthesized similarly. See also U.S. Pat. No. 4,571,428. Said patent, particularly column 3, line 3-column 6, line 23 and column 7, line 27-column 11, line 22 is hereby incorporated by reference.

Since any compound of Formula I wherein Z is a group of Formula a wherein $R_{11}$ is a cation other than M may be converted into the corresponding compound wherein $R_{11}$ is hydrogen, M or $R_{12}$ by the processes of Reaction Scheme IV, the compounds of Formula I wherein Z is a group of Formula a and $R_{11}$ is a pharmaceutically unacceptable cation are also within the scope of this invention since they are useful as intermediates. However, such compounds are not compounds of Formula I as utilized in this application, except where indicated to the contrary.

Also within the scope of this invention are the intermediates of Formulae V, VII, XI, XIII, XVII, XVIIC, XVIIE, XX, XCVIII, C, CCIV, CCXI and CCXII and those of Formulae XCVI and XCVII wherein $R_{10}$ is $C_{1-3}$alkyl. The preferences for each variable are the same as those set forth for the compounds of Formula I, with the preferred groups of such compounds including those that correspond to Groups (xix)–(xxvii), (xlvi)–(liv), (lxxiii)–(lxxxi) and (c)–(cviii) (for Formulae V and VII) and Groups (i)–(xviii), (xxviii)–(xlv), (lv)–(lxxii) and (lxxxii)–(xcix) (for each of the others) to the extent consistent therewith.

The entire specification of parent application Serial No. 06/623,393, particularly pages 1–9 and 55–60 thereof, is hereby incorporated by reference, as if set forth herein in its entirety.

Besides having the utility set forth below, every compound of Formula I is useful as an intermediate in the synthesis of one or more other compounds of Formula I utilizing the reactions set forth in Reaction Scheme IV.

The compounds of Formula I are competitive inhibitors of 3-hydroxy-3-methylglutaryl coenzyme A (HMG-CoA) reductase, the rate limiting enzyme in chloesterol biosynthesis, and, therefore, they are inhibitors of cholesterol biosynthesis. Consequently, they are useful for lowering the blood cholesterol level in animals, e.g., mammals, especially larger primates such as humans, and, therefore, as hypolipoproteinemic and anti-atherosclerotic agents. The biological activity of the compounds of Formula I may be demonstrated in the following two tests:

Test A. In Vitro Microsomal Assay of HMG-CoA Reductase Inhibition:

200 μl. aliquots (1.08-1.50 mg./ml.) of rat liver microsomal suspensions, freshly prepared from male Sprague-Dawley rats (150-225 g. body weight), in Buffer A with 10 mmol. dithiothreitol are incubated with 10 μl. of a solution of the test substance in dimethylacetamide and assayed for HMG-CoA reductase activity as described in Ackerman et al., J. Lipid Res. 18, 408-413 (1977), the concentration of the test substance in the assay system being 0.0001-2,000 μmolar. In the assay the microsomes are the source of the HMG-CoA reductase enzyme which catalyzes the reduction of HMG-CoA to mevalonate. The assay employs a chloroform extraction to separate the product, [$^{14}$C]mevalonolactone, formed by the HMG-CoA reductase recution of the substrate, [$^{14}$C]HMG-CoA. [$^{3}$H]mevalonolactone is added as an internal reference. Inhibition of HMG-CoA reductase is calculated from the decrease in specific activity ([$^{14}$C/$^{3}$H]mevalonate) of test groups compared to controls.

Test B. In Vivo Cholesterol Biosynthesis Inhibition Test:

In vivo studies utilize male Wistar Royal Hart rats weighing 150±20 g. which have been kept for 7-10 days on an altered light cycle (6:30 A.M.-6:30 P.M. dark) housed two per cage and fed powdered Purina Rat Chow and water ad libitum. Three hours before the diurnal maximum of cholesterol synthesis at mid-dark, the rats are orally administered the test substance (e.g., 0.01-200 mg./kg. body weight) dissolved or as a suspension in 0.5% carboxymethylcellulose in a volume of 1 ml./100 g. body weight. Controls receive vehicle alone. One hour after receiving the test substance (or the vehicle alone), the rats are injected intraperitoneally with about 25 μCi/100 g. body weight of sodium [1-$^{14}$C]acetate 1-3 mCi/mmol. Two hours after mid-dark, blood samples are obtained under sodium hexobarbitol anesthesia, and the serum is separated by centrifugation.

Serum samples are saponified and neutralized, and the 3β-hydroxysterols are precipitated with digitonin basically as described in Sperry et al., J. Biol. Chem. 187, 97 (1950). The [$^{14}$C]digitonides are then counted by liquid scintillation spectrometry. After correcting for efficiencies, the results are calculted in nCi (nanocuries) of 3β-hydroxysterol formed per 100 ml. of serum. Inhibition of 3β-hydroxysterol synthesis is calculated from the reduction in the nCi of 3β-hydroxysterols formed from test groups compared to controls.

The following results were obtained:

| Test A: | Example 1 | $IC_{50}$ = | 0.08 μmolar |
|---|---|---|---|
| | Example 2 | $IC_{50}$ = | 103 μmolar |
| | Example 3 | $IC_{50}$ = | 0.06 μmolar |
| | Example 7 | $IC_{50}$ = | 0.04 μmolar |
| | Example 11 | $IC_{50}$ = | 0.26 μmolar |
| | Example 14 | $IC_{50}$ = | 0.02 μmolar |
| | Compactin | $IC_{50}$ = | 0.77 μmolar |
| | Mevinolin | $IC_{50}$ = | 0.14 μmolar |

$IC_{50}$ is the concentration of the test substance in the assay system calculated or observed to produce a 50% inhibition of HMG-CoA reductase activity.

| Test B: | Example 3 | $ED_{50}$ = | 0.05 mg./kg. |
|---|---|---|---|
| | Example 7 | $ED_{50}$ = | 0.06 mg./kg. |
| | Example 14 | $ED_{50}$ = | 0.013 mg./kg. |
| | Compactin | $ED_{50}$ = | 3.5 mg./kg. |
| | Mevinolin | $ED_{50}$ = | 0.41 mg./kg. |

$ED_{50}$ is the dose of the test substance calculated or observed to produce a 50% inhibition of 3β-hydroxysterol synthesis.

As set forth above, the compounds of formula I (including each and every subgroup thereof set forth in the specification and/or the claims) inhibit cholesterol biosynthesis and are useful for lowering the blood cholesterol level in animals, particularly mammals and more particularly larger primates, and, therefore, as hypolipoproteinemic and anti-atherosclerotic agents.

The compounds of Formula I may be formulated into conventional pharmaceutical compositions and administered by conventional modes of administration. The compounds of each and every subgroup thereof in the specification and/or claims may likewise be formulated into conventional pharmaceutical compositions.

The compounds of Formula I may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injection solutions or suspensions. The compositions may be prepared by conventional means. The preferred pharmaceutical compositions from the standpoint of ease of preparation and administration are solid compositions, particularly tablets and capsules.

The precise dosage of the compounds of Formula I to be employed for inhibiting cholesterol biosynthesis depends upon several factors including the host, the nature and the severity of the condition being treated, the mode of administration and the particular compound employed. However, in general, suitable daily oral dosages of the compounds of Formula I for the satisfactory inhibition or reduction of cholesterol biosynthesis (i.e., the satisfactory reduction of the blood cholesterol level and satisfactory treatment of hyperlipoproteinemia and atherosclerosis) are indicated to be 0.01-100, e.g., 0.01-5, mg./kg. body weight or, for most larger primates, a daily dosage of 0.1-2000 mg., suitably 0.1-150 mg., e.g., 0.1-20 mg. for the more active compounds. For the compound of Example 3, the oral daily dosage is indicated to be 0.05-2.5 mg./kg. body weight or, for most larger primates, it is indicated to be 0.5-20 mg. For the compound of Example 14, the oral daily dosage is indicated to be 0.01-1 mg./kg. body weight or, for most larger primates, it is indicated to be 0.1-20, preferably 1-20, mg.

The daily dosage may be divided into two to four equal portions or administered in a single dose. A typical oral dosage of the compounds of Examples 3 and 14 is indicated to be 1 mg. three times a day. Usually, a small dosage is administered initially, and the dosage is gradually increased until the optimal dosage for the host under treatment is determined. For administration by injection, a dosage somewhat lower than would be used for oral administration of the same compound to the same host having the same condition is usually employed. However, the above dosages are also typically used for i.v. administration.

A typical dosage unit for oral administration may contain 0.05-500 mg. of a compound of Formula I. Preferred dosage units contain 0.05-2.5 mg. of a compound of Formula I such as the compounds of Examples 3, 7 and 14.

The compounds of Formula I (including those of each and every subgroup thereof) may be formulated into such pharmaceutical compositions containing an amount of the active substance that is effective for inhibiting cholesterol biosynthesis, such compositions in unit dosage form and such compositions comprising a solid pharmaceutically acceptable carrier.

Representive formulations prepared by conventional techniques for encapsulation in a hard gelatin capsule are:

| A. Compound of Formula I, e.g., the compound of Example 3 | 0.5 mg. |
| Corn starch | 248 mg. |
| Magnesium stearate | 1.5 mg. |
| B. Compound of Formula I, e.g., the compound of Example 14 | 1 mg. |
| Corn starch | 248 mg. |
| Magnesium stearate | 1 mg. |

A representative formulation suitable for preparing tablets by conventional means is:

| Compound of Formula I, e.g., the compound of Example 7 | 1 mg. |
| Polyvinylpyrrolidone USP | 5 mg. |
| Powdered lactose | 183 mg. |
| Corn starch | 10 mg. |
| Magnesium stearate | 1 mg. |

The following examples show representative compounds encompassed by this invention and their synthesis. However, it should be understood that they are for purposes of illustration only.

EXAMPLE 1

(E)-Trans-6S-(2'-[4''-(4'''-fluorophenyl)-1''-(1'''-methylethyl)-3''-phenyl-1H-pyrazol-5''-yl]ethenyl)-4R-hydroxy-3,4,5,6-tetrahydro-2H-pyran-2-one

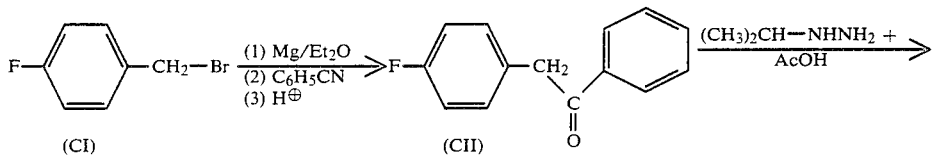

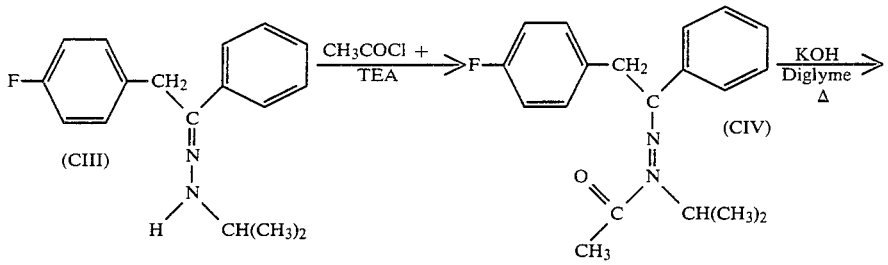

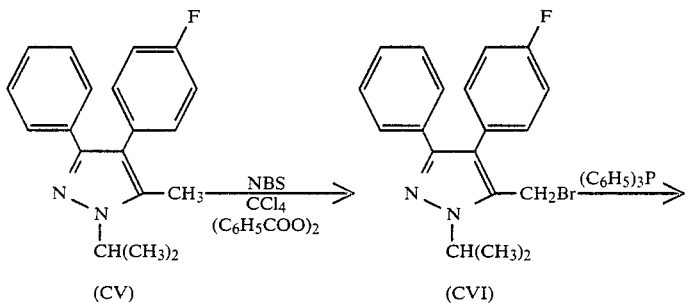

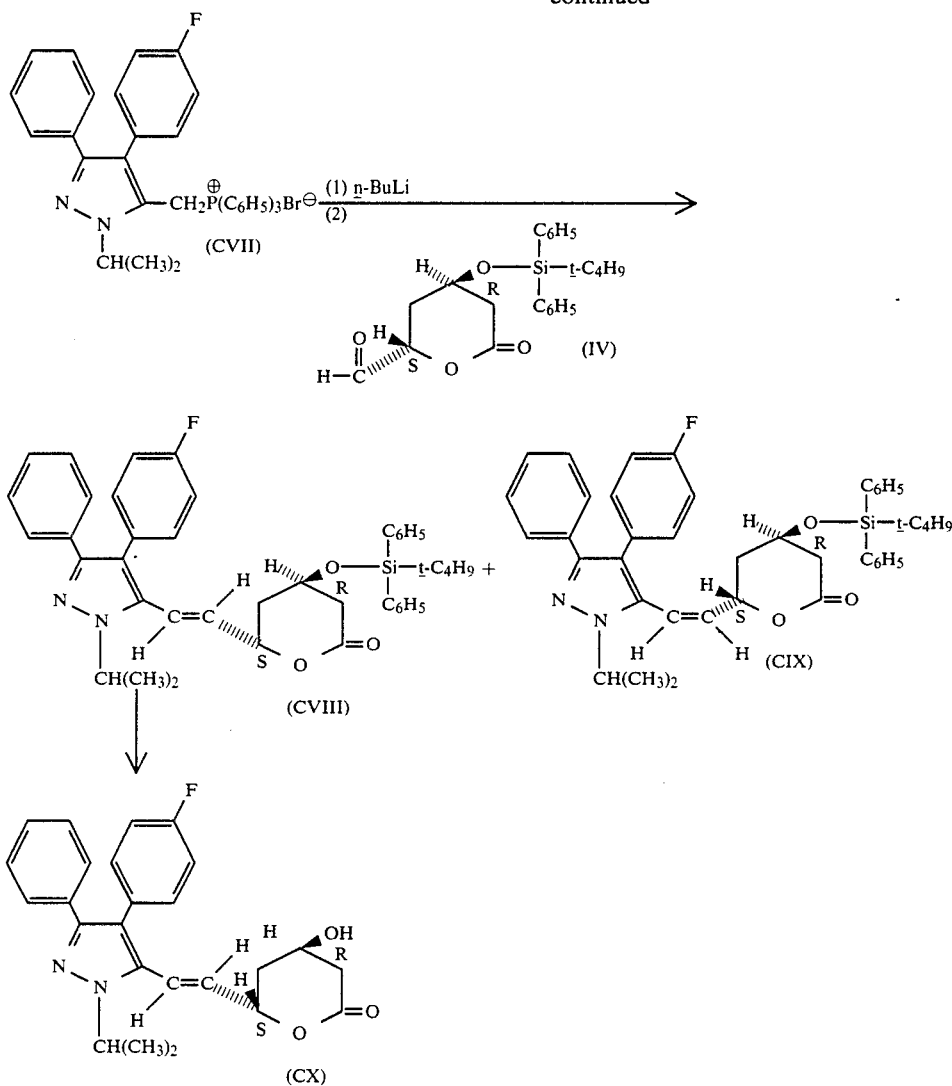

Step 1 (Reaction AA)

α-(4-Fluorophenyl)acetophenone (Compounds CII)

5.27 ml. (42 mmoles) of 4-fluorobenzyl bromide (Compound CI) is slowly added to 928 mg. (38 mmoles) of magnesium turnings stirred in 38 ml. of anhydrous diethyl ether under nitrogen over a period of 45 minutes at a rate such that the reaction mixture gently refluxes. The reaction mixture is allowed to cool to 20°–25° C., 2.96 ml. (29 mmoles) of benzonitrile in 5 ml. of anhydrous diethyl ether is added over a period of 5 minutes, and the reaction mixture is stirred at 20°–25° C. for 3 hours, the reaction mixture being maintained under nitrogen throughout. The reaction mixture is slowly poured into ice cold 10% hydrochloric acid, and the organic phase is separated. The aqueous phase is extracted five times with diethyl ether and twice with ethyl acetate, and the organic phases are combined, washed once with saturated sodium bicarbonate solution, washed once with saturated sodium chloride solution, dried over anhydrous magnesium sulfate and evaporated at reduced pressure. The residue is dissolved in 450 ml. of hot petroleum ether, and the solution is filtered and cooled to obtain the product as an off-white solid (3.5 g.), m.p. 109°–110° C. A second crop is also obtained (0.39 g.).

Step 2 (Reaction AB)

1-[2'-(4''-Fluorophenyl)-1'-phenylethylidene]-2-(1'-methylethyl)-hydrazine (Compound CIII)

A mixture of 3 g. (14.0 mmoles) of Compound CII, 2.45 ml. (28 mmoles) of isopropylhydrazine and 0.5 ml. of acetic acid in 23 ml. of 95% ethanol is stirred at 80° C. for 1.4 hours. The reaction mixture is cooled, most of the solvent is evaporated at reduced pressure and methylene chloride is added. The methylene chloride solution is washed with saturated sodium chloride solution, dried over anhydrous sodium sulfate and evaporated to dryness at reduced pressure. Toluene is added to the residue, and the mixture is evaporated to dryness at reduced pressure to obtain the product (3.97 g.) as a somewhat cloudy yellow liquid.

Isopropylhydrazine is synthesized as follows: 9.39 ml. (0.1 mole) of 2-bromopropane is slowly added over a period of 2 hours to 48.4 ml. (1 mole) of hydrazine.hydrate stirred under nitrogen at 20°–25° C. During the addition the temperature rises to as high as 40° C. The reaction mixture is stirred under nitrogen at 60° C. for 3.25 hours, cooled to 20°-25° C. and continuously extracted with diethyl ether for 20 hours. The diethyl ether is evaporated at reduced pressure to obtain the crude product (4.03 g.) which is used as is. B.p. 106°-107° C. (742 mm. Hg.)

Step 3 (Reaction AC)

1-Acetyl-2-[2'-(4''-fluorophenyl)-1'-phenylethylidene]-1-(1'-methylethyl)hydrazine (Compound CIV)

3.9 ml. (28 mmoles) of triethylamine is added to a solution of 3.97 g. ($\leqq$14 mmoles) of crude Compound CIII in 140 ml. of toluene, the mixture is cooled to 0°-5° C., 1.24 ml. (17.5 mmoles) of acetyl chloride is added, and the reaction mixture is stirred for 1.5 hours with gradual warming to 20°-25° C. 500 ml. of diethyl ether is added, and the solution is filtered through anhydrous sodium sulfate and evaporated to dryness at reduced pressure. Toluene is added, and the mixture is evaporated to dryness at reduced pressure. The residue is chromatographed on 160 g. of silica gel utilizing 75% diethyl ether/n-hexane as the eluant. The fractions containing the product (as determined by thin layer chromatography) are combined and evaporated at reduced pressure to obtain the product as a yellow oil (3.6 g. (82%)).

Step 4 (Reaction AD)

4-(4'-Fluorophenyl)-5-methyl-1-(1'-methylethyl)-3-phenyl-1H-pyrazole (Compound CV)

A mixture of 1.6 g. (5.1 mmoles) of Compound CIV and 0.656 g. (10.2 mmoles) of potassium hydroxide in 51 ml. of bis-(2-methoxyethyl) ether is stirred at 80° C. under nitrogen for 2 hours, an additional 0.75 g. of potassium hydroxide is added, and the reaction mixture is stirred under nitrogen at 80° C. for 2 hours and at 20°-25° C. for 16 hours and poured into 300 ml. of distilled water. The mixture is extracted three times with 150 ml. portions of diethyl ether and once with 200 ml. of ethyl acetate. The organic extracts are combined, washed with 500 ml. of ice cold 3% hydrochloric acid and twice with saturated sodium chloride solution, dried over anhydrous magnesium sulfate, filtered, concentrated at reduced pressure, and heated at 90°-100° C. for a few minutes. A small amount of chloroform and n-hexane is added, and the solution is cooled in a sealed container at −78° C. to obtain the crystalline product (0.92 g. (61%)), m.p. 139°-140° C.

Step 5 (Reaction AH)

5-Bromomethyl-4-(4'-fluorophenyl)-1-(1'-methylethyl)-3-phenyl-1H-pyrazole (Compound CVI)

A mixture of 0.9 g. (3.06 mmoles) of Compound CV, 654 mg. (3.67 mmoles) of N-bromosuccinimide and 37 mg. of 5 molar % dibenzoyl peroxide in 61.2 ml. of carbon tetrachloride is stirred at 80° C. under nitrogen for 45 minutes. The reaction mixture is cooled to 20°-25° C., filtered and evaporated to dryness at reduced pressure to obtain the crude product as a pale yellow oil. Petroleum ether is added to partially crystalline the product. 0.393 g. of crystalline product and 0.66 g. of oily product are obtained. An analytical sample is recrystallized from petroleum ether, m.p. 93°-95° C.

Step 6 (Reaction A)

4-(4'-Fluorophenyl)-1-(1'-methylethyl)-3-phenyl-5-triphenylphosphoniummethyl-1H-pyrazole (Compound CVII)

A mixture of 0.6 g. (1.77 mmoles) of Compound CVI (the oily product of the preceding step) and 0.58 g. (2.21 mmoles) of triphenylphosphine in 42 ml. of toluene is stirred at 80° C. under nitrogen for 45 minutes. The reaction mixture is allowed to cool to 20°-25° C., and the solid white product is collected by filtration and washed with diethyl ether (0.7 g. (62.5%)).

Step 7 (Reaction EL and B)

(E)-Trans-4R-(1',1'-dimethylethyl-diphenylsilyl oxy)-6S-(2'-[4''-(4'''-fluorophenyl)-1''-(1'''-methylethyl)-3''-phenyl-1H-pyrazol-5''-yl]ethenyl)-3,4,5,6-tetrahydro-2H-pyran-2-one (Compound CVIII and its (Z) isomer (Compound CIX)

(a) Trans-4R-(1',1'-dimethylethyl-diphenylsilyloxy)-6S-formyl-2H-pyran-2one (Compound IV): Ozone is bubbled through a solution of 200 mg. (0.526 mmole) of trans-4R-(1',1'-dimethylethyl-diphenylsilyloxy-6S-vinyl-3,4,5,6-tetrahydro-2H-pyran-2-one (Compound XCII) in 26 ml. of methylene chloride stirred at −78° C. until the solution has a bluish tint (about 5 minutes), and 0.5 ml. of dimethyl sulfide is added by syringe to quench the reaction mixture. The mixture is warmed to 20°-25° C., the solvent is evaporated at reduced pressure, and any remaining solvent is evaporated under high vacuum to obtain the product as an oil.

(b) 501 mg. (0.789 mmole) of Compound CVII is dried under high vacuum for 2 hours (to remove any trace of solvent present) and dissolved in 7.89 ml. of dry tetrahydrofuran. The solution is stirred at −30° C. under nitrogen and 570 $\mu$l. of 1.7M. n-butyllithium/n-hexane (0.969 mmole) is added by syringe to obtain a solution of the ylide (Compound of Formula CVII having a —CH=P($C_6H_5$)$_3$ group in lieu of the —$CH_2P^{\oplus}(C_6H_5)_3Br^{\ominus}$ group).

(c) The ylide solution of Part (b) is added by syringe to a solution of Compound IV (from Part (a)) in 5.26 ml. of dry tetrahydrofuran stirred at −30° C. under nitrogen, and the reaction mixture is stirred under the same conditions for 1 hour and quenched with 5 ml. of saturated ammonium chloride solution. The mixture is extracted with 150 ml. of diethyl ether, and the diethyl ether extract is washed twice with saturated sodium chloride solution, dried over anydrous magnesium sulfate, filtered and evaporated to dryness at reduced pressure to obtain the crude product as a brown foam (439.6 mg.).

(d) The brown foam from Part (c) is triturated three times with 50% diethyl ether/n-hexane, and the diethyl ether/n-hexane solutions are combined and evaporated at reduced pressure to an oil (~110 mg.). The oil is chromatographed on 40 g. of silica gel utilizing 50% diethyl ether/n-hexane as the eluant, and the fractions containing each product are combined and evaporated at reduced pressure to obtain the (E) olefin (Compound CVIII) (45.1 (13%)) and the (Z) olefin (Compound CIX) (38.0 mg. (11%)) as oils. The (E) olefin is eluted prior to the (Z) olefin.

Step 8 (Reaction C)

(E)-Trans-6S-(2'-[4"-(4'"-fluorophenyl)-1"-(1'"-methylethyl)-3"-phenyl-1H-pyrazol-5"-yl]ethenyl)-4R-hydroxy-3,4,5,6-tetrahydro-2H-pyran-2-one (Compound CX)

16.2 μl. (0.28 mmole) of glacial acetic acid is added dropwise by syringe to a solution of 36.6 mg. (0.056 mmole) of Compound CVIII in 2.8 ml. of tetrahydrofuran stirred at 20°-25° C. under nitrogen. 224 μl. of 1M. tetra-n-butylammonium fluoride/tetrahydrofuran (0.224 mmole) is added by syringe, and the reaction mixture is stirred at 20°-25° C. under nitrogen for 3.75 hours and poured into 20 ml. of ice cold water. The mixture is extracted four times with diethyl ether, and the diethyl ether extracts are combined, washed with saturated sodium bicarbonate solution, washed with saturated sodium chloride solution, dried over anhydrous magnesium sulfate, filtered and evaporated to dryness at reduced pressure. The residue is washed with 50% diethyl ether/petroleum ether to obtain the product as a white solid (15.4 mg.), m.p. 216° C. (yellows and shrinks at 214° C.). $[\alpha]_D^{25} = -6.86°$ (CH$_3$COCH$_3$, c=0.35)

N.M.R. (CDCl$_3$): 1.59 (d (J=6.5 Hz.), 6H), 1.87 (m, 2H), 2.69 (m, 2H), 4.35 (m, 1H), 4.62 (m (J=6.5 Hz.), 1H, 5.2 (m, 1H), 5.6 (dd (J$_1$=16 Hz., J$_2$=5 Hz.), 1H), 6.58 (d (J=16 Hz.), 1H), 7.0-7.5 (m, 9H).

EXAMPLE 2

(Z)-Trans-6S-(2'-[4"-(4'"-fluorophenyl)-1"-(1'"-methylethyl)-3"-phenyl-1H-pyrazol-5"-yl]ethenyl)-4R-hydroxy-3,4,5,6-tetrahydro-2H-pyran-2-one (Compound CXI)

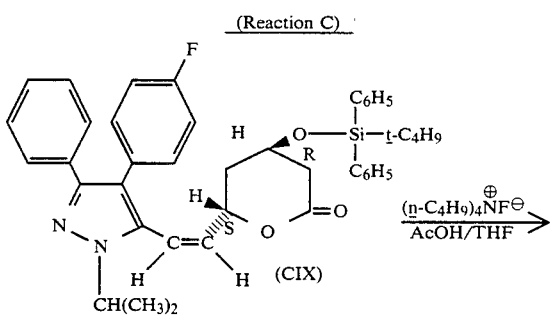

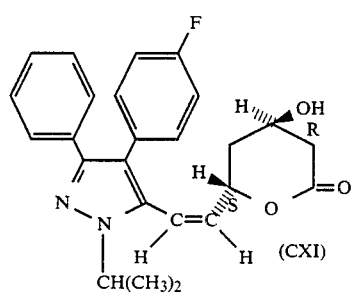

The product is obtained from 34 mg. (0.052 mmole) of Compound CIX by the process of Step 8 of Example 1 utilizing 15.0 μl. (0.26 mmole) of glacial acetic acid, 208 μl. of 1M. tetra-n-butylammonium fluoride/tetrahydrofuran (0.208 mmole) and, as the solvent, 26 ml. of tetrahydrofuran except that the reaction time is 24–28 hours (14.5 mg., m.p. 190° C. $[\alpha]_D^{25}=+171.37°$ (CH$_2$Cl$_2$, c=0.51)

N.M.R. (CDCl$_3$): 0.72 (m, 1H), 1.27 (m, 1H), 1.46 (m, 1H), 1.58 (d (J=6.5 Hz.), 6H), 2.52 (m, 2H), 4.1 (m, 1H), 4.5 (m (J=6.5 Hz.), 1H), 4.95 (m, 1H), 5.83 (dd (J$_1$=11 Hz., J$_2$=10 Hz.), 1H), 6.5 (d (J=11 Hz.), 1H), 6.95–7.45 (m, 9H).

EXAMPLE 3

Sodium erythro-(E)-3R,5S-dihydroxy-7-[4'-(4"-fluorophenyl)-1'-(1"-methylethyl)-3'-phenyl-1H-pyrazol-5'-yl]hept-6-enoate

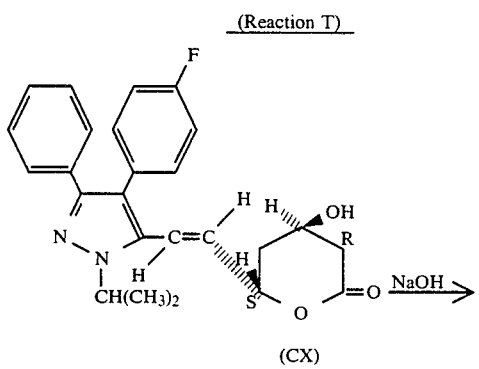

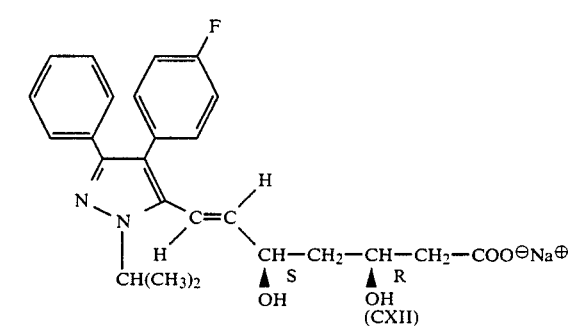

50.16 μl. of 0.5N. sodium hydroxide solution (0.0251 mmole) is added by syringe to a solution of 11.1 mg. (0.0264 mmole) of Compound CX in 2 ml. of methanol stirred at 20°-25° C., and the reaction mixture is stirred under nitrogen at this temperature for 3 hours. The methanol is evaporated at reduced pressure, and the residue is dissolved in 2 ml. of water. The aqueous solution is carefully extracted with diethyl ether, and the last traces of diethyl ether are removed at reduced pressure. The aqueous solution is cooled to −78° C. and freeze-dried under high vacuum to obtain the product as a free-flowing pale yellow foam (10.2 mg.), m.p. begins to darken at 166° C.; almost completely a black char at 215° C.

N.M.R. (CDCl$_3$+CD$_3$OD): 1.53 (d (J=6.5 Hz.), 6H), 1.5 (m, 2H), 2.3 (m, 2H), 4.1 (bm, 1H), 4.3 (bm, 1H), 4.65 (m (J=6.5 Hz.), 1H), 5.62 (dd (J$_1$=16 Hz., J$_2$=5 Hz.), 1H), 6.48 (d (J=16 Hz.), 1H), 6.9–7.4 (m, 9H).

EXAMPLE 4

Sodium erythro-(Z)-3R,5S-dihydroxy-7-[4'-(4"-fluorophenyl)-1'-(1"-methylethyl)-3'-phenyl-1H-pyrazol-5'-yl]hept-6enoate (Reaction T)

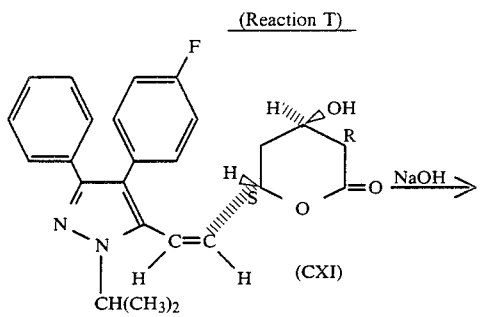

-continued
(Reaction T)

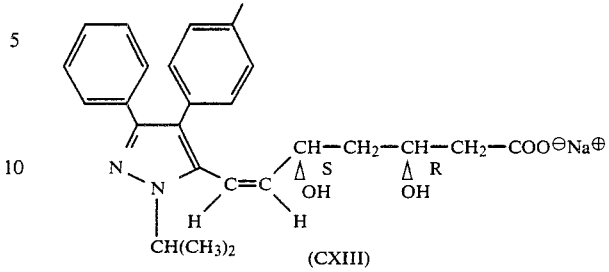

The product is obtained from Compound CXI substantially in accordance with the process of Example 3.

EXAMPLES 5 AND 6

Methyl erythro-(E)-3,5-dihydroxy-7-[4'-(4"-fluorophenyl)-1'-(1"-methylethyl)-3'-phenyl-1H-pyrazol-5'-yl]hept-6-enoate and (E)-Trans-6-(2'-[4"-(4'''-fluorophenyl)-1"-(1'''-methylethyl)-3"-phenyl-1H-pyrazol-5"-yl]ethenyl)-4-hydroxy-3,4,5,6-tetrahydro2H-pyran-2-one

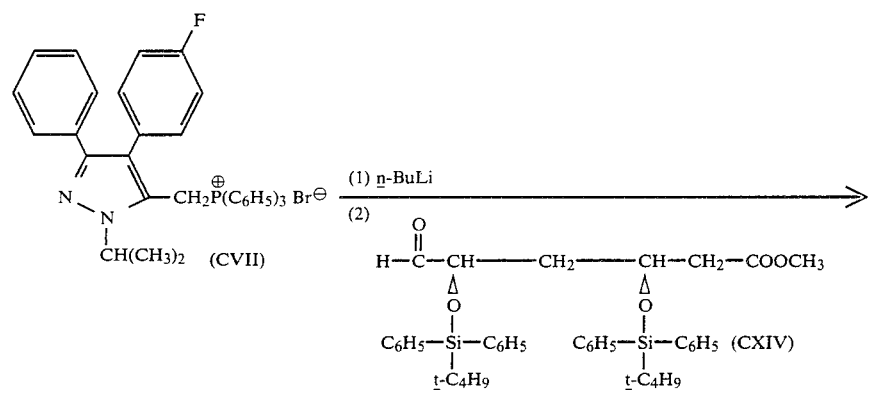

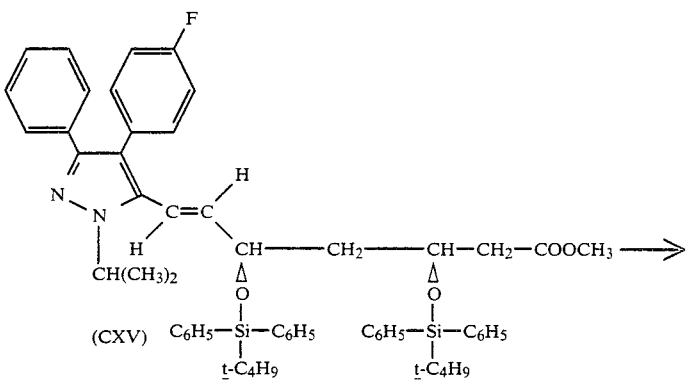

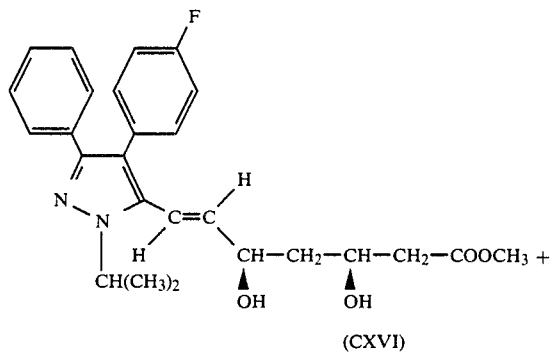

(CXVI)

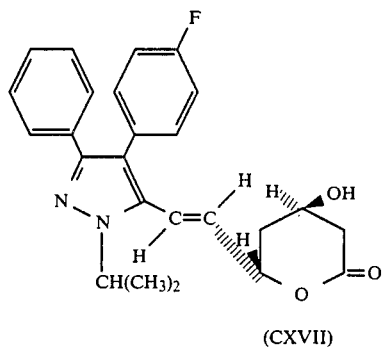

(CXVII)

Step 1 (Reaction F)

Methyl erythro-(E)-3,5-[di-(1',1'-dimethylethyl-diphenyl-silyloxy)]-7-[4'-(4''-fluorophenyl)-1'-(1''-methylethyl)-3'-phenyl-1H-pyrazol-5'-yl]hept-6-enoate (Compound CXV)

The product is obtained from 0.7 g. (1.1 mmoles) of Compound CVII (Example 1, Step 6), 0.7 g. (1.1 mmoles) of methyl erythro-3,5-di-(1',1'-dimethylethyl-diphenylsilyloxy)-6-oxohexanoate (Compound CXIV, Example 1, Step F of said application U.S. Pat. No. 4,571,428 flash chromatographed on a silica gel column utilizing 1:1 chloroform/n-hexane as the eluant prior to use), 1.4 ml. of 1.6M. n-butyllithium/n-hexane (2.2 mmoles) and 25 ml. of dry tetrahydrofuran as the solvent substantially in accordance with Parts (b) and (c) of Step 7 of Example 1, the principal differences being that the solution of Compound CXIV in dry tetrahydrofuran is added dropwise to the solution of the ylide produced from Compound CVII and the reaction time is 16 hours. The crude oily product is flash chromatographed on a silica gel column (2.5 cm.×15.3 cm.) utilizing 25% diethyl ether/n-hexane as the eluant to obtain the crude product as an oil (0.83 g.).

Step 2 (Reaction G)

Methyl erythro-(E)-3,5-dihydroxy-7-[4'-(4''-fluorophenyl)-1'-(1''methylethyl)-3'-phenyl-1H-pyrazol-5'-yl]hept-6-enoate (Compound CXVI) and (E)-Trans-6-(2'-[4''-(4'''-fluorophenyl)-1''(1'''-methylethyl)-3''-phenyl-1H-pyrazol-5''-yl]ethenyl)-4-hydroxy-3,4,5,6-tetrahydro2H-pyran-2-one (Compound CXVII)

(a) 3.6 ml. of 1M. tetra-n-butylammonium fluoride/tetrahydrofuran (3.6 mmoles) is added to a mixture of 0.83 g. (0.9 mmole) of crude Compound CXV (from the preceding step), 0.42 ml. (7.2 mmoles) of glacial acetic acid and 20 ml. of tetrahydrofuran, and the reaction mixture is stirred at 20°-25° C. for 24 hours and poured into saturated sodium bicarbonate solution. The mixture is extracted with diethyl ether, the diethyl ether extract is dried over anhydrous magnesium sulfate, and the diethyl ether is evaporated at reduced pressure. The residue is chromatographed on a silica gel column (2.5 cm.×20.3 cm.) utilizing 7:2:1 methyl t-butyl ether/n-hexane/acetone as the eluant. The fractions containing the first component of the major product (as determined by thin layer chromatography) are combined and evaporated at reduced pressure to obtain Compound CXVI as an oil (30 mg.).

N.M.R. (CDCl₃): 1.46–1.58 (m, 2H), 1.58 (d, 6H), 2.46 (d, 2H), 3.10–3.70 (bm, 2H), 3.72 (s, 3H), 4.20 (m, 1H), 4.42 (m, 1H), 4.65 (m, 1H), 5.60 (dd, 1H), 6.52 (d, 1H), 7.00 (t, 2H), 7.12–7.25 (m, 5H), 7.35–7.40 (m, 2H).

The product is a racemate that may be resolved to obtain the 3R,5S and 3S,5R enantiomers.

(b) The fractions containing the second component of the major product (see Part (a)) are combined and evaporated at reduced pressure to obtain Compound CXVII as crystalline needles (11 mg.).

The product is a racemate that may be resolved to obtain the 4R,6S and 4S,6R enantiomers.

EXAMPLE 7

Sodium erythro-(E)-3,5-dihydroxy-7-[4'-(4''-fluorophenyl)-1'-(1''-methylethyl)-3'-phenyl-1H-pyrazol-5'-yl]hept-6-enoate (Reaction T)

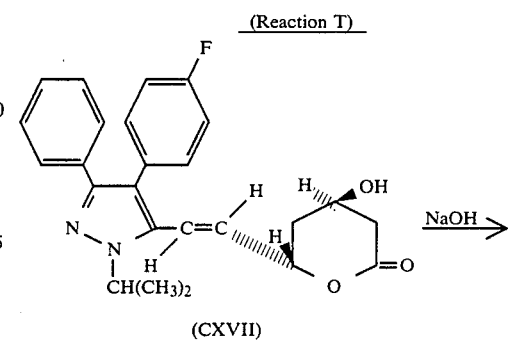

(CXVII)

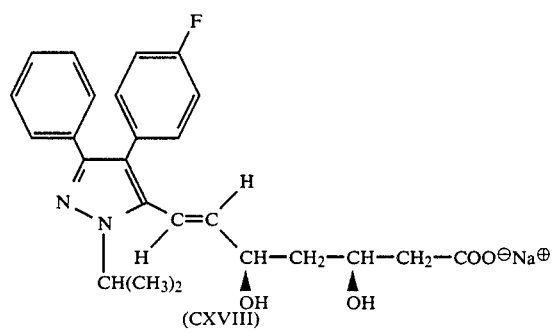

(CXVIII)

A mixture of 11 mg. (0.026 mmole) of Compound CXVII, 0.05 ml. of 0.5N. sodium hydroxide (0.25 mmole) and 5 ml. of 95% ethanol is stirred at 20°-25° C. for 2 hours and evaporated to dryness at reduced pressure. The residue is dissolved in about 3 ml. of water, and the solution is washed twice with diethyl ether and freeze dried to obtain the product as a solid foam (15 mg.).
N.M.R. (CDCl₃+CD₃OD): 1.4–1.5 (m, 2H), 1.58 (d, 6H), 2.18–2.5 (m, 2H), 4.1 (m, 1H), 4.36 (m, 1H), 4.68 (m, 1H), 5.65 (dd, 1H), 6.51 (d, 1H), 6.92–7.05 (m, 2H), 7.10–7.40 (m, 7H).
The product is a racemate that may be resolved to obtain the 3R,5S and 3S,5R enantiomers.
EXAMPLE 8
Ethyl (E)-3,5-dihydroxy-7-[3'-(4''-fluorophenyl)-5'-(1''-methylethyl)-1'-phenyl-1H-pyrazol-4'-yl]hept-6-enoate
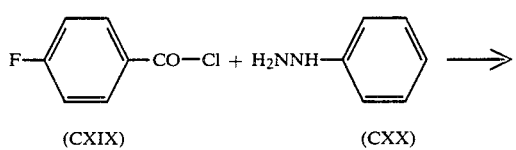
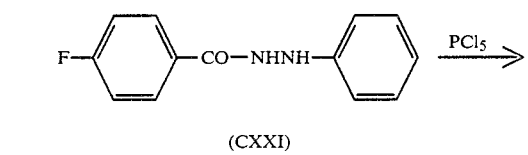
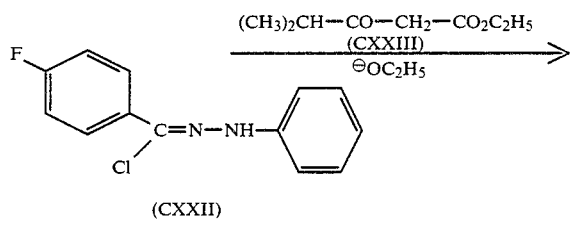
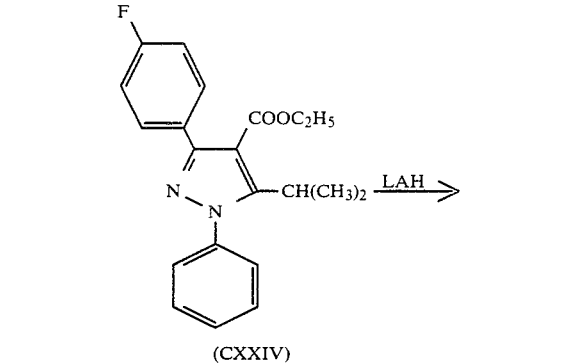
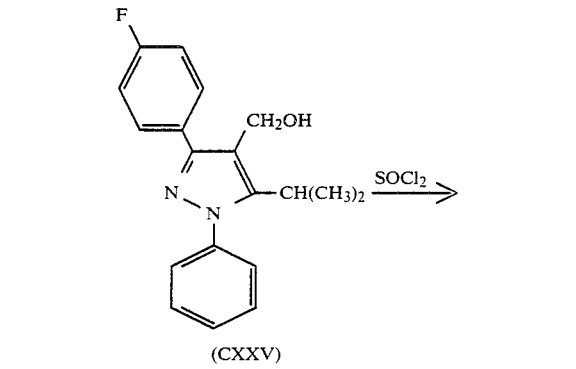
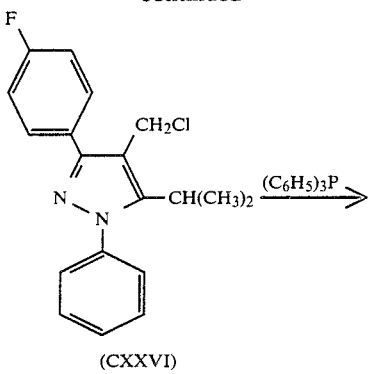
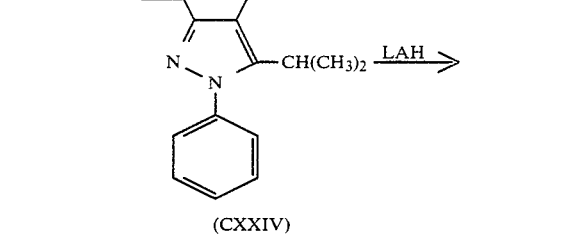
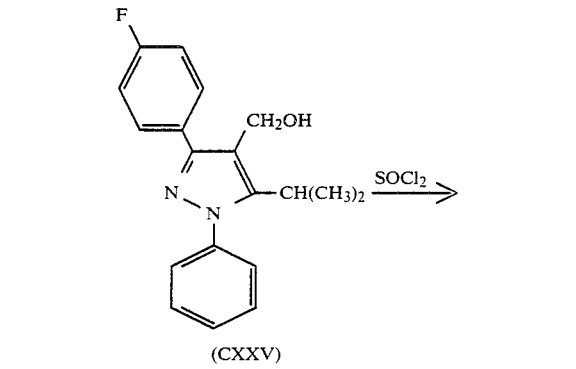

Step 1 (Reaction CA)

4-Fluorobenzoic acid-N'-phenylhydrazide (Compound CXXI)

30 ml. (0.25 mole) of 4-fluorobenzoyl chloride is added dropwise over a 30 minute period to a mixture of 25 ml. (0.25 mole) of phenylhydrazine and 35 ml. (0.25 mole) of triethylamine in 500 ml. of anhydrous diethyl ether stirred at −10° C. under nitrogen. The reaction mixture is allowed to warm to 20°–25° C. and stirred under nitrogen for 3 hours. The obtained solids are collected by filtration, washed with diethyl ether and dissolved in about 600 ml. of methylene chloride. The methylene chloride solution is filtered and evaporated at reduced pressure to near dryness, and n-hexane is added to obtain the crude solid product (26 g.). The crude product is dissolved in tetrahydrofuran and filtered to remove the triethylamine hydrochloride, the tetrahydrofuran is evaporated at reduced pressure, and the obtained product is recrystallized from acetone (12 g.), m.p. 181°–186° C. A second crop is also obtained (6 g.).

Step 2 (Reaction CB)

4-Fluoro-N-phenylbenzenecarbohydrazonoyl chloride (Compound CXXII)

A mixture of 8.6 g. (41 mmoles) of phosphorus pentachloride, 8.0 g. (35 mmoles) of Compound CXXI and 60 ml. of anhydrous diethyl ether is refluxed under nitrogen for 16 hours and cooled to 20°–25° C., a solution of 15 g. of phenol in 20 ml. of diethyl ether is added, the mixture is stirred for 5 minutes, 15 ml. of methanol is added very slowly (exothermic reaction), and the mixture is concentrated at 70°–75° C. and cooled for 16 hours in a refrigerator to obtain the crystalline product which is washed with cold 5% water/acetone (3 g.), m.p. 118°–121° C.

Step 3 (Reaction CC)

Ethyl 3-(4'-fluorophenyl)-5-(1'-methylethyl)-1-phenyl-1H-pyrazole-4-carboxylate (Compound CXXIV)

0.28 g. (12.0 mmoles) of sodium is dissolved in 40 ml. of absolute ethanol stirred at 20°–25° C., 2.0 ml. (12.0 mmoles) of ethyl isobutyrylacetate (Compound CXXIII) is added dropwise with stirring at 20°–25° C., the mixture is stirred at 20°–25° C. for 15 minutes, 3.0 g. (12.0 mmoles) of Compound CXXII is added positionwise as a solid (the temperature increases to 35° C.), and the reaction mixture is stirred at 20°–25° C. for 4 hours, the reaction mixture being maintained under nitrogen throughout. The reaction mixture is quenched with 10 ml. of 10% hydrochloric acid, and the mixture is concentrated at reduced pressure (which results in dehydration of an intermediate). The residue is extracted with diethyl ether, and the diethyl ether extract is washed twice with saturated sodium chloride solution, dried over anhydrous magnesium sulfate and evaporated at reduced pressure. The residue is flash chromatographed on a silica gel column (2.5 cm.×20.3 cm.) utilizing chloroform as the eluant, and the chloroform is evaporated at reduced pressure to obtain the crude product as a red oil (3.1 g. (75%)).

Step 4 (Reaction CD)

3-(4'-Fluorophenyl)-5-(1'-methylethyl)-1-phenyl-1H-pyrazole-4-methanol (Compound CXXV)

A solution of 3.0 g. (8.5 mmoles) of Compound CXXIV in 20 ml. of anhydrous diethyl ether is added to a suspension of 0.65 g. (17.1 mmoles) of lithium aluminum hydride in 30 ml. of anhydrous diethyl ether stirred at 0°–5° C. under nitrogen, and the reaction mixture is stirred under the same conditions for 3 hours. The reaction mixture is quenched with about 5 ml. of ethyl acetate, and 10 ml. of 10% hydrochloric acid is added. The organic phase is separated, and the aqueous phase is extracted with diethyl ether. The organic phases are combined, washed twice with saturated sodium chloride solution, dried over anhydrous magnesium sulfate and evaporated at reduced pressure. The solid residue is recrystallized from 5:1 n-hexane/chloroform to obtain the crystalline product (2.2 g. (84%)), m.p. 144°–147° C.

Step 5 (Reaction CE)

4-Chloromethyl-3-(4'-fluorophenyl)-5-(1'-methylethyl)-1-phenyl-1H-pyrazole (Compound CXXVI)

A mixture of 2.0 g. (6.5 mmoles) of Compound CXXV, 0.6 ml. (8.2 mmoles) of thionyl chloride and 20 ml. of benzene (reagent grade) is refluxed under nitrogen for 4 hours and stirred at 20°–25° C. under nitrogen for 16 hours. The excess thionyl chloride and the benzene are evaporated at reduced pressure, additional benzene is added, the mixture is evaporated at reduced pressure twice, and the residue is dried under high vacuum. Petroleum ether is added to crystalline the product (2.1 g.), m.p. 124°–128° C.

Step 6 (Reaction A)

3-(4'-Fluorophenyl)-5-(1'-methylethyl)-1-phenyl-4-triphenylphosphoniummethyl-1H-pyrazole chloride (Compound CXXVII)

A mixture of 2.0 g. (6.1 mmoles) of Compound CXXVI, 2.1 g. (7.9 mmoles) of triphenylphosphine and 80 ml. of toluene is refluxed for 2 hours, stirred at 20°–25° C. for 64 hours, refluxed for 20 hours and cooled to 20°–25° C., the reaction mixture being maintained under nitrogen throughout. The product is collected by filtration and washed with diethyl ether (2.7 g.).

Step 7 (Reaction F)

Ethyl 3,5-di-(1',1'-dimethylethyl-diphenylsilyloxy)-7-[3'-(4''-fluorophenyl)-5'-(1'''-methylethyl)-1'-phenyl-1H-pyrazol-4'-yl]hept-6-enoate (Compound CXXIX)

The product is obtained from 1.0 g. (1.7 mmoles) of Compound CXXVII, 1.0 g. (1.5 mmoles) of ethyl 3,5-di-(1',1'-dimethylethyl-diphenylsilyloxy)-6-oxohexanoate (a mixture of isomers wherein the erythro:threo ratio is about 4:1 produced substantially as described in Steps A-D of Example 1 of said application Ser. No. 596,411, the principal difference being the use of triethylborane in Step B rather than tri-(n-butyl)borane) and 2.1 ml. of 1.65M. n-butyllithium/n-hexane (3.47 mmoles) according to the process of Step 1 of Examples 5 and 6. The product is obtained as a solid foam (0.53 mg. (36%)).

The product is a mixture of the (E)-erythro, (E)-threo, (Z)-erythro and (Z)-threo racemates wherein the ratio of the (E) isomers to the (Z) isomers is about 2:1 and the ratio of the erythro isomers to the threo isomers is about 4:1. The four isomers may be separated by conventional means. Each erythro racemate may be resolved to obtain the 3R,5S and 3S,5R enantiomers, and each threo racemate may be resolved to obtain the 3R,5R and 3S,5S enantiomers.

Step 8 (Reaction G)

Ethyl (E)-3,5-dihydroxy-7-[3'-(4''-fluorophenyl)-5'-(1''-methylethyl)-1'-phenyl-1H-pyrazol-4'-yl]hept-6-enoate 2 ml. of 1M. tetra-n-butylammonium fluoride/tetrahydrofuran (2 mmoles) is added to a mixture of 0.5 g. (0.51 mmoles) of Compound CXXIX (from the preceding step), 0.23 ml. (4 mmoles) of glacial acetic acid and 50 ml. of tetrahydrofuran (distilled prior to use), and the reaction mixture is stirred at 20°–25° C. for 3 days and at 40° C. for 1 day, additional 1M. tetra-n-butylammonium fluoride/tetrahydrofuran being added periodically. The reaction mixture is poured onto a mixture of ice and sodium bicarbonate solution, and the mixture is extracted with diethyl ether. The diethyl ether extract is washed twice with saturated sodium chloride solution, dried over anhydrous magnesium sulfate and concentrated at reduce pressure. The residue is chromatographed on a silica gel column (2.5 cm.×20.3 cm.) utilizing 7:2:1 methyl t-butyl ether/n-hexane/acetone as the eluant. The fractions containg the product are combined and evaporated at reduced pressure to obtain the product (65 mg.).

The product is an about 4:1 mixture of the (E)-erythro and (E)-threo racemates which may be separated by conventional means. The former may be resolved to obtain the 3R,5S and 3S,5R enantiomers, and the latter may be resolved to obtain the 3R,5R and 3S,5S enantiomers.

EXAMPLES 9–11

(E)-Trans-6-(2'-[3''-(4'''-fluorophenyl)-5''-(1'''-methylethyl)-1''-phenyl-1H-pyrazol-4''-yl]ethenyl)-4-hydroxy-3,4,5,6-tetrahydro-2H-pyran-2-one (Reactions O, P and S)

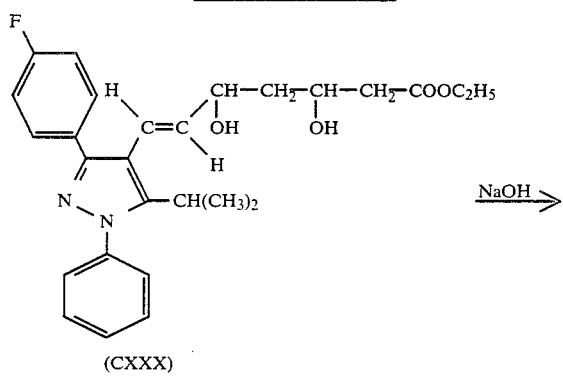

(CXXX)

-continued
(Reactions O, P and S)

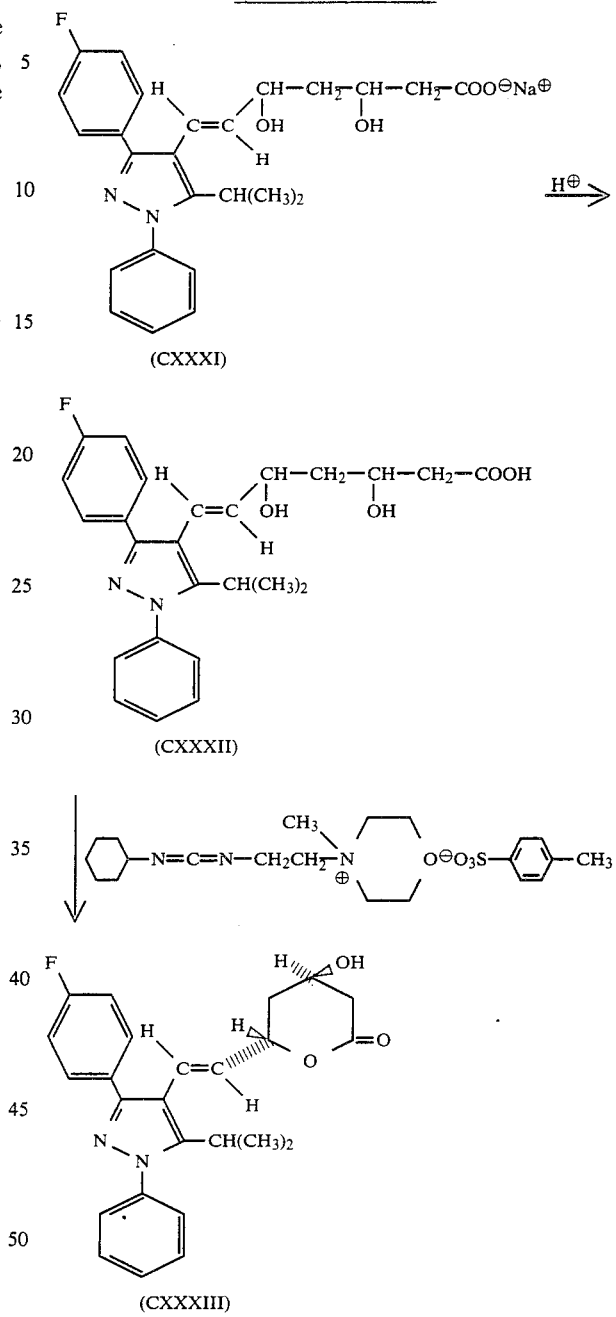

(CXXXI)

(CXXXII)

(CXXXIII)

(a) A mixture of 65 mg. (0.14 mmole) of Compound CXXX (from Example 8), 0.32 ml. of 0.5N. sodium hydroxide solution (0.16 mmole) and 10 ml. of ethanol is stirred at 20°–25° C. for 2 hours and evaporated to near dryness at reduced pressure. An about 4:1 mixture of the erythro and threo racemates of Compound CXXXI is present (Example 9).

(b) The product of Part (a) is dissolved in water and acidified with 10% hydrochloric acid, the solution is extracted with diethyl ether, and the diethyl ether extract is dried over anhydrous magnesium sulfate, filtered and evaporated at reduced pressure to an oil, an about 4:1 mixture of the erythro and threo racemates of Compound CXXXII (Example 10).

(c) The product of Part (b) is dissolved in 10 ml. of methylene chloride (reagent grade), 100 mg. of N-cyclohexyl-N'-[2'-(N''-methylmorpholinium)ethyl]carbodiimide p-toluenesulfonate is added, and the reaction mixture is stirred at 20°–25° C. for 3 hours and poured into sodium chloride solution. The mixture is extracted with a 1:1 mixture of diethyl ether and tetrahydrofuran, and the extract is dried over anhydrous magnesium sulfate and evaporated at reduced pressure to a yellow oil. The oil is flash chromatographed on a silica gel column (1.25 cm.×20.3 cm.) utilizing 7:2:1 methyl t-butyl ether/n-hexane/acetone as the eluant to obtain the product.

N.M.R. (CDCl$_3$): 1.23 (d,6H), 1.50–2.0 (m,2H), 2.21 (s,1H), 2.42–2.74 (m,2H), 3.08 (m,1H), 4.28 (m,1H), 5.15 (m,1H), 5.50 (dd, 1H), 6.68 (d,1H), 7.00 (t,2H), 7.31–7.58 (m,7H).

The product is a racemate that may be resolved to obtain the 4R,6S and 4S,6R enantiomers.

EXAMPLE 12

Sodium erythro-(E)-3,5-dihydroxy-7-[3'-(4''-fluorophenyl)-5'-(1''-methylethyl)-1'-phenyl-1H-pyrazol-4'-yl]hept-6-enoate

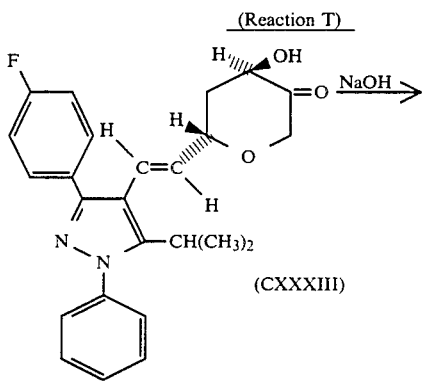

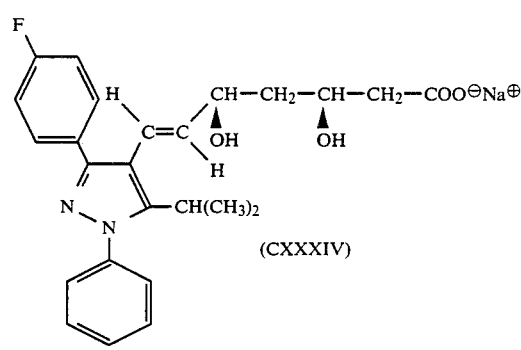

The product may be obtained by the process of Example 7. It is a racemate that may be resolved to obtain the 3R,5S and 3S,5R enantiomers.

EXAMPLE 13

Ethyl (±)-erythro-(E)-3,5-dihydroxy-7-[5'-(4''-fluorophenyl)-3'-(1''-methylethyl)-1'-phenyl-1H-pyrazol-4'-yl]hept-6-enoate

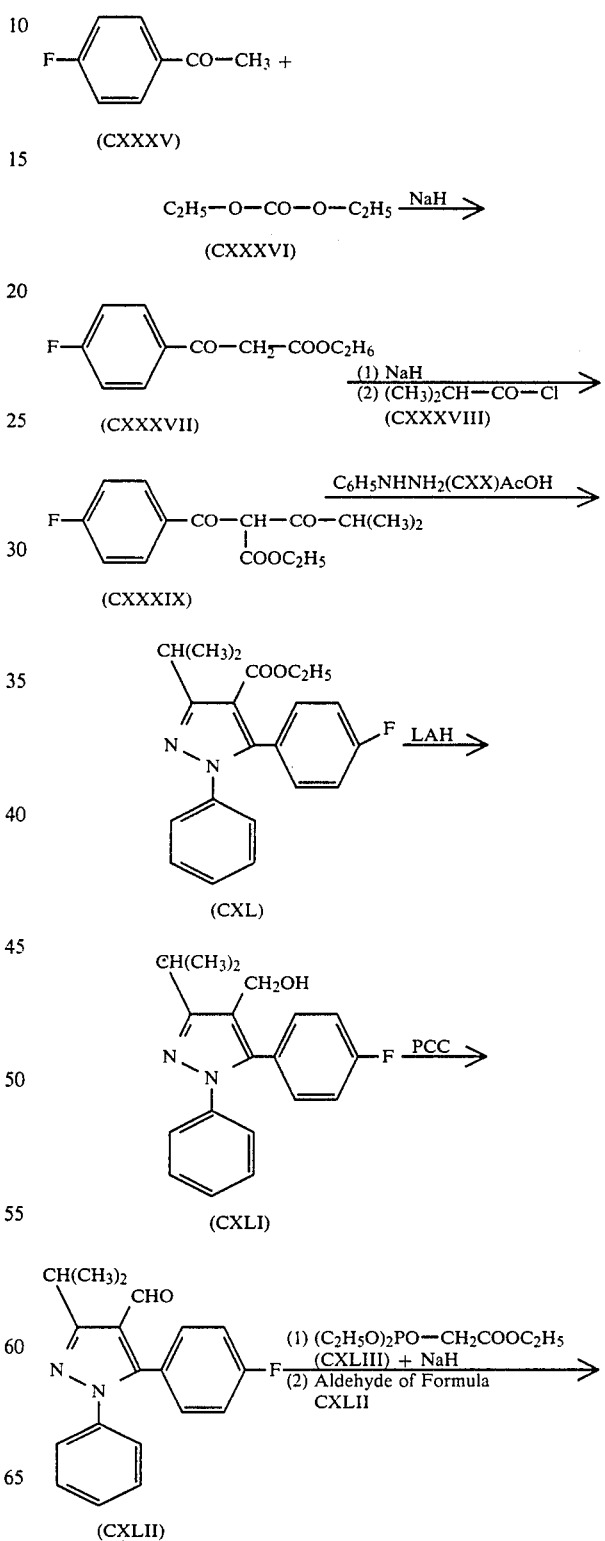

-continued

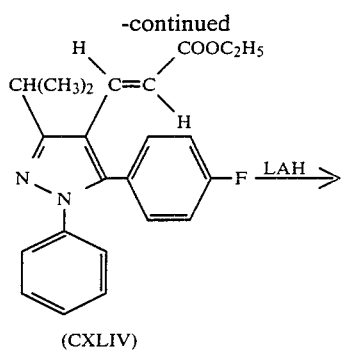

(CXLIV)

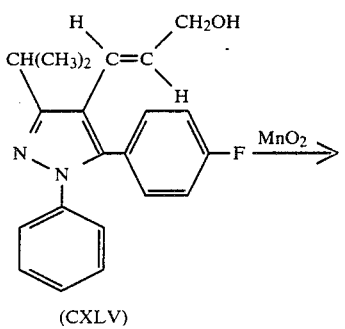

(CXLV)

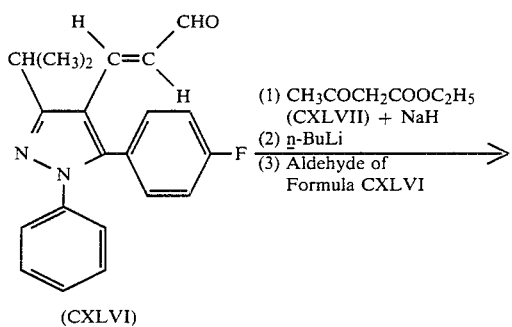

(CXLVI)

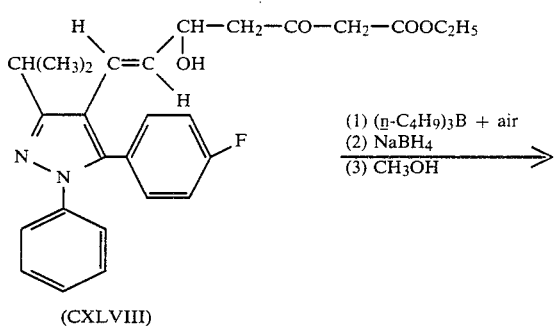

(CXLVIII)

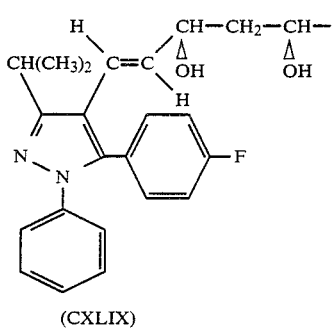

(CXLIX)

Step 1

Ethyl 3-(4'-fluorophenyl)-3-oxopropanoate (Compound CXXXVII)

57.92 g. (1.448 moles) of 60% sodium hydride/mineral oil is washed twice with pentane, the pentane is decanted, the sodium hydride is dried in a stream of nitrogen, 171 g. (1.448 moles) of diethyl carbonate is added neat at 20°–25° C., and the dropwise addition of a solution of 100 g. (0.724 mole) of 4-fluoroacetophenone in 100 ml of dry diethyl ether is commenced, the reaction mixture being stirred at 20°–25° C. under nitrogen throughout. After about 10% of the diethyl ether solution is added, 10 drops of ethanol is added (gas evolution commences immediately), and the balance of the solution is added dropwise over a period 1 hour at a rate such that the reaction mixture refluxes, the reaction mixture being stirred under nitrogen throughout. 1 kg. of dry diethyl ether is added to facilitate stirring, and the reaction mixture is refluxed under nitrogen for 3 hours and cooled to 0° C., water is carefully added (to destroy the excess sodium hydride) until all solids dissolve (the addition being exothermic), the diethyl ether phase is separated, the aqueous phase is acidified to pH 1 with concentrated hydrochloric acid and extracted twice with diethyl ether, and the three diethyl ether phases are combined, washed with saturated sodium chloride solution, dried over anhydrous magnesium sulfate, filtered and evaporated at reduced pressure to obtain an orange oil. The orange oil is fractionally distilled at about 1 mm. Hg. to obtain the product as a colorless liquid (117.8 g. (77%)). B.p. 117°–125° C.λ1 mm. Hg.

Step 2 (Reaction DA)

Ethyl 2-(4'-fluorobenzoyl)-4-methyl-3-oxopentanoate (Compound CXXXIX)

21.0 g. (524 mmoles) of 60% sodium hydride/mineral oil is washed twice with hexane, the hexane is decanted, the sodium hydride is dried in a stream of nitrogen and suspended in 500 ml. of dry tetrahydrofuran, the suspension is cooled to 0° C., 50.0 g. (238 mmoles) of Compound CXXXVII is added dropwise over a period of 20 minutes at 0° C., the reaction mixture is allowed to warm to 20°–25° C., stirred at this temperature for 30 minutes and cooled to 0° C., 38.0 g. (357 mmoles) of isobutyryl chloride is added dropwise with stirring at 0° C., and the reaction mixture is allowed to warm to 20°–25° C., stirred at 20°–25° C. for 3 hours and cooled to 0° C., the reaction mixture being stirred under nitrogen throughout. The reaction mixture is quenched at 0° C. with water, sufficient water being added to form a homogeneous mixture, the tetrahydrofuran is evaporated at reduced pressure, and the aqueous solution is acidified to pH 1 with 10% hydrochloric acid and extracted twice with 200 ml. portions of diethyl ether. The diethyl ether extracts are combined, washed with saturated sodium chloride solution, dried over anhydrous magnesium sulfate, filtered and evaporated at reduced pressure to obtain the crude product as an orange oil (72.99 g.).

Step 3 (Reaction DB)

Ethyl 5-(4″-fluorophenyl)-3-(1′-methylethyl)-1-phenyl-1H-pyrazole-4-carboxylate (Compound CXL)

38.6 g. (357 mmoles) of phenylhydrazine is added portionwise to a solution of 72.99 g. (≦238 mmoles) of crude Compound CXXXIX (from Step 2) in 300 ml. of glacial acetic acid stirred at 20°–25° C. under nitrogen (the addition being slightly exothermic) and the reaction mixture is stirred at 20°–25° C. under nitrogen for 16 hours and poured into 700 ml. of water. The mixture is extracted twice with 200 ml. portions of diethyl ether, and the diethyl ether extracts are combined, extracted with saturated sodium bicarbonate solution (until the aqueous phase remains basic), washed with saturated sodium chloride solution, dried over anhydrous magnesium sulfate, filtered and evaporated at reduced pressure to obtain an orange gel. The gel is triturated with petroleum ether to obtain the product as a yellow powder (29.57 g.). The mother liquor is evaporated at reduced pressure, and the residue is purified on a Waters Prep-500 high pressure liquid chromatograph (HPLC) having a silica gel column and utilizing methylene chloride as the solvent to obtain additional solid which is recrystallized from diethyl ether/hexane to obtain additional product (8.47 g.). Total yield: 38.04 g. (43% Steps 2 and 3 combined). M.p. 91.5°–93° C.

Step 4 (Reaction DC)

5-(4′-Fluorophenyl)-3-(1′-methylethyl)-1-phenyl-1H-pyrazole-4-methanol (Compound CXLI)

A solution of 42.0 g. (115 mmoles) of Compound CXL in 500 ml. of dry diethyl ether is added dropwise over a period of 1.5 hours to a suspension of 13.1 g. (345 mmoles) of lithium aluminum hydride in 250 ml. of dry diethyl ether stirred at 0° C. under nitrogen, and the resulting green suspension is allowed to warm to 20°–25° C. over a period of 1.5 hours with stirring under nitrogen. The reaction mixture is cooled to 0° C. and quenched by carefully adding water until the evolution of gas ceases, the resulting precipitate is collected by filtration and washed with ethyl acetate, the ethyl acetate washing is combined with the diethyl ether filtrate, and the organic solution is washed with saturated sodium chloride solution, dried over anhydrous magnesium sulfate, filtered and evaporated at reduced pressure to obtain the crude product as a tan powder (33.95 g. (95%)).

Step 5 (Reaction GA)

5-(4′-Fluorophenyl)-3-(1′-methylethyl)-1-phenyl-1H-pyrazole-4-carboxaldehyde (Compound CXLII)

A solution of 33.95 g. (≦109 mmoles) of crude Compound CXLI (from Step 4) in 250 ml. of methylene chloride is added rapidly dropwise to a solution of 70.75 g. (328 mmoles) of pyridinium chlorochromate in 350 ml. of methylene chloride stirred at 20°–25° C., and the reaction mixture is stirred at 20°–25° C. for 4 hours. 2.5 l. of diethyl ether is added, and the mixture is filtered through a 12.7 cm. pad of silica gel and evaporated at reduced pressure to obtain a brown solid which is recrystallized from diethyl ether to obtain the product as a white solid (24.46 g.). The mother liquor is chromatographed on a silica gel column utilizing 20% diethyl ether/hexane as the eluant to obtain additional product (3.66 g.). Total yield: 28.12 g. (83% Steps 4 and 5 combined). M.p. 110°–112° C.

Step 6 (Reaction GF)

Ethyl (E)-3-[5′-(4″-fluorophenyl)-3′-(1″-methylethyl)-1′-phenyl-1H-pyrazol-4′-yl]propenoate (Compound CXLIV)

761 mg. (19 mmoles) of 60% sodium hydride/mineral oil is washed twice with hexane, the hexane is decanted, the sodium hydride is dried in a stream of nitrogen and suspended in 50 ml. of dry tetrahydrofuran, the suspension is cooled to −15° C., 4.06 g. (18 mmoles) of triethyl phosphonoacetate is added dropwise with stirring at −15° C., the reaction mixture is stirred at −15° C. for 45 minutes, a solution of 5.59 g. (18 mmoles) of Compound CXLII in 50 ml. of dry tetrahydrofuran is added dropwise with stirring at −15° C., and the reaction mixture is stirred at −15° C. for 45 minutes and allowed to warm to 20°–25° C., the reaction mixture being stirred under nitrogen throughout. The reaction mixture is quenched at 20°–25° C. by the dropwise addition of saturated ammonium chloride solution, the tetrahydrofuran is evaporated at reduced pressure, and the solid residue is partitioned between ethyl acetate and water. The organic phase is separated, washed twice with saturated sodium chloride solution, dried over anhydrous magnesium sulfate, filtered and evaporated at reduced pressure to obtain the crude product as a yellow solid (6.59 g.).

Step 7 (Reaction GG)

(E)-3-[5′-(4″-Fluorophenyl)-3′-(1″-methylethyl)-1′-phenyl-1H-pyrazol-4′-yl]prop-2-en-1-ol (Compound CXLV)

46.4 ml. of 1.5M. diisobutylaluminum hydride/toluene (69.6 mmoles) is added dropwise to a solution of 6.59 g. (≦17 mmoles) of crude Compound CXLIV (from Step 6) in 150 ml. of dry tetrahydrofuran stirred at 0° C. under nitrogen, the reaction mixture is stirred at 0° C. under nitrogen for 45 minutes, quenched at 0° C. by the dropwise addition of saturated sodium sulfate solution and allowed to warm to 20°–25° C., and sufficient 10% hydrochloric acid is added to dissolve the resulting gel. The organic phase is separated, the aqueous phase is extracted with diethyl ether, and the organic phase and diethyl ether extract are combined, washed with saturated sodium chloride solution, dried over anhydrous magnesium sulfate, filtered and evaporated at reduced pressure to obtain the crude product as a yellow foam (6.13 g.).

Step 8 (Reaction GH)

(E)-3-[5′-(4″-Fluorophenyl)-3′-(1″-methylethyl)-1′-phenyl-1H-pyrazol-4′-yl]propenal (Compound CXLVI)

A mixture of 36.8 g. (423 mmoles) activated manganese dioxide and a solution of 6.13 g. (≦17 mmoles) of crude Compound CXLV (from Step 7) in 150 ml. of diethyl ether is stirred at 20°–25° C. for 16 hours and filtered through a 5.1 cm. pad of Celite filter aid. The Celite is washed with ethyl acetate, and the ethyl acetate washing and the diethyl ether filtrate are combined and evaporated at reduced pressure to obtain a yellow solid which is recrystallized from diethyl ether to obtain the product as a yellow solid (1.59 g.). The mother liquor is evaporated at reduced pressure, and the residue is chromatographed on a silica gel column utilizing 30% diethyl ether/hexane as the eluant to obtain additional product (2.0 g.). Total yield: 3.59 g. (59% Steps 6, 7 and 8 combined). M.p. 146°–150° C.

Step 9 (Reaction J)

Ethyl (±)-(E)-7-[5'-(4''-fluorophenyl)-3'-(1''-methylethyl)-1'-phenyl-1H-pyrazol-4'-yl]-5-hydroxy-3-oxohept-6-enoate (Compound CXLVIII)

1.355 g. (33.88 mmoles) of 60% sodium hydride/mineral oil is washed with hexane, the hexane is decanted, the sodium hydride is suspended in 100 ml. of dry tetrahydrofuran, the suspension is cooled to −15° C., 4.01 g. (30.8 mmoles) of ethyl acetoacetate is added dropwise with stirring at −15° C., the reaction mixture is stirred at −15° C., for 30 minutes, 20.2 ml. of 1.6M. n-butyllithium/hexane (32.3 mmoles) is added dropwise with stirring at −15° C., the reaction mixture is stirred at −15° C. for 15 minutes, a solution of 5.14 g. (15.4 mmoles) of Compound CXLVI in 50 ml. of dry tetrahydrofuran is added dropwise with stirring at −15° C., and the reaction mixture is stirred at −15° C. for 1 hour, the reaction mixture being stirred under nitrogen throughout. The reaction mixture is quenched at −15° C. with saturated ammonium chloride solution and warmed to 20°–25° C., the tetrahydrofuran is evaporated at reduced pressure, and the residue is partitioned between diethyl ether and water. The aqueous phase is extracted with diethyl ether, and the diethyl ether extract and diethyl ether phase are combined, washed with saturated sodium chloride solution, dried over anhydrous magnesium sulfate, filtered and evaporated at reduced pressure to obtain a yellow foam which is chromatographed on a silica gel column (350 g.) utilizing 1:1 diethyl ether/hexane as the eluant to obtain the product as a yellow oil (5.42 g. (76%)).

The product is a racemate that may be resolved to obtain the R and S enantiomers.

Step 10 (Reaction K)

Ethyl (±)-erythro-(E)-3,5-dihydroxy-7-[5'-(4''-fluorophenyl)-3'-(1''-methylethyl)-1'-phenyl-1H-pyrazol-4'-yl]hept-6-enoate (Compound CXLIX)

23.34 ml. of 1.0M. tri-n-butylborane/tetrahydrofuran (23.34 mmoles) is added via syringe to a solution of 5.42 g. (11.67 mmoles) of Compound CXLVIII in 100 ml. of dry tetrahydrofuran stirred at 20°–25° C., air is bubbled through the reaction mixture of 2 minutes with stirring, the reaction mixture is stirred at 20°–25° C. for 1 hour and cooled to −78° C., 2.21 g. (58.35 mmoles) of sodium borohydride is added, the reaction mixture is stirred at −55° C. for 16 hours and at 0° C. for 1 hour and, if thin layer chromatography reveals the presence of some starting material, the reaction mixture is cooled to −55° C., an additional 1.1 g. (29.1 mmoles) of sodium borohydride is added, and the reaction mixture is stirred at −55° C. for 16 hours and warmed to 0° C., the reaction mixture being stirred under nitrogen throughout. The reaction mixture is quenched at 0° C. by the addition of 10% hydrochloric acid (until bubbling ceases), warmed to 20°–25° C. and partitioned between diethyl ether and water. The aqueous phase is extracted with diethyl ether, and the diethyl ether extract and the diethyl ether phase are combined, washed with saturated sodium chloride solution, dried over anhydrous magnesium sulfate, filtered and evaporated at reduced pressure to a clear oil. The oil is dissolved in 10 ml. of isopropanol and the solution is evaporated at reduced pressure, this procedure is repeated to obtain a pale green wax, the wax is dissolved in a minimum amount of hot isopropanol, and the solution is allowed to cool to 20°–25° C. and stored at −30° C. for 64 hours. The resulting waxy solid is collected by filtration and vacuum dried to obtain a white powder (erythro:-threo = ∼9:1). The powder is recrystallized from isopropanol to obtain a waxy solid which is vacuum dried to obtain a white poweder (erythro:threo = ∼19:1). The white powder is warmed in methanol at 40°–60° C. for 2 minutes, the methanol is evaporated at reduced pressure, the residue is warmed in methanol at 40°–60° C. for 2 minutes and the methanol is evaporated at reduced pressure, and this procedure is repeated once more to obtain a white foam which is recrystallized from benzene/hexane to obtain the product as a white solid (1.05 g. (19%)), m.p. 101°–104° C.

N.M.R. (CDCl$_3$): 1.28 (t (J = 7.5 Hz.), 3H), 1.40 (d (J = 7 Hz.), 6H), 1.65 (m, 2H), 2.48 (m, 2H), 3.11 (bs, 1H), 3.22 (m, 1H), 3.70 (bs, 1H), 4.18 (q (J = 7.5 Hz.), 2H), 4.24 (m, 1H), 4.42 (m, 1H), 5.68 (dd (J$_1$ = 15.5 Hz., J$_2$ = 5.5 Hz.), 1H), 6.38 (d (J = 15.5 Hz.), 1H), 7.05 (t (J = 7.5 Hz.), 2H), 7.20 (m, 7H).

The product is a mixture of the erythro and threo racemates wherein the ratio of the former to the latter is ∼19:1 and which, if desired, may be separated by conventional means to obtain the pure erythro and threo racemates. The former may be resolved to obtain the 3R,5S and 3S,5R enantiomers, of which the former is preferred, and the latter may be resolved to obtain the 3R,5R and 3S,5S enantiomers. The use of a nonstereoselective reduction would afford a mixture of all four enantiomers wherein the ratio of the erythro isomers to the threo isomers ranges from 3:2 to 2:3.

EXAMPLE 14

Sodium erythro-(±)-(E)-3,5-dihydroxy-7-[5'-(4''-fluorophenyl)-3'-(1''-methylethyl)-1'-phenyl-1H-pyrazol-4'-yl]hept-6-enoate

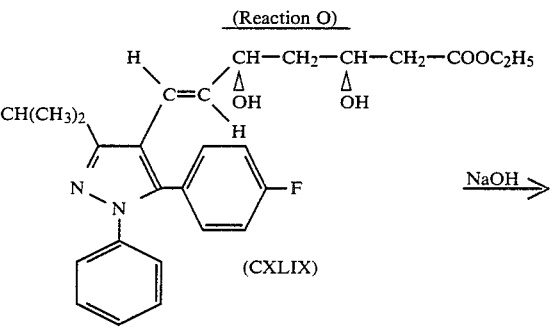

(Reaction O)

(CXLIX) NaOH →

-continued
(Reaction O)

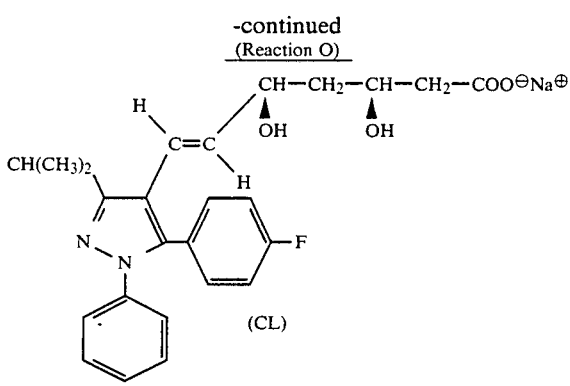
(CL)

4.2 ml. of 0.5N. sodium hydroxide solution (2.1 mmoles) is added to a solution of 1.02 g. (2.2 mmoles) of Compound CXLIX (Step 10 of Example 13) in 25 ml. of 95% ethanol, the mixture is stirred at 20°–25° C. under nitrogen for 5 hours, the ethanol is evaporated at reduced pressure, and the residue is partitioned between diethyl ether and water. The aqueous phase is washed twice with diethyl ether and lyophilized at −78° C. for 16 hours. The residue is warmed to 20°–25° C. and lyophilized at −78° C. for another 16 hours to obtain the product as a flocculant white solid (861 mg. (85%)), m.p. 205°–210° C. (dec.).

N.M.R. $(CDCl_3+CD_3OD)$: 1.35 (d (J=7.5 hz.), 6H), 1.52 (m), 3.18 (m, 1H), 4.11 (m, 1H), 4.25 (m, 1H), 5.64 (dd ($J_1=15$ Hz., $J_2=5$ Hz.), 1H), 6.32 (d (J=15.5 Hz), 1H), 6.95 (t (J=9.5 Hz.), 2H), 7.16 (m, 7H).

The product is a mixture of the erythro and threo racemates wherein the ratio of the former to the latter is ~19:1 and which, if desired, may be separated by conventional means to obtain the pure erythro and threo racemates. The former may be resolved to obtain the 3R,5S and 3S,5R enantiomers, of which the former is preferred, and the latter may be resolved to obtain the 3R,5R and 3S,5S enantiomers. The use of a starting material obtained by utilizing a non-stereoselective reduction in Step 10 of Example 13 would afford a mixture of all four enantiomers wherein the ratio of the erythro isomers to the threo isomers ranges from 3:2 to 2:3.

EXAMPLE 15

Ethyl (±)-erythro-(E)-3,5-dihydroxy-7-[5'-(3",5"-dimethylphenyl)-3'-(1"-methylethyl-1'-phenyl-1H-pyrazol-4'-yl]hept-6-enoate (CLI)

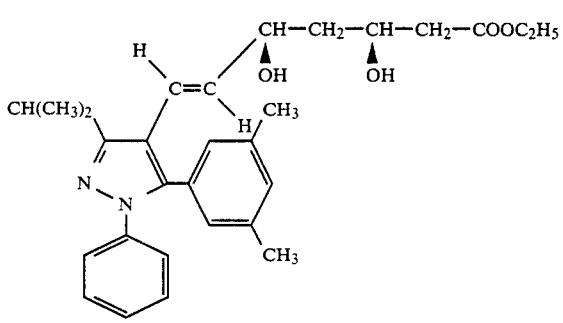

The product may be obtained as a solid foam by the processes of Steps 3–10 of Example 13 from ethyl 2-(3',5'-dimethylbenzoyl)-4-methyl-3-oxopentanoate.

Said compound is synthesized from ethyl 4-methyl-3-oxopentanoate and 3,5-dimethylbenzoyl chloride by Reaction DE carried out analogously to Step 2 of Example 13.

N.M.R. $(CDCl_3)$: 1.28 (t (J=7.5 Hz.), 3H), 1.4 (d (J=7.5 Hz.), 6H), 1.68 (m, 2H), 2.25 (s, 6H), 2.46 (m, 2H), 2.98 (bs, 1H), 3.22 (m, 1H), 3.74 (d (J=2.5 Hz.), 1H), 4.16 (q (J=7.5 Hz.), 2H), 4.22 (m, 1H), 4.39 (m, 1H), 5.69 (dd ($J_1=17.5$ Hz., $J_2=7.5$ Hz), 1H), 6.38 (d (J=17.5 Hz.), 1H), 6.79 (bs, 2H), 6.95 (bs, 1H), 7.2 (m, 5H).

The product is a mixture of the erythro and threo racemates wherein the ratio of the former to the latter is ~9:1 and which, if desired, may be separated by conventional means to obtain the pure erythro and threo racemates. The former may be resolved to obtain the 3R,SS and 3S,5R enantiomers, of which the former is preferred, and the latter may be resolved to obtain the 3R,5R and 3S,5S enantiomers. The use of a non-stereoselective reduction would afford a mixture of all four enantiomers wherein the ratio of the erythro isomers to the threo isomers ranges from 3:2 to 2:3.

EXAMPLE 16

Sodium (±)-erythro-(E)-3,5-dihydroxy-7-[5'-(3",5"-dimethylphenyl)-3'-(1"-methylethyl)-1'-phenyl-1H-pyrazol-4'-yl]hept-6-enoate (CLII)

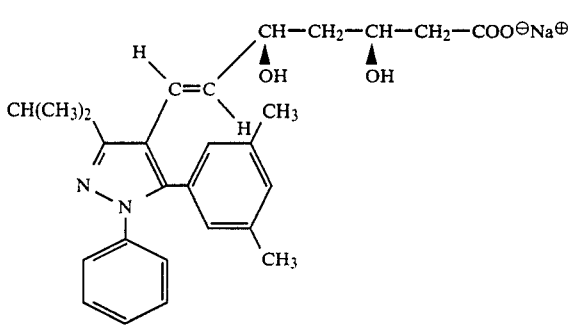

The product may be obtained from Compound CLI by the process of Example 14. M.p. 203°–210° C. (dec.).

N.M.R. $(CDCl_3+CD_3OD)$: 1.40 (d (J=7 Hz.)), 1.55 (bm), 2.12 (s, 6H), 2.26 (bm), 3.18 (m, 1H), 4.11 (bm, 1H), 4.22 (bm, 1H), 5.64 (dd ($J_1=15$ Hz., $J_2=5$ Hz.), 1H), 6.30 (d (J=15 Hz.), 1H), 6.70 (s, 2H), 6.82 (s, 1H), 7.15 (m, 5H).

The product is a mixture of the erythro and threo racemates wherein the ratio of the former to the latter is ~9:1 and which, if desired, may be separated by conventional means to obtain the pure erythro and threo racemates. The former may be resolved to obtain the 3R,5S and 3S,5R enantiomers, of which the former is preferred, and the latter may be resolved to obtain the 3R,5R and 3S,5S enantiomers. The use of a starting material prepared by the process of Example 15 but wherein the last step is non-stereoselective reduction would afford a mixture of all four enantiomers wherein the ratio of the erythro isomers to the threo isomers ranges from 3:2 to 2:3.

TABLE

Examples 17-19
The following compounds of Group IDa may be synthesized by the processes set forth above:

| $R_1$ | $R_2$ | $R_3$ | $R_4$ | $R_5$ | $R_6$ | $R_7$ | $R_{10}$ | $R_{11}$ | X | Isomer | M.P. |
|---|---|---|---|---|---|---|---|---|---|---|---|
| Ex. 17 i-$C_3H_7$ | H | H | H | H | H | H | H | $C_2H_5$ | (E)—CH=CH— | >90% E | oil |
| Ex. 18 i-$C_3H_7$ | H | H | H | H | H | H | H | $Na^{\oplus}$ | (E)—CH=CH— | >90% E | 206°-210° C. (dec.) |
| Ex. 19 i-$C_3H_7$ | H | H | H | 4-F | H | H | H | $Na^{\oplus}$ | —$CH_2CH_2$— | >90% E | 198°-210° C. (dec.) |

E = erythro racemate

N.M.R. DATA: Ex. 17 (CDCl$_3$): 1.26 (t, 3H), 1.41 (d, 6H), 1.72 (m, 2H), 2.49 (m, 2H), 2.96 (bs, 1H), 3.25 (m, 1H), 3.69 (bs, 1H), 4.18 (q, 2H), 4.25 (m, 1H), 4.42 (m, 1H), 5.68 (dd, 1H), 6.4 (d, 1H), 7.24 (m, 10H). Ex. 19 (CD$_3$OD): 1.36 (d, 6H), 1.55 (m, 4H), 2.34 (m, 4H), 3.66 (m, 1H), 4.08 (m, 1H), 7.2 (m, 9H).

Throughout the examples, the term "reduced pressure" denotes aspirator pressure. Where no solvent is specified in connection with a solution, the solvent is water, and all solvent mixtures are by volume. When a reaction is carried out under nitrogen, dry nitrogen is used to maintain anhydrous conditions (except where the reaction medium contains water).

All nuclear magnetic resonance spectra were taken at ambient temperature on a 200 MHz. spectrometer. All chemical shits are given in p.p.m. (δ) relative to tetramethylsilane and where a single δ value is given for anything other than a sharp singlet, it is its center point. In the N.M.R. data:

| | | | |
|---|---|---|---|
| bm = | broad multiplet | bs = | broad singlet |
| d = | doublet | dd = | doublet of a doublet |
| m = | multiplet | q = | quartet |
| s = | singlet | t = | triplet |

In the optical rotation data, the concentrations (c) are given in g./100 ml.

Each of the compounds of the examples wherein Z is a group of Formula a wherein $R_{11}$ is a cation may be converted into the corresponding compounds wherein $R_{11}$ is hydrogen or a different cation M, particularly the latter, especially M', by the processes set forth in Reaction Scheme IV.

Each of the compounds of Examples 1-19 (including each of the possible optical isomers of the examples not directed to single isomers) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

What is claimed is:

1. A compound of the formula

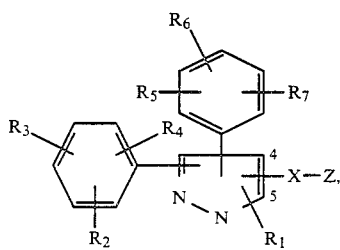

wherein
$R_1$ is $C_{1-6}$alkyl not containing an asymmetric carbon atom, each of $R_2$ and $R_5$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy, each of $R_3$ and $R_6$ is independently hydrogen, $C_{1-3}$alkyl, $C_{1-3}$alkoxy, trifluoromethyl, fluoro, chloro, phenoxy or benzyloxy, each of $R_4$ and $R_7$ is independently hydrogen, $C_{1-2}$alkyl, $C_{1-2}$alkoxy, fluoro or chloro, with the provisos that not more than one of $R_2$ and $R_3$ is trifluoromethyl, not more than one of $R_2$ and $R_3$ is phenoxy, not more than one of $R_2$ and $R_3$ is benzyloxy, not more than one of $R_5$ and $R_6$ is trifluoromethyl, not more than one of $R_5$ and $R_6$ is phenoxy, and not more than one of $R_5$ and $R_6$ is benzyloxy, X is —$(CH_2)_m$—, —CH=CH—, —CH=CH—$CH_2$— or —$CH_2$—CH=CH—, wherein m is 0, 1, 2 or 3, and Z is

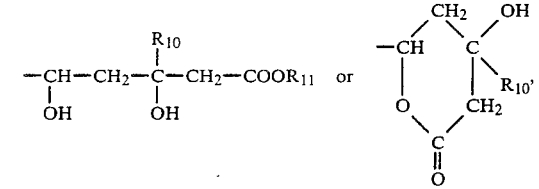

wherein $R_{10}$ is hydrogen or $C_{1-3}$alkyl, and $R_{11}$ is hydrogen, $R_{12}$ or M, wherein
$R_{12}$ is a physiologically acceptable and hydrolyzable ester group, and
M is a cation,
with the provisos that (i) the —X—Z group is in the 4- or 5-position of the pyrazole ring, and (ii) the $R_1$ group and the —X—Z group are ortho to each other.

2. A compound according to claim 1 wherein M is a pharmaceutically acceptable cation.

3. A compound according to claim 2 having the formula

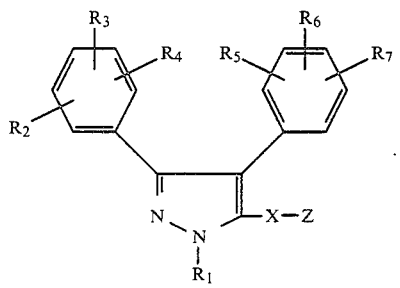

4. A compound according to claim 3 wherein $R_{12}$ is $C_{1-3}$alkyl, n-butyl, i-butyl, t-butyl or benzyl.

5. A compound according to claim 4 having the formula

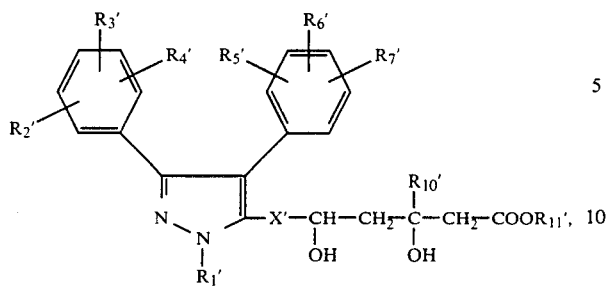

wherein
- R$_1'$ is C$_{1-3}$alkyl, n-butyl or i-butyl,
- R$_2'$ is hydrogen, C$_{1-3}$alkyl, C$_{1-3}$alkoxy, trifluoromethyl, fluoro or chloro,
- R$_3'$ is hydrogen, C$_{1-2}$alkyl, C$_{1-2}$alkoxy, fluoro or chloro,
- R$_4'$ is hydrogen or methyl,
- R$_5'$ is hydrogen, C$_{1-3}$alkyl, C$_{1-3}$alkoxy, trifluoromethyl, fluoro or chloro,
- R$_6'$ is hydrogen, C$_{1-2}$alkyl, C$_{1-2}$alkoxy, fluoro or chloro,
- R$_7'$ is hydrogen or methyl,
- R$_{10}'$ is hydrogen or methyl,
- R$_{11}'$ is hydrogen, R$_{12}'$ or M,
  wherein
  R$_{12}'$ is C$_{1-3}$alkyl, n-butyl, i-butyl, t-butyl or benzyl, and
- M is a pharmaceutically acceptable cation, and
- X' is —CH$_2$CH$_2$— or —CH═CH—.

6. A compound according to claim 5 wherein
- R$_2'$ is hydrogen or fluoro,
- R$_3'$ is hydrogen,
- R$_4'$ is hydrogen,
- R$_5'$ is hydrogen or fluoro,
- R$_6'$ is hydrogen or methyl,
- R$_{10}'$ is hydrogen,
- R$_{11}'$ is hydrogen, C$_{1-3}$alkyl or M,
  wherein
- M is a pharmaceutically acceptable cation, and
- X' is (E)—CH═CH—.

7. A compound according to claim 6 having the formula

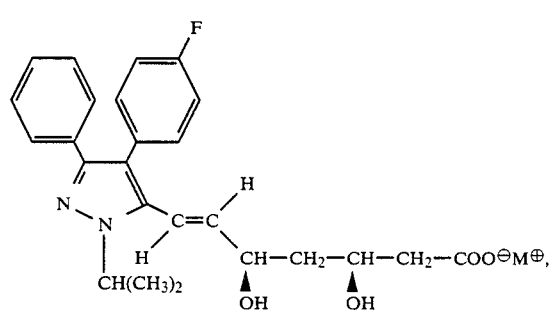

wherein M$^\oplus$ is a pharmaceutically acceptable cation.

8. A compound according to claim 3 having the formula

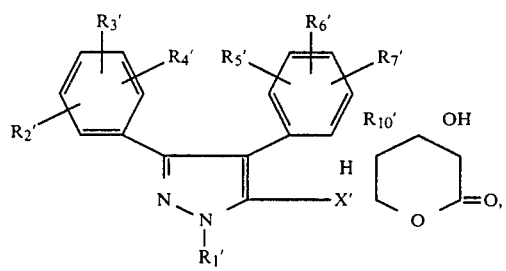

wherein
- R$_1'$ is C$_{1-3}$alkyl, n-butyl or i-butyl,
- R$_2'$ is C$_{1-3}$alkyl, C$_{1-3}$alkoxy, trifluoromethyl, fluoro or chloro,
- R$_3'$ is hydrogen, C$_{1-2}$alkyl, C$_{1-2}$alkoxy, fluoro or chloro,
- R$_4'$ is hydrogen or methyl,
- R$_5'$ is hydrogen, C$_{1-3}$alkyl, C$_{1-3}$alkoxy, trifluoromethyl, fluoro or chloro,
- R$_6'$ is hydrogen, C$_{1-2}$alkyl, C$_{1-2}$alkoxy, fluoro or chloro,
- R$_7'$ is hydrogen or methyl,
- R$_{10}'$ is hydrogen or methyl, and
- X' is —CH$_2$CH$_2$— or —CH═CH—.

9. A compound according to claim 2 having the formula

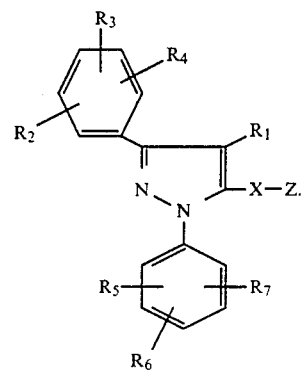

10. A compound according to claim 2 having the formula

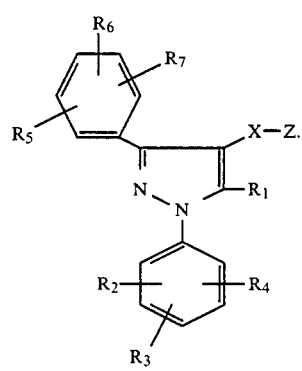

11. A compound according to claim 2 having the formula

12. A compound according to claim 11 wherein $R_{12}$ is $C_{1-3}$alkyl, n-butyl, i-butyl, t-butyl or benzyl.

13. A compound according to claim 12 having the formula wherein
- $R_1'$ is $C_{1-3}$alkyl, n-butyl or i-butyl,
- $R_2'$ is hydrogen, $C_{1-3}$alkyl, $C_{1-3}$alkoxy, trifluoromethyl, fluoro or chloro,
- $R_3'$ is hydrogen, $C_{1-2}$alkyl, $C_{1-2}$alkoxy, fluoro or chloro,
- $R_4'$ is hydrogen or methyl,
- $R_5'$ is hydrogen, $C_{1-3}$alkyl, $C_{1-3}$alkoxy, trifluoromethyl, fluoro or chloro,
- $R_6'$ is hydrogen, $C_{1-2}$alkyl, $C_{1-2}$alkoxy, fluoro or chloro,
- $R_7'$ is hydrogen or methyl,
- $R_{10}'$ is hydrogen or methyl,
- $R_{11}'$ is hydrogen, $R_{12}'$ or M,
  wherein
    $R_{12}'$ is $C_{1-3}$alkyl, n-butyl, i-butyl, t-butyl or benzyl, and
    M is a pharmaceutically acceptable cation, and
- $X'$ is —CH$_2$CH$_2$— or —CH═CH—.

14. A compound according to claim 13 wherein
- $R_2'$ is hydrogen or fluoro,
- $R_3'$ is hydrogen,
- $R_4'$ is hydrogen,
- $R_5'$ is hydrogen or fluoro,
- $R_6'$ is hydrogen or methyl,
- $R_{10}'$ is hydrogen,
- $R_{11}'$ is hydrogen, $C_{1-3}$alkyl or M,
  wherein
    M is a pharmaceutically acceptable cation, and
- $X'$ is (E)—CH═CH—.

15. A compound according to claim 14 wherein $R_1'$ is $C_{1-3}$alkyl.

16. A compound according to claim 15 wherein $R_{11}'$ is a pharmaceutically acceptable cation.

17. A compound according to claim 16 having the formula wherein $M^\oplus$ is a pharmaceutically acceptable cation.

18. A compound according to claim 17 having the formula

19. A compound according to claim 11 having the formula wherein
- $R_1'$ is $C_{1-3}$alkyl, n-butyl or i-butyl,
- $R_2'$ is hydrogen, $C_{1-3}$alkyl, $C_{1-3}$alkoxy, trifluoromethyl, fluoro or chloro,
- $R_3'$ is hydrogen, $C_{1-2}$alkyl, $C_{1-2}$alkoxy, fluoro or chloro,
- $R_4'$ is hydrogen or methyl,
- $R_5'$ is hydrogen, $C_{1-3}$alkyl, $C_{1-3}$alkoxy, trifluoromethyl, fluoro or chloro,
- $R_6'$ is hydrogen, $C_{1-2}$alkyl, $C_{1-2}$alkoxy, fluoro or chloro,
- $R_7'$ is hydrogen or methyl,
- $R_{10}'$ is hydrogen or methyl, and
- $X'$ is —CH$_2$CH$_2$— or —CH═CH—.

20. A compound according to claim 16 having the formula

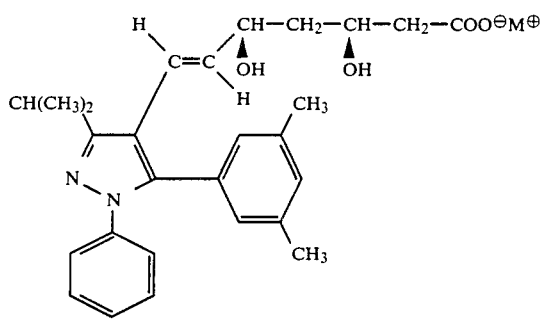

wherein M⊕ is a pharmaceutically acceptable cation.

21. A pharmaceutical composition comprising an effective amount of a compound according to claim 2 and a pharmaceutically acceptable carrier, said effective amount being an amount effective for inhibiting cholesterol biosynthesis in a mammal.

22. A method of inhibiting cholesterol biosynthesis comprising administering to a mammal in need of such treatment an effective amount of a compound according to claim 2, said effective amount being an amount effective for inhibiting cholesterol biosynthesis.

23. A method of treating atherosclerosis comprising administering to a mammal in need of such treatment an effective amount of a compound according to claim 2, said effective amount being an amount effective for the treatment of atherosclerosis.

24. A method of treating atherosclerosis according to claim 23 comprising administering to a mammal in need of such treatment an effective amount of a compound of the formula

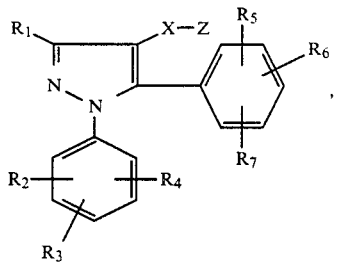

said effective amount being an amount effective for the treatment of atherosclerosis.

25. A method of treating atherosclerosis according to claim 24 comprising administering to a mammal in need of such treatment an effective amount of a compound of the formula

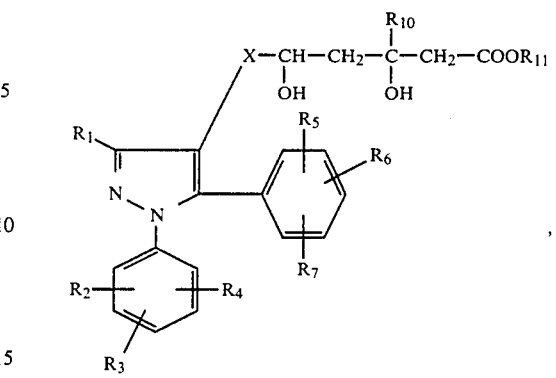

said effective amount being an amount effective for the treatment of atherosclerosis.

26. A method of treating atherosclerosis according to claim 25 comprising administering to a mammel in need of such treatment an effective amount of a compound of the formula

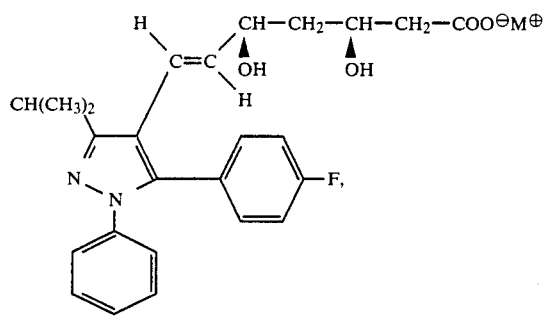

wherein M⊕ is a pharmaceutically acceptable cation, said effective amount being an amount effective for the treatment of atherosclerosis.

27. A method of treating atherosclerosis according to claim 26 comprising administering to a mammal in need of such treatment an effective amount of a compound of the formula

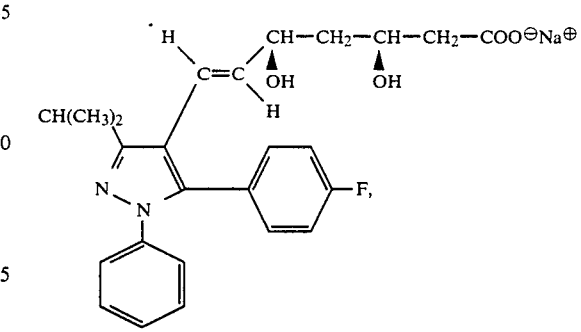

said effective amount being an amount effective for the treatment of atherosclerosis.

* * * * *